US010131951B2

(12) United States Patent
Sparks et al.

(10) Patent No.: US 10,131,951 B2
(45) Date of Patent: *Nov. 20, 2018

(54) ASSAY SYSTEMS FOR GENETIC ANALYSIS

(71) Applicant: Ariosa Diagnostics, Inc., San Jose, CA (US)

(72) Inventors: Andrew Sparks, San Jose, CA (US); Arnold Oliphant, San Jose, CA (US); Jacob Zahn, San Jose, CA (US); Ken Song, San Jose, CA (US); John Stuelpnagel, San Jose, CA (US)

(73) Assignee: ARIOSA DIAGNOSTICS, INC., San Jose, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/206,202

(22) Filed: Jul. 8, 2016

(65) Prior Publication Data

US 2017/0121769 A1    May 4, 2017

Related U.S. Application Data

(63) Continuation of application No. 13/205,490, filed on Aug. 8, 2011, now abandoned, which is a continuation-in-part of application No. 13/013,732, filed on Jan. 25, 2011, now abandoned.

(60) Provisional application No. 61/371,605, filed on Aug. 6, 2010.

(51) Int. Cl.
| | |
|---|---|
| *C12Q 1/68* | (2018.01) |
| *C12Q 1/6883* | (2018.01) |
| *C12Q 1/6827* | (2018.01) |
| *C12Q 1/6858* | (2018.01) |
| *C12Q 1/6869* | (2018.01) |

(52) U.S. Cl.
CPC ......... *C12Q 1/6883* (2013.01); *C12Q 1/6827* (2013.01); *C12Q 1/6858* (2013.01); *C12Q 1/6869* (2013.01); *C12Q 2600/156* (2013.01); *C12Q 2600/158* (2013.01); *H05K 999/99* (2013.01)

(58) Field of Classification Search
None
See application file for complete search history.

(56) References Cited

U.S. PATENT DOCUMENTS

| | | |
|---|---|---|
| 4,683,195 A | 7/1987 | Mullis et al. |
| 4,988,617 A | 1/1991 | Landegren et al. |
| 5,143,854 A | 9/1992 | Pirrung et al. |

(Continued)

FOREIGN PATENT DOCUMENTS

| | | |
|---|---|---|
| GB | 970444 | 9/1964 |
| GB | 2299166 A | 9/1996 |

(Continued)

OTHER PUBLICATIONS

Boyle et al. Bioinformatics. 2014. 30(18):2670-2672.*

(Continued)

*Primary Examiner* — Joseph G. Dauner
(74) *Attorney, Agent, or Firm* — Mintz, Levin, Cohn, Ferris, Glovsky and Popeo, P.C.

(57) ABSTRACT

The present invention provides assay systems and methods for detection of copy number variation at one or more loci and polymorphism detection at one or more loci in a mixed sample from an individual.

19 Claims, 15 Drawing Sheets

Specification includes a Sequence Listing.

(56) References Cited

U.S. PATENT DOCUMENTS

| | | |
|---|---|---|
| 5,242,794 A | 9/1993 | Whiteley et al. |
| 5,270,184 A | 12/1993 | Walker et al. |
| 5,399,491 A | 3/1995 | Kacian et al. |
| 5,409,818 A | 4/1995 | Davey et al. |
| 5,413,909 A | 5/1995 | Bassam et al. |
| 5,422,252 A | 6/1995 | Walker et al. |
| 5,437,975 A | 8/1995 | McClelland |
| 5,494,810 A | 2/1996 | Barany et al. |
| 5,547,839 A | 8/1996 | Dower et al. |
| 5,554,517 A | 9/1996 | Davey et al. |
| 5,578,832 A | 11/1996 | Trulson et al. |
| 5,631,734 A | 5/1997 | Stern et al. |
| 5,648,245 A | 7/1997 | Fire et al. |
| 5,800,992 A | 9/1998 | Fodor et al. |
| 5,808,041 A | 9/1998 | Padhye et al. |
| 5,830,711 A | 11/1998 | Barany et al. |
| 5,834,758 A | 11/1998 | Trulson et al. |
| 5,856,092 A | 1/1999 | Dale et al. |
| 5,861,245 A | 1/1999 | McClelland et al. |
| 5,871,928 A | 2/1999 | Fodor et al. |
| 5,874,219 A | 2/1999 | Rava et al. |
| 5,876,924 A | 3/1999 | Zhang et al. |
| 5,888,740 A | 3/1999 | Han |
| 5,898,071 A | 4/1999 | Hawkins |
| 5,902,723 A | 5/1999 | Dower et al. |
| 5,936,324 A | 8/1999 | Montagu |
| 5,952,170 A | 9/1999 | Stroun et al. |
| 5,981,956 A | 11/1999 | Stern |
| 6,025,601 A | 2/2000 | Trulson et al. |
| 6,027,889 A | 2/2000 | Barany et al. |
| 6,045,996 A | 4/2000 | Cronin et al. |
| 6,054,564 A | 4/2000 | Barany et al. |
| 6,063,603 A | 5/2000 | Davey et al. |
| 6,090,555 A | 7/2000 | Fiekowsky et al. |
| 6,136,229 A | 10/2000 | Cui et al. |
| 6,141,096 A | 10/2000 | Stern et al. |
| 6,143,495 A * | 11/2000 | Lizardi ............... C12Q 1/6804 435/6.12 |
| 6,156,504 A | 12/2000 | Gocke et al. |
| 6,185,030 B1 | 2/2001 | Overbeck |
| 6,201,639 B1 | 3/2001 | Overbeck |
| 6,210,891 B1 | 4/2001 | Nyren et al. |
| 6,218,803 B1 | 4/2001 | Montagu et al. |
| 6,225,625 B1 | 5/2001 | Pirrung et al. |
| 6,258,540 B1 | 7/2001 | Lo et al. |
| 6,268,148 B1 | 7/2001 | Barany et al. |
| 6,309,824 B1 | 10/2001 | Drmanac |
| 6,310,199 B1 | 10/2001 | Smith et al. |
| 6,312,892 B1 | 11/2001 | Barany et al. |
| 6,329,179 B1 | 12/2001 | Kopreski |
| 6,342,387 B1 | 1/2002 | Hayashizaki et al. |
| 6,386,749 B1 | 5/2002 | Watts et al. |
| 6,391,623 B1 | 5/2002 | Besemer et al. |
| 6,401,267 B1 | 6/2002 | Drmanac |
| 6,410,276 B1 | 6/2002 | Burg et al. |
| 6,506,594 B1 | 1/2003 | Barany et al. |
| 6,534,262 B1 | 3/2003 | McKernan et al. |
| 6,534,293 B1 | 3/2003 | Barany et al. |
| 6,562,573 B2 | 5/2003 | Halaka |
| 6,573,103 B1 | 6/2003 | Wald |
| 6,576,453 B2 | 6/2003 | Barany et al. |
| 6,797,470 B2 | 9/2004 | Barany et al. |
| 6,828,100 B1 | 12/2004 | Ronghi |
| 6,833,246 B2 | 12/2004 | Balasubramanian |
| 6,852,487 B1 | 2/2005 | Barany et al. |
| 6,858,412 B2 | 2/2005 | Willis et al. |
| 6,864,052 B1 | 3/2005 | Drmanac et al. |
| 6,911,345 B2 | 6/2005 | Quake et al. |
| 6,914,137 B2 | 7/2005 | Baker |
| 6,927,028 B2 | 8/2005 | Dennis et al. |
| 6,949,370 B1 | 9/2005 | Barany et al. |
| 6,977,162 B2 | 12/2005 | Barany et al. |
| 7,014,994 B1 | 3/2006 | Barany et al. |
| 7,083,917 B2 | 8/2006 | Barany et al. |
| 7,097,980 B2 | 8/2006 | Barany et al. |
| 7,166,434 B2 | 1/2007 | Barany et al. |
| 7,198,894 B2 | 4/2007 | Barany et al. |
| 7,208,274 B2 | 4/2007 | Dhallan |
| 7,232,656 B2 | 6/2007 | Balasubramanian |
| 7,244,233 B2 | 7/2007 | Krantz et al. |
| 7,244,831 B2 | 7/2007 | Barany et al. |
| 7,312,039 B2 | 12/2007 | Barany et al. |
| 7,315,787 B2 | 1/2008 | Orlandi et al. |
| 7,320,865 B2 | 1/2008 | Barany et al. |
| 7,332,277 B2 | 2/2008 | Dhallan |
| 7,332,285 B2 | 2/2008 | Barany et al. |
| 7,343,190 B2 | 3/2008 | Krantz et al. |
| 7,358,048 B2 | 4/2008 | Krantz et al. |
| 7,364,858 B2 | 4/2008 | Barany et al. |
| 7,429,453 B2 | 9/2008 | Barany et al. |
| 7,442,506 B2 | 10/2008 | Dhallan |
| 7,455,965 B2 | 11/2008 | Barany et al. |
| 7,459,311 B2 | 12/2008 | Nyren et al. |
| 7,527,929 B2 | 5/2009 | McKernan et al. |
| 7,556,924 B2 | 7/2009 | Barany et al. |
| 7,582,420 B2 | 9/2009 | Oliphant et al. |
| 7,598,060 B2 | 10/2009 | Dhallan |
| 7,601,491 B2 | 10/2009 | Collis et al. |
| 7,622,281 B2 | 11/2009 | Ronaghi et al. |
| 7,645,576 B2 | 1/2010 | Lo et al. |
| 7,648,824 B2 | 1/2010 | Nyren et al. |
| 7,700,323 B2 | 4/2010 | Willis et al. |
| 7,709,194 B2 | 5/2010 | Lo et al. |
| 7,709,201 B2 | 5/2010 | Barany et al. |
| 7,718,367 B2 | 5/2010 | Lo et al. |
| 7,718,370 B2 | 5/2010 | Dhallan |
| 7,727,720 B2 | 6/2010 | Dhallan |
| 7,727,727 B2 | 6/2010 | Collis |
| 7,754,428 B2 | 7/2010 | Lo et al. |
| 7,780,600 B2 | 8/2010 | Krantz et al. |
| 7,799,531 B2 | 9/2010 | Mitchell et al. |
| 7,807,431 B2 | 10/2010 | Barany et al. |
| 7,888,017 B2 | 2/2011 | Quake et al. |
| 7,901,884 B2 | 3/2011 | Lo et al. |
| 7,989,614 B2 | 8/2011 | Deggerdal et al. |
| 8,008,018 B2 | 8/2011 | Quake et al. |
| 8,195,415 B2 | 6/2012 | Fan et al. |
| 8,296,076 B2 | 10/2012 | Fan et al. |
| 8,318,430 B2 | 11/2012 | Chuu et al. |
| 8,700,338 B2 | 4/2014 | Oliphant et al. |
| 8,756,020 B2 | 6/2014 | Struble et al. |
| 9,567,639 B2 | 2/2017 | Oliphant et al. |
| 2001/0051341 A1 | 12/2001 | Lo et al. |
| 2002/0045176 A1 | 4/2002 | Lo et al. |
| 2002/0132241 A1 | 9/2002 | Fan et al. |
| 2002/0160361 A1 | 10/2002 | Loehrlein et al. |
| 2003/0003459 A1 | 1/2003 | Stahl |
| 2003/0044388 A1 | 3/2003 | Dennis et al. |
| 2003/0054386 A1 | 3/2003 | Antonarakis et al. |
| 2003/0064366 A1 | 4/2003 | Hardin et al. |
| 2003/0108913 A1 | 6/2003 | Schouten |
| 2003/0143599 A1 | 7/2003 | Makarov et al. |
| 2004/0009518 A1 | 1/2004 | Lo et al. |
| 2004/0086864 A1 * | 5/2004 | Lo ................ C12Q 1/6883 435/6.18 |
| 2004/0101835 A1 | 5/2004 | Willis et al. |
| 2004/0137470 A1 | 7/2004 | Dhallan |
| 2004/0203037 A1 | 10/2004 | Lo et al. |
| 2004/0214175 A9 | 10/2004 | McKernan et al. |
| 2005/0095618 A1 | 5/2005 | Tsuio et al. |
| 2005/0100939 A1 | 5/2005 | Namsaraev et al. |
| 2005/0191656 A1 | 9/2005 | Drmanac et al. |
| 2006/0121452 A1 | 6/2006 | Dhallan |
| 2006/0204495 A1 * | 9/2006 | Zang ................ A61K 39/0008 424/140.1 |
| 2006/0252068 A1 | 11/2006 | Lo et al. |
| 2006/0252071 A1 | 11/2006 | Lo et al. |
| 2006/0275789 A1 | 12/2006 | Willis et al. |
| 2007/0087345 A1 | 4/2007 | Olson-Munoz et al. |
| 2007/0172873 A1 | 7/2007 | Brenner et al. |
| 2007/0178478 A1 | 8/2007 | Dhallan |
| 2007/0207482 A1 | 9/2007 | Church et al. |
| 2007/0275402 A1 | 11/2007 | Lo et al. |
| 2008/0020390 A1 | 1/2008 | Mitchell et al. |

(56) References Cited

U.S. PATENT DOCUMENTS

| | | |
|---|---|---|
| 2008/0081338 A1 | 4/2008 | Lo et al. |
| 2008/0090239 A1 | 4/2008 | Shoemaker et al. |
| 2008/0096766 A1 | 4/2008 | Lee |
| 2008/0243398 A1 | 4/2008 | Lo et al. |
| 2008/0138809 A1 | 6/2008 | Kapur et al. |
| 2008/0206749 A1 | 8/2008 | Lo et al. |
| 2009/0018024 A1 | 1/2009 | Church et al. |
| 2009/0029377 A1 | 1/2009 | Lo et al. |
| 2009/0048124 A1 | 2/2009 | Leamon et al. |
| 2009/0061425 A1 | 3/2009 | Lo et al. |
| 2009/0087847 A1 | 4/2009 | Lo et al. |
| 2009/0099041 A1 | 4/2009 | Church et al. |
| 2009/0155776 A1 | 6/2009 | Lo et al. |
| 2010/0105049 A1 | 4/2010 | Ehrich et al. |
| 2010/0105052 A1 | 4/2010 | Drmanac et al. |
| 2010/0112575 A1 | 5/2010 | Fan |
| 2010/0112590 A1 | 5/2010 | Lo et al. |
| 2010/0120076 A1 | 5/2010 | Braun et al. |
| 2010/0136529 A1 | 6/2010 | Shoemaker et al. |
| 2010/0184043 A1 | 7/2010 | Mitchell et al. |
| 2010/0184044 A1 | 7/2010 | Mitchell et al. |
| 2010/0184210 A1 | 7/2010 | Rossmanith et al. |
| 2010/0267034 A1 | 10/2010 | Lo et al. |
| 2010/0291571 A1 | 11/2010 | Stoughton et al. |
| 2010/0291572 A1 | 11/2010 | Stoughton et al. |
| 2011/0003293 A1 | 1/2011 | Stoughton et al. |
| 2011/0027771 A1 | 2/2011 | Deng |
| 2011/0039724 A1 | 2/2011 | Lo et al. |
| 2011/0059451 A1 | 3/2011 | Mitchell et al. |
| 2011/0086357 A1 | 4/2011 | Lo et al. |
| 2011/0105353 A1 | 5/2011 | Lo et al. |
| 2011/0117548 A1 | 5/2011 | Mitchell et al. |
| 2011/0124518 A1 | 5/2011 | Cantor |
| 2011/0143342 A1 | 6/2011 | Lo et al. |
| 2011/0151442 A1 | 6/2011 | Fan et al. |
| 2011/0171638 A1 | 7/2011 | Stoughton et al. |
| 2011/0172111 A1 | 7/2011 | Cantor |
| 2011/0177517 A1 | 7/2011 | Rava et al. |
| 2011/0178719 A1 | 7/2011 | Rabinowitz |
| 2011/0183330 A1 | 7/2011 | Lo et al. |
| 2011/0201507 A1 | 8/2011 | Rava et al. |
| 2011/0224087 A1 | 9/2011 | Quake et al. |
| 2011/0230358 A1 | 9/2011 | Rava et al. |
| 2011/0245085 A1 | 10/2011 | Rava et al. |
| 2011/0276277 A1 | 11/2011 | Lo et al. |
| 2011/0288780 A1 | 11/2011 | Rabinowitz |
| 2011/0312503 A1 | 12/2011 | Chuu |
| 2012/0003650 A1 | 1/2012 | Lo et al. |
| 2012/0010085 A1 | 1/2012 | Rava |
| 2012/0034603 A1 | 2/2012 | Oliphant et al. |
| 2012/0034685 A1 | 2/2012 | Sparks et al. |
| 2012/0040859 A1 | 2/2012 | Sparks et al. |
| 2012/0100548 A1 | 4/2012 | Rava et al. |
| 2012/0108460 A1 | 5/2012 | Quake et al. |
| 2012/0165203 A1 | 6/2012 | Quake et al. |
| 2012/0184449 A1 | 7/2012 | Hixson |
| 2012/0190557 A1 | 7/2012 | Oliphant et al. |
| 2012/0191358 A1 | 7/2012 | Oliphant et al. |
| 2012/0191367 A1 | 7/2012 | Stuelpnagel et al. |
| 2012/0219950 A1 | 8/2012 | Oliphant et al. |
| 2012/0225798 A1 | 9/2012 | Cantor et al. |
| 2012/0237928 A1 | 9/2012 | Rava et al. |
| 2012/0264115 A1 | 10/2012 | Rava |
| 2012/0264121 A1 | 10/2012 | Rava et al. |
| 2012/0270739 A1 | 10/2012 | Rava et al. |
| 2013/0029852 A1 | 1/2013 | Rava et al. |
| 2013/0040375 A1 | 2/2013 | Sparks et al. |
| 2013/0089863 A1 | 4/2013 | Oliphant et al. |
| 2013/0122500 A1 | 5/2013 | Sparks et al. |
| 2013/0172211 A1 | 7/2013 | Oliphant et al. |
| 2013/0172212 A1 | 7/2013 | Oliphant et al. |
| 2013/0172213 A1 | 7/2013 | Oliphant et al. |
| 2013/0210640 A1 | 8/2013 | Sparks et al. |
| 2013/0288244 A1 | 10/2013 | Deciu et al. |
| 2013/0288252 A1 | 10/2013 | Sparks et al. |
| 2014/0024538 A1 | 1/2014 | Zahn et al. |
| 2014/0342940 A1 | 11/2014 | Oliphant et al. |
| 2016/0002729 A1 | 1/2016 | Oliphant et al. |
| 2017/0145510 A1 | 5/2017 | Oliphant et al. |

FOREIGN PATENT DOCUMENTS

| | | |
|---|---|---|
| GB | 2299166 B | 9/1996 |
| WO | WO-87/006270 A1 | 10/1987 |
| WO | WO-90/06995 A1 | 6/1990 |
| WO | WO-98/39474 A1 | 9/1998 |
| WO | WO-99/47964 A1 | 9/1999 |
| WO | WO-00/04193 A1 | 1/2000 |
| WO | WO-00/56927 A2 | 9/2000 |
| WO | WO-00/56927 A3 | 9/2000 |
| WO | WO-2003/038120 A2 | 5/2003 |
| WO | WO-2003/038120 A3 | 5/2003 |
| WO | WO-2007/100243 A1 | 9/2007 |
| WO | WO-2007/126377 A1 | 11/2007 |
| WO | WO-2008/118998 A2 | 10/2008 |
| WO | WO-2008/118998 A3 | 10/2008 |
| WO | WO-2009-036525 A2 | 3/2009 |
| WO | WO-2009-036525 A3 | 3/2009 |
| WO | WO-2009/102632 A2 | 8/2009 |
| WO | WO-2009/102632 A3 | 8/2009 |
| WO | WO-2011/066476 A1 | 6/2011 |
| WO | WO-2011/066476 A8 | 6/2011 |
| WO | WO-2011/090556 A1 | 7/2011 |
| WO | WO-2011/090557 A1 | 7/2011 |
| WO | WO-2011/090558 A1 | 7/2011 |
| WO | WO-2012/019187 A2 | 2/2012 |
| WO | WO-2012/019187 A3 | 2/2012 |
| WO | WO-2012/019193 A2 | 2/2012 |
| WO | WO-2012/019193 A3 | 2/2012 |
| WO | WO-2012/019200 A2 | 2/2012 |
| WO | WO-2012/019200 A3 | 2/2012 |
| WO | WO-2012/088456 A2 | 6/2012 |
| WO | WO-2012/088456 A3 | 6/2012 |
| WO | WO-2012/102945 A1 | 8/2012 |
| WO | WO-2012/103031 A2 | 8/2012 |
| WO | WO-2012/103031 A3 | 8/2012 |
| WO | WO-2013/009175 A1 | 1/2013 |
| WO | WO-2013/192292 A1 | 12/2013 |
| WO | WO-2016/018986 A1 | 2/2016 |

OTHER PUBLICATIONS

Myllykangas et al. Biotechnol Genet Eng Rev. 2010. 27:135-138.*
Turner et al. Nat. Methods. 2009. 6(5):315-316.*
Shea et al. Clinical Chemistry. 2013. 59(8):1151-1159.*
Koumbaris et al. Clinical Chemistry. 2016. 62(6):848-855.*
Abadia-Molina, et al., "Immune phenotype and cytotoxic activity of lymploycytes from human term decidua against trophoblast", J. of Reproductive Immunology, n31:109-23 (1996).
Advisory Action dated Jan. 29, 2013 for U.S. Appl. No. 13/293,419 (inventor A. Sparks, filed Nov. 10, 2011), entire document.
Agostini, et al., "Circulating cell-free DNA: a promising marker of pathologic tumor response in rectal cancer patients receiving pre-operative chemotherapy", Ann. Surg. Oncol., 18(9):2461-68 (2011).
Alexandrov, et al., "Definition of a new alpha satellite suprachromosomal family characterized by monomeric organization", Nucleic Acids Research, 21(9):2209-15 (2003).
Anker, et al., Information carried by the DNA release by antigen-stimulated lymphocytes:, Immunology, 37:753-63 (1979).
Anker, et al., "K-ras Mutations are found in DNA extracted from the plasma of patients with colorectal cancer," Gastroenterology, 112:1114-20 (1997).
Anker, et al., "Spontaneous Release of DNA by Human Blood Lymphocytes as Shown in an in Vitro System", Cancer Research, 35:2375-82 (1975).
Arnheim, et al., "Molecular evidence for genetic exchanges among ribosomal genes on nonhomologous chromosomes in man and apes", PNAS USA, 77(12):7323-27 (1980).
Ashoor, et al., "Chromosome-selective sequencing of maternal plasma cell-free DNA for first-trimester detection of trisomy 21 and trisomy 18", Am. J. of Obstet. Gynecol., (2012), doi: 10.1016/j.ajog.2012.01.029.

(56) References Cited

OTHER PUBLICATIONS

Ashoor, et al., Fetal Fraction in Maternal Plasma Cell-Free DNA at 11-13 Weeks' Gestation: Effect of Maternal and Fetal Factors, Fetal Dian Ther D01:10.1159/000337373 (Pub'd online May 4, 2012).
Australian Patent Examination Report No. 1 dated Feb. 20, 2014 for 2011285512, entire document.
Australian Patent Examination Report No. 1 dated Feb. 7, 2014 for 2011285477, entire document.
Australian Patent Examination Report No. 1 dated Mar. 4, 2014 for 2011285518, entire document.
Avent, N.D. (2008). "RHD genotyping from maternal plasma: guidelines and technical challenges," Methods in Molecular Biology 444:185-201.
Bandyopadhyay, et al, "Identification and characterization of satellite III subfamilies to the acrocentric chromosomes", Chromosome Research, 9:223-33 (2001).
Batzer and Deininger, "ALU Repeats and Human Genomic Diversity", Nature, 3:370-79 (2002).
Beard, "Embryological Aspects and Etiology of Carcinoma", The Lancet, Jun. 21, 1902, pp. 1758-1761.
Belokhvostov, et al., "Changes in the Fractional Composition of the Nucleic Acids in Blood Serum upon Radiation Damage Early Stage Abnormalities Following Gamma-Irradiation of Rats", Tsitologiia (Cytology) 1986.
Bianchi, "Isolation of fetal DNA from nucleated erythrocytes in maternal blood", PNAS USA, 87:3279-83 (1990).
Bianchi, "PCR Quantitation of Fetal Cells in Maternal Blood in Normal and Aneuploid Pregnancies", Am J. Hum. Genet., 61:822-29 (1997).
Bianchi, "Prenatal diagnosis by analysis of fetal cells in maternal blood", J. of Pediatrics, 127(6):847-56 (1995).
Bianchi, et al., "Large Amounts of Cell-free DNAS Are Present in Amniotic Fluid", Clin. Chem., 47(10) 1867-69 (2001).
Biran, "On the Oncodevelopmental Rold of Human Imprinted Genes", 43:119-23 (1994).
Blaschke and Rappold, "The Pseudoautosomal regions, SHOX and disease", Curr. Opin. Gene. Dev., 16(3):23-29 (2006).
Bodurtha and Strauss, "Genomics and Prenatal Care", New Eng. J. of Medicine, 366:64-73 (2012).
Bombard, et al., "Fetal RHD genotype detection from circulating cell-free DNA in maternal plasma in non-sensitized RhD negative women", Prenat Diagn, 31:802-08 (2011).
Bradstock, et al., "Functional and phenotypic assessment of neonatal human leucocytes expressing natural killer cell-associated antigen", Immunology and Cell Biology (71:535-42 (1993).
Camaschella, et al., "Prenatal Diagnosis of Fetal Hemoglobin Lepore-Boston Disease on Maternal Peripheral Blood", Blood, 75(11):2102-06 (1990).
Campbell, et al., "Subclonal phylogenetic structions in cancer revealed by ultra-deep sequencing", PNAS, 105(35):13081-86 (2008).
Cappuzzo, et al., "Epidermal growth factor receptor gene and protein and gefitinib sensitivity in non-small-cell lung cancer", J. Nati Cancer Inst., 97(9):643-55 (2005).
Centre for Genomics Education, "Changes to Chromosome Structure—Translocations", The Australasian Genetics Resource Book, www.aenetics com, pp. 1-5 (2007).
Chen, et al., "Microsatellite alterations in plasma DNA of small cell lung cancer patients", Nature Medicine, 2(9):1033-35 (1996).
Chen, et al., "Noninvasive prenatal diagnosis of fetal trisomy 18 and trisomy 13 by maternal plasma DNA sequencing", PLos One, 6:e21791 (2011).
Chim, et al., "Detection of the placental epigenetic signature of the maspin gene in maternal plasma", PNAS USA, 102(41):14753-58 (2005).
Chiu and Lo, "Non-invasive prenatal diagnosis by fetal nucleic acid analysis in maternal plasma: the coming of age", Semin. Fetal Neonatal Med., 16(2):88-93 (2011).
Chiu, et al, "Effects of Blood-Processing Protocols on Fetal and Total DNA Quantification in Maternal Plasma", Clin. Chem., 47(9):1607-1613 (2001).
Chiu, et al, "Noninvasive prenatal diagnosis of fetal chromosomal aneuploidy by massively parallel genomic sequencing of DNA in maternal plasma", PNAS USA 105:20458-63 (2008), 17 pages supporting information.
Chiu, et al., "Maternal plasma DNA analysis with massively parallel sequencing by ligation for noninvasive prenatal diagnosis of trisomy 21", Clinical Chemistry 56:459-63 (2010).
Chiu, et al., "Non-invasive prenatal assessment of trisomy 21 by multiplexed maternal plasma DNA sequencing: large scale validity study", Br Med J. 342:c7401 (2011).
Chiu, et al., "Non-invasive prenatal diagnosis by single molecule counting technologies", Trends in Genomics, 25(7):324-31 (2009).
Choo, et al., "A Chromosome 14-specific Human Satellite III DNA Subfamily That Shows Variable Presence on Different Chromosomes 14", Am J. Hum. Genet., 50:706-16 (1992).
Choo, et al., "A homologous subfamily of satellite III DNA on human chromosomes 14 and 22", Nucleic Acids Research, 18(19):5641-47 (1990).
Chromosome 14 map, Nature 409:947-48 (2001).
Chu, et al., "A novel approach toward the challenge of accurately quantifying fetal DNA in maternal plasma", Prenat. Diag., 30:1226-29 (2010).
Ciccodicola, et al., "Differentially regulated and evolved genes in the fully sequences Xq/Yq pseudoautosomal region", Hum. Mol. Genet., 9(3):395-401 (2000).
Cicuttini and Boyd, "Hemopoietic and Lymphoid Progenitro Cells in Human Umbilical Cord Blood", Developmental Immunology, 4:1-11 (1994).
Cirigiliano, et al., "Clinical application of multiplex quantitative fluorescent polymerase chain reaction QF-PCR for the repaid prenatal detection of common chromosome aneuploidies", Molecular Human Reproduction, 7(10):1001-06 (2001).
Cirigiliano, et al., "Rapid prenatal diagnosis of common chromosome aneuploidies by QF-PCR, results of 9 years of clinical experience", Prenatal diagnosis, 29:40-49 (2009).
Cockwell, et al., "Distribution of the D15A1 copy number polymorphism", European J. of Hum. Genet., 15:441-45 (2007).
Conover, Practical Nonparametric Statistics, pp. 295-01 (John Wiley & Sons, NY)(1971).
Costa, et al., "New strategy for prenatal diagnosis of X-linked disorders", N. Engl J. Med., 346:1502 (2002).
Datta, et al., "Sensitive Detection of Occult Breast Cancer by the Reverse-Transcriptase Polymerase Chain Reaction", J. of Clinical Oncology, 12(3): 475-82 (1994).
Dear, et al., "A High-Resolution Metric Happy Map of Human Chromosome 14" Genmoics, 48 232-41 (1998).
Dennin, "DNA of Free and Complexed Origin in Human Plasma: Concentration and Length Distribution", Klin. Wochenschr., 57:451-56 (1979).
Dhallan, et al., "A non-invasive test for prenatal diagnosis based on fetal DNA present in maternal blood: a preliminary study", Lancet, 369(9560):474-81 (2007).
Dobrzycka, et al., "Circulating free DNA and p53 antibodies in plasma of patients with ovarian epithelial cancers", Annals of Oncology, 22:1133-40 (2011).
Dobrzycka, et al., "Prognostic significance of VEGF and its receptors in endometrioid endometrial cancer", Ginekol Pol. 81(6):422-25 (2010).
Duan, et al., "PstSNP-HapMap3: a database of SNPs with high population differentiation for HapMap3", Bioinformation, 3(3):139-41 (2008).
Earle, et al., "Identification of DNA Sequences Flanking the Breakpoin of Human t(14q21q) Robertsonian Translocations", Am J. Hum Genet., 50:717-24 (1992).
Ehrich, et al., "Noninvasive detection of fetal trisomy 21 by sequencing of fetal DNA in maternal blood: a study in a clinical setting", AM J. Obstet Gynecol, 2011:204:205 el-11 (2011).
Enders, et al., "Fetal morbidity and mortality after acute human parvovirus B19 infection in pregnancy: prospective evaluation of 1018 cases", Prenatal Diagnosis, 24:513-18 (2004).
EPO Examination Report dated Nov. 21, 2013 for App. No. 11745880.2, entire document.

(56) References Cited

OTHER PUBLICATIONS

EPO Examination Report dated Nov. 21, 2013 for App. No. 11745881. 1, entire document.
EPO Examination Report dated Nov. 28, 2013 for App. No. 11745883. 6, entire document.
Fan, et al., "Analysis of the Size Distributions of Fetal and Maternal Cell-Free DNA by Paired-End Sequencing", Clin. Chem., 56(8):1279-80 (2010).
Fan, et al., "Noninvasive diagnosis of fetal aneuploidy by shotgun sequencing DNA from maternal blood", PNAS USA, 105(42):16266-71 (2008).
Fan, et al., "Sensitivity of noninvasive prenatal detection of fetal aneuploidy from maternal plasma using shotgun sequencing is limited only by counting statistics", PLoS One, 5:e10439 (2010).
Fejgin, et al., "Fetal cells in the uterine cervix: a source for early non-invasive prenatal diagnosis", Prenat. Diag., 21:619-21 (2001).
Final Office Action Received on Jul. 8, 2013 for U.S. Appl. No. 13/689,206 (inventor A. Oliphant, filed Nov. 39, 2012), entire document.
Final Office Action Received on Oct. 12, 2012 for U.S. Appl. No. 13/293,419 (inventor A. Sparks, filed Nov. 10, 2011), entire document.
Finning, et al., "Effect of high throughput RHD typing of fetal DNA in maternal plasma on use of anti-RhD immunoglobulin in RhD negative pregnant women: prospective feasibility study", Br Med J., 336:816-18 (2008).
Fisher, et al., "Genetic evidence that placental site trophoblastic tumours can originate from a hydatidiform mole or a normal conceptus", Br. J. Cancer, 65:355-58 (1992).
Fournie, et al., "Plasma DNA as Cell Death Marker in Elderly Patients", Gerontology, 39:215-221 (1993).
Fowke, Genetic analysis of human DNA recovered from minute amounts of serum and plasma, J. of Immunol. Meth., 180:45-51 (1995).
Geifman-Holzman, et al., "Fetal RhD genotyping in fetal cells flow sorted from maternal blood", Am. J.Obstet. Gynecol., 174(3):818-22 (1996).
Ghossein, et al.. "Detection of Circulating Tumor Cells in Patients With Localized and Metastatic Prostatic Carcinoma Clinical Implications", J. of Clin. Oncology, 13(5):1995-200 (1995).
Gold, "Cancer and Pregnancy: Parallels in Growth, Invasion, and Immune Modulation and Implicationsa for Cancer Therapeutic Agents", Mayo Clin. Proc., 84(11):985-1000 (2009).
Gosden, et al., "Satellite DNA Sequences in the Human Acrocentric Chromosomes: Information from Translocations and Heteromorphisms", Am. J. Hum. Genet., 33:243-51 (1981).
Greeley, et al., "Get ready for the flood of fetal gene screening", Nature, 469:289-91 (2011).
Green, et al., "Gestational Trophoblastic Disease: A Spectrum of Radiologic Diagnosis", Radiographics, 16(6):1371-84 (1996).
Gribben, et al., "Detection of Residual Lymphoma Cells by Polymerase Chain Reaction in Peripheral Blood is Significantly Less Predictive for Relapse Than Detection in Bone Marrow", Blood, 83(12):3800-07 (1994).
Guatelli, et al., "Isothermal, in vitro amplification of nucleic acids by a multienzyme reaction modeled after retroviral replication", PNAS USA, 87(5):1874-(1990).
Han, et al, "Molecular Chytogenetic Characterization of 17 rob(13q14q) Robertsonian Translocations by Fish, Narrowing the Region Containing the Breakpoints", Am J. Hum. Genet., 55:960-67 (1994).
Hardenbol et al., Multiplexed genotyping with sequence-tagged molecular inversion probes. Nat Biotechnol. Jun. 2003;21(6):673-8.
Hardingham, et al., "Detection of Circulating Tumor Cells in Colorectal Cancer by Immunogead-PCR is a Sensitive Prognostic marker for Relapse of Disease", Molecular Medicine, 1(7):789-94 (1995).
Harrell, Regression modeling strategies, §§9.2.2 and 1.10.5 (Springer Vertag)(2001).
Hayden, et al., "Multiplex-Ready PCR: A new method for multiplexed SSR and SNP genotyping", BMC Genomics, 9:80:1-12 (2007).
Heid, et al., "Real Time Quantitative PCR", Genome Res., 6:986-94 (1996).
Heilig, et al., "The DNA sequence and analysis of human chromosome 14", Nature, 421:601-09 (2003).
Ho, et al., "Activation Status of T and NK Cells in the Endometrium Throughout Menstrual Cycle and Normal and Abnormal Early Pregnancy", Human Immunology, 49:130-36 (1996).
Hoon, et al., "Detection of Occult Melanoma Cells in Blood With a Multiple-Marker Polymerase Chain Reaction Assay", J. of Clinical Oncology, 13(8):2109-116 (1995).
Hosny, et al., "TP53 mutations in circulating fee DNA from Egyptian patients with non-Hodgkin's lymphoma", Cancer Lett., 275(2):234-39 (2009).
Hsuih, et al., "Novel, ligation-depdent PCR assay for detection of hepatitis C in serum", J. of Clin. Microbiology, 34(3):501-07 (1996).
Huang, et al., "Identification of a family of alternatively splied mRNA species of angiopoietin-1", Blood, 95:1993-99 (2000).
Indolfi, et al., "Perinatal Transmission of Hepatitis C Virus Infection", J. Med. Virol., 81:836-43 (2009).
International Human Genome Sequencing Consortium, "Initial sequencing and analysis of the human genome", Nature, 409:860-921 (2001).
Irizarry, et al., "Summaries of Affymetrix GeneChip probe level data", Nuc. Acid Res., 31(4):e5 (2003).
Jiang, et al., Noninvasive Fetal Trisomy (NIFTY) test: an advanced noninvasive prenatal diagnosis methodology for fetal autosomal and sex chromosomal aneuploidies. BMC Med Genomics. Dec. 1, 2012;5:57.
Kamnasaran and Cox, "Current status of chromosome 14", J. Med. Genet., 39:81-90 (2002).
Kazakov, et al., "Extracellular DNA in the Blood of Pregnant Women", Tsitologiia (Cytology), 37(3):232-37 (1995).
Kogan, et al., "An improved method for prenatal diagnosis ofgenetic diseases by analysis of amplified DNA sequences", New England J. of Medicine, 317(6):985-90 (1987).
Krebs, et al., "The Unitarian or Trophoblastic Thesis of Cancer" Medical Record, 163:149-74 (Jul. 1950).
Landegren, et al., "A ligase-mediated gene detection technique", Science, 241:1077 (1988).
Lapair, et al., "Cell-Free DNA in Amniotic Fluid: Unique Fragmentation Signatures in Euploid and Aneuploid Fetuses", Clinical Chem., 53(3):405-11 (2007).
Leon, "Free DNA in the Serum of Cancer Patients and the Effect of Therapy", Cancer Res., 37:646-50 (1977).
Li, et al., "A photocleavable fluorescent nucleotide for DNA sequencing and analysis", PNAS USA, 100(2):414-19 (2003).
Liao, et al., "Targeted massively parallel sequencing of maternal plasma DNA permits efficient and unbiased detection of fetal alleles", Clin Che, 57:92-101 (2011).
Lo, "Fetal nucleic acids in maternal blood: the promises", Clin. Chem. Lab Med., 50(5):xxx-xxxx (DOI 10.1515/CCLM.2011.765) (2011).
Lo, et al., "Detection of single-copy fetal DNA sequence from maternal blood", The Lancet, 335:1463-64 (1990).
Lo, et al., "Digital PCR for the molecular detection of fetal chromosomal aneuploidy", PNAS USA, 104:13116-21 (2007).
Lo, et al., Maternal plasma DNA sequencing reveals the genome-wide genetic and mutational profile of the fetus. Sci Transl Med, 2:61ra91 (2010).
Lo, et al., "Plasma placental RNA allelic ratio permits noninvasive prenatal chromosomal aneuploidy detection", Nat. Med., 13:218-23 (2007).
Lo, et al., "Prenatal diagnosis of fetal RhD status by molecular analysis of maternal plasma", N Engl J Med, 339:1734-38 (1998).
Lo, et al., "Presence of fetal DNA in maternal plasma and serum", The Lancet, 350:485-86 (1997).
Lo, et al., "Quantitative analysis of fetal DNA in maternal plasma and serum: implications for noninvasive prenatal diagnosis", Am J. Hum. Genetics, 62:768-75 (1998).

(56) References Cited

OTHER PUBLICATIONS

Lo, et al., "Rapid clearance of fetal DNA from maternal plasma", AM J. Hum. Genetics, 64:218-24 (1999).
Lo, et al., "Two-way cell traffic between mother and fetus: biological and clinical implications", Blood, 88:4390-95 (1996).
Lun, et al., "Microfluidics Digital PCR Reveals a Higher than Expected Fraction of Fetal DNA in Maternal Plasma", Clin. Chem., 54(10):1664-72 (2008).
Lun, et al., "Noninvasive prenatal diagnosis of monogenic diseases by digital size selection and relative mutation dosage on DNA in maternal plasma", PNAS USA, 105(50):19920-25 (2008).
Makrigiorgos, et al., "A PCR-based amplification method retaining the quantitative difference between two complex genomes", Nat. Biotech., 20:936-39 (2002).
Mangs, Curr. Genomics, "The Human Pseudoautosomal Region (PAR): Origin, Function and Future", 8(2):129-36 (2007).
Mansfield, "Diagnosis of Down syndrome and other aneuploidies using quantitative polymerase chain reaction and small tandem repeat polymorphisms", Human Molecular Genetics, 2(1):43-50 (1993).
Mantzaris, et al., "Preliminary report: correct diagnosis of sex in fetal cells isolated from cervical mucus during early pregnancy", ANZJOG, 45(6):529-32 (2005).
Mardis, et al., "The impact of next-generation sequencing technology on genetics", Trends in Genetics, 24(3):133-41 (2007).
Margulies, et al., "Genome sequencing in microfabricated high-density picolitre reactors", Nature, 437(15):376-80 and errata (2005).
Mikhaylov, et al., "Changes in the quantity and synthesis of DNA in the nuclei of large decidual cells of rats in the course of their differentiation", Tsitologia (Cytology), 41(6):677-83 (1992).
Mikhaylov, et al., "Synthesis and content of DNA in human decidual cells at various stages of differentiation according to flow cytometry analysis", Tsitologiia (Cytology), 34(6):67-72 (1992).
Moffet-King, et al., "Natural Killer Cells and Pregnancy", Nature Reviews Immunology, 2002(2):656-63.
Moreno and Gomella, "Circulating Prostate Cancer Cells Detected by Reverse Transcription-Polymerase Chain Reaction (RT-PCR: What do they mean?", Cancer control Journal, 5(6) (1998).
Mueller, et al., "Isolation of fetal trophoblast cells from peripheral blood of pregnant women", The Lancet, 336:197-200 (1990).
Mujezinovic and Alfirevic, Obstet. Gynecol., "Procedure-Related Complications of Amniocentesis and Chorionic Villous Sampling: A Systematic Review", 110(3):687-94 (2007).
Mulcahy, et al., "Plasma DNA K-rase Mutations in Patients with Gastrointestinal Malignancies," Annals New York Academy of Sciences, 25-28.
Nawroz, et al., "Microsatellite alterations in serum DNA of head and neck cancer patients", Nature Medicine, 2(9):1035-37 (1996).
Nelson, et al., "Alu polymerase chain reaction: A method for rapid isolation of human-specific sequence from complex DNA sources," PNAS USA, 86:6686-90 (1989).
Ng, et al., "mRNA of placental origin is readily detectable in maternal plasma", PNAS USA, 100:4748-53 (2003).
Nicolaides, et al., "Validation of targeted sequencing of single-nucleotide polymorphisms for non-invasive prenatal detection of aneuploidy of chromosomes 13, 18, 21, X and Y", Prenatal Diagnosis, 33:1-5 (2013).
Oei, et al., "Clusters of regulatory signals for RNA polymerase II transcription associated with Alu family repeats and CpG islands in human promoters", Genomics, 83:873-82 (2004).
Office Action dated Apr. 11, 2013 for U.S. Appl. No. 13/013,732 (inventor A. Oliphant, filed Jun. 25, 2011), entire document.
Office Action dated Apr. 14, 2014 for U.S. Appl. No. 13/013,732, filed Jun. 25, 2011, inventor Oliphant, entire document.
Office Action dated Apr. 15, 2013 for U.S. Appl. No. 13/356,133 (inventor A. Oliphant, filed Jan. 23, 2012), entire document.
Office Action dated Apr. 5, 2013 for U.S. Appl. No. 13/689,206 (inventor A. Oliphant, filed Nov. 19, 2012), entire document.
Office Action dated Aug. 30, 2013 for U.S. Appl. No. 13/205,570, filed Aug. 8, 2011, inventor Sparks, entire document.
Office Action dated Aug. 30, 2013 for U.S. Appl. No. 13/245,133, filed Sep. 26, 2011, inventor Oliphant, entire document.
Office Action dated Aug. 30, 2013 for U.S. Appl. No. 13/687,169, filed Nov. 28, 2012, inventor Sparks, entire document.
Office Action dated Aug. 8, 2013 for U.S. Appl. No. 13/605,505, filed Sep. 6, 2012, inventor Struble, entire document.
Office Action dated Dec. 10, 2013 for U.S. Appl. No. 13/205,490, filed Aug. 8, 2011, inventor Sparks, entire document.
Office Action dated Dec. 11, 2013 for U.S. Appl. No. 13/274,309, filed Oct. 15, 2011, inventor Struble, entire document.
Office Action dated Dec. 30, 2013 for U.S. Appl. No. 13/205,603, filed Aug. 8, 2011, inventor Sparks, entire document.
Office Action dated Dec. 7, 2012 for U.S. Appl. No. 13/013,732 (inventor A. Oliphant, filed Jun. 25, 2011), entire document.
Office Action dated Feb. 11, 2014 for U.S. Appl. No. 13/689,206, filed Nov. 29, 2012, inventor Oliphant, entire document.
Office Action dated Feb. 11, 2014 for U.S. Appl. No. 13/405,839, filed Feb. 27, 2012, inventor Oliphant, entire document.
Office Action dated Feb. 15, 2013 for U.S. Appl. No. 13/689,417 (inventor A. Oliphant, filed Nov. 29, 2012), entire document.
Office Action dated Feb. 28, 2013 for U.S. Appl. No. 13/205,570 (inventor A. Sparks, filed Aug. 8, 2011), entire document.
Office Action dated Feb. 28, 2013 for U.S. Appl. No. 13/245,133, filed Sep. 26, 2011, inventor Oliphant, entire document.
Office Action dated Jan. 31, 2014 for U.S. Appl. No. 13/605,505, filed Sep. 6, 2012, inventor Struble, entire document.
Office Action dated Jul. 14, 2014 for U.S. Appl. No. 13/293,419, filed Nov. 10, 2011, Sparks, entire document.
Office Action dated Jul. 16, 2014 for U.S. Appl. No. 13/687,025, filed Nov. 28, 2011, inventor Sparks, entire document.
Office Action dated Jul. 30, 2014 for U.S. Appl. No. 13/407,978, filed Feb. 29, 2012, inventor Song, entire document.
Office Action dated Jul. 31, 2013 for U.S. Appl. No. 13/013,732, filed Jun. 25, 2011, inventor Oliphant, entire document.
Office Action dated Jul. 5, 2012 for U.S. Appl. No. 13/013,732 (inventor A. Oliphant, filed Jun. 25, 2011).
Office Action dated Jul. 8, 2013 for U.S. Appl. No. 13/205,490, filed Aug. 8, 2011, inventor Sparks, entire document.
Office Action dated Jun. 13, 2013 for U.S. Appl. No. 13/316,154 (inventor A. Oliphant, filed Dec. 9, 2011), entire document.
Office Action dated Jun. 13, 2013 for U.S. Appl. No. 13/338,963 (inventor A. Oliphant, filed Dec. 28, 2011), entire document.
Office Action dated Jun. 25, 2014 for U.S. Appl. No. 13/689,206, filed Nov. 29, 2012, inventor Oliphant, entire document.
Office Action dated Jun. 26, 2014 for U.S. Appl. No. 13/205,603, filed Aug. 8, 2011, inventor Sparks, entire document.
Office Action dated Jun. 26, 2014 for U.S. Appl. No. 13/356,133, filed Jan. 23, 2012, inventor Oliphant, entire document.
Office Action dated Mar. 14, 2013 for U.S. Appl. No. 13/687,025 (inventor A. Sparks, filed Nov. 28, 2012), entire document.
Office Action dated Mar. 28, 2013 for U.S. Appl. No. 13/687,169 (inventor A. Sparks, filed Nov. 28, 2012), entire document.
Office Action dated May 10, 2012 for U.S. Appl. No. 13/293,419 (inventor A. Sparks, filed Nov. 10, 2011), entire document.
Office Action dated May 12, 2014 for U.S. Appl. No. 13/689,417, filed Nov. 29, 2012, inventor Oliphant, entire document.
Office Action dated May 13, 2013 for U.S. Appl. No. 13/407,978 (inventor K. Song, filed Feb. 29, 2012), entire document.
Office Action dated May 17, 2013 for U.S. Appl. No. 13/356,575 (inventor A. Oliphant, filed Jan. 23, 2012), entire document.
Office Action dated May 8, 2014 for U.S. Appl. No. 13/205,570, filed Aug. 8, 2011, inventor Sparks, entire document.
Office Action dated May 8, 2014 for U.S. Appl. No. 13/245,133, filed Sep. 26, 2011, inventor Oliphant, entire document.
Office Action dated May 8, 2014 for U.S. Appl. No. 13/687,169, filed Nov. 28, 2012, inventor Sparks, entire document.
Office Action dated Oct. 18, 2013 for U.S. Appl. No. 13/356,133, filed Jan. 23, 2012, inventor Oliphant, entire document.
Office Action dated Oct. 2, 2013 for U.S. Appl. No. 13/687,025, filed Nov. 28, 2012, inventor Sparks, entire document.
Office Action dated Oct. 25, 2013 for U.S. Appl. No. 13/407,978, filed Feb. 29, 2012, inventor Song, entire document.

(56) References Cited

OTHER PUBLICATIONS

Office Action dated Oct. 31, 2013 for U.S. Appl. No. 13/356,575 filed Jan. 23, 2012, inventor Oliphant, entire document.
Office Action dated Oct. 31, 2013, filed Dec. 9, 2011, inventor Oliphant for U.S. Appl. No. 13/316,154, entire document.
Page, et al., "Breakpoint diversity illustrates distinct mechanisms for Robertsonian translocation formation", Hum. Molec. Genet., 5(9):1279-88 (1996).
Page, et al., Br. J. Cancer, "Detection of HER2 amplification in circulating free DNA in patients with breast cancer", 104(8):1342-48 (2011).
Palomaki, et al., DNA sequencing of maternal plasma reliably identifies trisomy 18 and trisomy 13 as well as Down syndrome: an international collaborative study. Genet Med. Mar. 2012;14(3):296-305.
Paolella, et al., "The Alu family repeat promoter has a tRNA-like bipartite structure", EMBO J., 2(5):691-96 (1983).
Papageorgiou, et al., "DNA methylation ratio permits noninvasive prenatal diagnosis of trisomy 21", Nat. Med., 17:510-13 (2011).
Petersen, et al., "Down Syndrome Due to De Novo Robertsonian Translocation t(14q21q): DNA Polymorphism Analysis Suggests that the Origin of the Extra q21 is Maternal", Am. JU. Hum. Genet. 49:529-36 (1991).
Poon, et al., "Differential DNA methylation between fetus and mother as a strategy for detecting fetal DNA in maternal plasma", Clin Chem, 48:35-41 (2002).
Porreca, et al., "Multiplex amplification of large sets of human exons", Nat. Methods, 4(11):931-36 (2007).
Rijinders, et al., "Fetal sex determination from maternal plasma in pregnancies at risk for congenital adrenal hyperplasia", Obstet Gynecol, 98:374-78 (2001).
Ro, et al., "Association of Polymorphisms of Interleukin-8, CXCR1, CXCR2, and Selectin With Allograft Outcomes in Kidney Transplantation", Transplantation, 91(1):57-64 (2011).
Robbins, et al., Pathologic Basis of Disease 5th Ed., Chapter 23, pp. 1071-1088 (1994).
Ronaghi, et al., "A Sequencing Method Based on Real_Time Pyrophosphate", Science, 281:363-65 (1998).
Ross, et al., "The DNA sequence of the human X Chromosome", Nature 434:325-37 (2005).
Roth, et al., Molec. Oncol., "Screening for circulating nucleic acids and caspase activity in the peripheral blood as potential diagnostic tools in lung cancer", 5(3):281-91 (2011).
Royston, "An extension of Shapiro and Wilk's W test for normality to large samples", Applied Statistics, 31:115-24 (1982).
Royston, "Model-based screening by risk with application to Down's syndrome", Statistics in Medicine, 11(2)257-68 (1992).
Saiki, et al., "Primer-directed Enzymatic Amplification of DNA with a Thermostable DNA Polymerase", Science, 239:487-91 (1987).
Savas, "Useful genetic variation databases for oncologists investigating the genetic basis of variable treatment response and survival in cancer", Acta Oncol., 49(8):1217-26 (2010).
Schallhammer, et al., "Phenotypic comparison of natural killer cells from peripheral blood and from early pregnancy decidua", Early Pregnancy: Biology and Medicine, 3:15-22 (1997).
Schouten, et al., "Relative quantification of 40 nucleic acid sequences by multiplex ligation-dependent probe amplification", Nuc. Ac. Res., 30(12):e57 (2002).
Schroder, et al., "Transplacental passage of blood cells", J. of Medical Genetics, 12:230-42 (1974).
Schuster, et al, "Next-generation sequencing transforms today's biology", Nat. Methods, 5:16-18 (2008).
Scriven, et al., "Robertsonian translocations—reproductive reisks and indications for preimplantation genetic diagnosis", Human Reproduction, 16(11):2267-73 (2001).
Search Report dated Apr. 19, 2013 for (PCT/US2012/70177), entire document.
International Search Report dated Aug. 12, 2014 for PCT/US2013/075683, filed on Dec. 17, 2013, 5 pages.
Search Report dated Feb. 21, 2013 for (PCT/US2011/046963), entire document.
Search Report dated Jan. 20, 2012 for (PCT/US2012/21955).
Search Report dated May 10, 2012 for (PCT/US2012/026754).
Search Report dated May 11, 2012 for (PCT/US2012/022261).
Search Report dated May 14, 2013 for PCT/US 2014/17092, entire document.
Search Report dated May 2, 2012 for PCT/US2011/046935).
Search Report dated Nov. 15, 2013 for PCT/US 2013/51310, entire document.
Search Report dated Oct. 15, 2012 for (PCT/US2011/046981).
Search Report dated Sep. 12, 2013 for PCT/US 2012/026754, entire document.
Search Report dated Aug. 13, 2012 for (PCT/US2011/046976), entire document.
Sebat, et al., "Strong Association of De Novo Copy Number Mutations with Autism", Science, 316(5823):445-49 (2007).
Sehnert, et al., "Optimal detection of fetal chromosomal abnormalities by massively parallel DNA sequencing of cell-free fetal DNA from maternal blood", Clin Chem, 57: 1042-49 (2011).
Shamash, et al., "Preimplantation genetic haplotyping a new application for diagnosis of translocation carrier's embryo—preliminary observations of two robertsonian translocation carrier families", J. Assist. Reprod. Genet., 28:77-83 (2011).
Shapiro, et al., "Determination of Circulating DNA Levels in Patients with Benign or Malignant Gastrointestinal Disease", Cancer, 51:2116-20 (1983).
Shen et al. BMC Genetics. 2008. 9:27, 1-18.
Shen et al. "High-throughput SNP genotyping on universal bead arrays," Mutation Research 2005. 573:70-82.
Shendure, et al., "Accurate Multiplex Polony Sequencing of an Evolved Bacterial Genome", Science, 309:1728-32 (2005).
Simpson and Elias, "Isolating Fetal Cells from Maternal Blood", JAMA, 270(19):2357-61 (1993).
Simpson, "Is Cell-Free Fetal DNA from Maternal Blood Finally Ready for Prime Time?", Obst & Gynecol., 119(5):1-3 (2012).
Simpson, et al., "Isolating Fetal Cells in Maternal Circulation for Prenatal Diagnosis", Prenatal Diagnosis, 14:1229-42 (1994).
Smith, et al., "Quantitative phenotyping via deep barcode sequencing", Genome Res., 19:1836-42 (2009).
Smith, et al.,"Detection of melanoma cells in peripheral blood by means of reverse transcriptase and polymerase chain reaction", The Lancet, 338:1227-29 (1991).
Smith, et al.. "Placental apoptosis in normal human pregnancy", Am. J. Obstet. Gynecol, Jul. 1997, pp. 57-65.
Snyder, et al., "Universal noninvasive detection of solid organ transplant rejection", PNAS USA, 108(5):6229-34 (2011).
Sorenson, "Cancer Epidemiology, Biomarkers and Prevention", Cancer Epidem. Biomarkers Prey., 3_67-71 (1994).
Sorenson, et al., "Soluble normal and mutated DNA sequences from single-copy genes in human blood", Cancer Epidemmiol. Biomarkers, 3:64-71 (1994).
Sparks, et al., "Non-invasive prenatal detection and selective analysis of cell-free DNA obtained from maternal blood: evaluation for trisomy 21 and trisomy 18", Am. J. Obstet. Gynecol., (2012),206:319.e1-9.
Sparks, et al., "Selective analysis of cell-free DNA in maternal blood for evaluation of fetal trisomy", Prenatal Diagnosis, 32:3-9 (2012).
St. Clair, "Copy Number Variation and Schizophrenia", Schizophr. Bull., 35(1):9-12 (2009).
Stroun, et al., "Circulating Nulceic Acids in Higher Organisms", Rev. Cytol. 51:1-48 (1977).
Stroun, et al., "Isolation and Characterization of DNA from the Plasma of Cancer Patients", Eur. J. Cancer Clin. Oncol., 23(6):707-12 (1987).
Stroun, et al., "Neoplastic Characteristics of the DNA Found in the Plasma of Cancer Patients", Oncology, 46:318-322 (1989).
Stroun, et al., The Origin and Mechanism of Circulating DNA, Annals New York Academy of Sciences, 906:161-68 (2000).
Sullivan, et al., "Evidence for Structural Heterogeneity from Molecular Cytogenetic Analysis of Dicentric Robertsonian Translocations", Am. J. Hum. Genet., 59:167-75 (1996).

(56) References Cited

OTHER PUBLICATIONS

Tagle, et al., "An optimized Alu-PCR primer pair for human-specific amplification of YACs and somatic cells hybrids", Human Molecular Genetics, 1(2):121-22 (1992).
Tewhey, R. et al. (2009, e-published Nov. 1, 2009). "Microdroplet-based PCR enrichment for large-scale targeted sequencing," Nat Biotechnol 27(11):1025-1031; Supplementary materials: 33 pages.
Tomilin, et al., "Mechanisms of Chromosome Destabilization in Human Cells", Sov. Sci. Rev. D. Physiochem. Biol., 10:39-89 (1992).
Tong, et al., "Noninvasive prenatal detection of fetal trisomy 18 by epigenetic allelic ratio analysis in maternal plasma: theoretical and empirical considerations", Clin Chem, 52:2194-202 (2006).
Tsui, et al., "Noninvasive prenatal diagnosis of hemophilia by microfluidics digital PCR analysis of maternal plasma DNA", Blood, 117:3684-91 (2011).
Tsui, et al., "Systematic microarray-based identification of placental mRNA in maternal plasma: towards noninvasive prenatal gene expression profiling", J. Med Genet, 41:461-67 (2004).
U.S. National Library of Medicine. (Jan. 2013). Genetics Home Reference—ATM serine/threonine kinase. Located at <https://ghr.nlm.nih.gov/gene/ATM>, last visited Jun. 13, 2013, 4 pages.
Ulbright, "Germ cell tumors of the gonads: a selective review emphasizing problems in differential diagnosis, newly appreciated, and controversial issues," Modern Pathology, 18:S61-S79 (2005).
Van Opstal, et al., "Rapdi aneuploidy detection with multiplex ligation-dependent probe amplification: a prospective study of 4000 amniotice fluid samples", Eur. J. of Hum. Genetics, 17:112-21 (2009).
Vasioukhin, et al., "Point mutations in the N-ras gene in the blood plasma DNA of patients with myelodysplastic cyndrome or acute myelogenous leukaemia", British J. of Haematology, 86:774-79 (1994).
Vogelstein, et al., "Digital PCR", PNAS USA, 96:9236-41 (1999).
Wachtel, et al., "Fetal cells in the maternal circulation: Isolation by multiparameter flow cytometry and confirmation by polymerase chain reaction", Human Reprod., 6(10):1466-69 (1991).
Wald, et al., "Antenatal maternal serum screening for Down's syndrome: results of a demonstration project", BMJ, 305(6850):391-94 (1992).
Wald, et al., "Maternal serum screening for Down's syndrome in early pregnancy", BMJ, 297:883-87 (1988).
Walker, et al., "Human DNA quantitation using Alu element-based polymerase chain reaction", Analytical Biochem., 315:122-28 (2003).
Wang, et al., "PennCNV: An integrated hidden Markov model designed for high-resolution copy number variation detection in whole-genome SNP genotyping data", Genome Res., 17:1665-74 (2007).
Ward, et al., "Reactivities of serotyping monoclonal antibodies with culture-adapted human rotaviruses", J. Clin. Microbiol. 29(3):422-25 (1991).
Winsor, et al., "Maternal Cell Contamination in Uncultured Amniotic Fluid", Prenatal Diagnosis, 16:49-54 (1996).
Witt, et al., "An improved, non-isotopic method of screening cells from patients with abnormalities of sexual differentiation for Y chromosomal DNA content", J. Med. Genet., 30:304-07 (1993).
Wu and Wallace, "The ligation amplification reaction (LAR)—Amplification of specific DNA sequences using sequential rounds of template-dependent ligation", Genomics, 4:560-69 (1989).
Xie and Tammi, "CNV-seq, a new method to detect copy number variation using high throughput sequencing", BMC Bioinformatics, 10:80 (2008), doi 10.1186/1471-2105-10-80, p. 1-9.
Young and Davis, "Efficient isolation of genes by using antibody probes", PNAS 80:1194-98 (1983).
Zolotukhina, et al., "Analysis of Cell-free DNA in Plasma and Serum of Pregnant Women", J. of Hist. and Cytochem., 53:297-99 (2005).
Bustamante-Aragones et al. (Mar. 2010). "Noninvasive prenatal diagnosis using ccffDNA in maternal blood: state of the art," *Expert Reviews in Molecular Diagnostics* 10(2):197-205.
Chinen, P.A. et al. (Nov. 2010), e-published Apr. 20, 2010). "Noninvasive determination of fetal rh blood group, D antigen status by cell-free DNA analysis in maternal plasma: experience in a Brazilian population," *Am J Perinatology* 27(1):759-762.
Guo, Q. et al. (Sep. 2010, e-published Jul. 9, 2010). "Simultaneous detection of trisomies 13, 18, and 21 with multiplex ligation-dependent probe amplification-based real-time PCR," *Clin Chem* 56(9):1451-1459.
Wright, C.F. et al. (Jan.-Feb. 2009, e-published Oct. 22, 2008). "The use of cell-free fetal nucleic acids in maternal blood for non-invasive prenatal diagnosis," *Human Reprod Update* 15(10):139-151.

\* cited by examiner

| Sample | Sample Tag | Fetal Gender | Genome Equivs. | Maternal Karyotype | Fetal Karyotype | Mater Age | GestAge (Day) | # Loci DiffPoly | % Fetal | Mean18 | Mean21 | Prop18 | Prop21 | ZStat18 | ZStat21 |
|---|---|---|---|---|---|---|---|---|---|---|---|---|---|---|---|
| 1 | TGTCCCC | M | 2293 | 46XX | 46XY | 45 | 110 | 38 | 0.210138 | 1005.426 | 999.4412 | 0.501493 | 0.498867 | 0.48436 | -0.48436 |
| 2 | ATCCTCC | F | 3593 | 46XX | 46XX | 37 | 131 | 45 | 0.096075 | 996.6228 | 998.7823 | 0.499459 | 0.500541 | -0.84491 | 0.84491 |
| 4 | GCCAACC | F | 1469 | 46XX | 46XX | 34 | 121 | 26 | 0.238051 | 993.0624 | 997.5193 | 0.498376 | 0.501624 | -1.55236 | 1.552358 |
| 5 | CCACGAC | F | 1296 | 46XX | 46XX | 36 | 129 | 36 | 0.140639 | 1010.048 | 1004.468 | 0.501385 | 0.498615 | 0.413907 | -0.41391 |
| 6 | TCCTCYT | F | 2319 | 46XX | 46XX | 33 | 136 | 24 | 0.049392 | 994.7681 | 1000.652 | 0.498531 | 0.501469 | -1.451169 | 1.451169 |
| 7 | CCTTGCT | F | 2772 | 46XX | 46XX | 43 | 111 | 42 | 0.095395 | 997.3445 | 986.4745 | 0.50274 | 0.49726 | 1.299353 | -1.29935 |
| 8 | TCACTCT | M | 2506 | 46XX | 46XY | 34 | 126 | 32 | 0.158725 | 1004.857 | 996.2886 | 0.502128 | 0.497872 | 0.899842 | -0.89984 |
| 9 | CATCTTC | M | 3996 | 46XX | 46XY | 36 | 121 | 34 | 0.118817 | 1005.714 | 1002.285 | 0.500854 | 0.499146 | 0.067201 | -0.06672 |
| 10 | TTCGCCG | F | 4032 | 46XX | 46XX | 42 | 84 | 29 | 0.159776 | 999.7097 | 1000.399 | 0.499828 | 0.500172 | -0.60393 | 0.60393 |
| 11 | GTGTCCC | F | 4212 | 46XX | 46XX | 36 | 175 | 39 | 0.119147 | 1004.796 | 995.1465 | 0.502412 | 0.497588 | 1.085457 | -1.08546 |
| 12 | GCCCTTG | F | 3816 | 46XX | 46XX | 36 | 111 | 27 | 0.085664 | 1002.909 | 999.3516 | 0.500868 | 0.499132 | 0.089291 | -0.08929 |
| 13 | CTTACAC | F | 2160 | 46XX | 46XX | 41 | 123 | 40 | 0.117371 | 1002.012 | 995.6877 | 0.501734 | 0.498266 | 0.641893 | -0.64189 |
| 14 | TCGCAGC | F | 2790 | 46XX | 46XX | 51 | 125 | 36 | 0.119314 | 1008.515 | 999.3439 | 0.502284 | 0.497716 | 1.061374 | -1.06137 |
| 15 | CGGCCAT | F | 2783 | 46XX | 46XX | 51 | 125 | 50 | 0.123598 | 1005.525 | 998.867 | 0.501661 | 0.498339 | 0.584272 | -0.59427 |
| 16 | CCAGCTG | M | 2272 | 46XX | 46XY | 34 | 110 | 40 | 0.119257 | 1010.173 | 1004.256 | 0.501468 | 0.498532 | 0.468561 | -0.46856 |
| 17 | AGCACCT | M | 2491 | 46XX | 46XY | 34 | 140 | 43 | 0.111573 | 988.7338 | 986.5967 | 0.500541 | 0.499459 | -0.13768 | 0.137679 |
| 18 | CGATACC | F | 3960 | 46XX | 46XX | 41 | 126 | 27 | 0.098872 | 996.8338 | 999.2182 | 0.499403 | 0.500597 | -0.88162 | 0.88162 |
| 19 | CCCGAAT | M | 3816 | 46XX | 46XY | 37 | 133 | 30 | 0.095735 | 999.3982 | 991.0248 | 0.502103 | 0.497897 | 0.883556 | -0.88356 |
| 20 | CCCAGGG | M | 3474 | 46XX | 46XY | 36 | 123 | 32 | 0.135184 | 1006.395 | 992.8395 | 0.50339 | 0.49661 | 1.724514 | -1.72451 |
| 21 | CAGCACG | M | 1080 | 46XX | 46XY | 38 | 97 | 28 | 0.13036 | 994.7498 | 1003.364 | 0.497844 | 0.502156 | -1.90014 | 1.900139 |

FIG. 7

| Sample Tag | Fetal Gender | Genome Equivs. | Maternal Karyotype | Fetal Karyotype | Mater Age | GestAge (Days) | Informative Loci | % Fetal | Mean18 | Mean21 | Prop18 | Prop21 | ZStat18 | ZStat21 |
|---|---|---|---|---|---|---|---|---|---|---|---|---|---|---|
| CTCTATG | M | 2002 | 46XX | 46XY | 30 | 123 | 30 | 0.08322 | 994.7936 | 999.994 | 0.4998697 | 0.501303 | -1.3432 | 1.343199 |
| ACTTTAC | M | 3942 | 46XX | 46XY | 35 | 130 | 33 | 0.138751 | 1004.97 | 1003.103 | 0.5024635 | 0.4995135 | -0.18713 | 0.187128 |
| CGTATCG | F | 1922 | 46XX | 46XX | 23 | 159 | 29 | 0.254234 | 1003.218 | 1006.4 | 0.4993208 | 0.500792 | -1.06868 | 1.008678 |
| AAGCATT | M | 3708 | 46XX | 46XY | 38 | 148 | 31 | 0.145101 | 996.0673 | 995.7268 | 0.5000085 | 0.499915 | -0.435338 | 0.435383 |
| CTGGCGC | M | 4032 | 46XX | 46XY | 30 | 126 | 27 | 0.077438 | 1005.191 | 1003.628 | 0.500389 | 0.499611 | -0.23694 | 0.23694 |
| TGCCGAG | F | 2383 | 46XX | 46XX | 35 | 138 | 32 | 0.131712 | 996.445 | 1002.698 | 0.498436 | 0.501564 | -1.51345 | 1.513451 |
| ATACCAG | F | 4104 | 46XX | 46XX | 23 | 99 | 33 | 0.098894 | 991.6721 | 1001.903 | 0.497434 | 0.502566 | -2.16839 | 2.168385 |
| GAAACCG | F | 2437 | 46XX | 46XX | 33 | 149 | 25 | 0.067606 | 1004.187 | 1006.778 | 0.499356 | 0.500644 | -0.91231 | 0.912305 |
| AAAGGCC | F | 2765 | 46XX | 46XX | 23 | 126 | 29 | 0.144098 | 1001.398 | 995.2881 | 0.501508 | 0.498492 | 0.494093 | -0.494409 |
| TCTAATT | M | 2416 | 46XX | 46XY | 23 | 139 | 28 | 0.105371 | 1006.535 | 1005.069 | 0.500364 | 0.499636 | -0.25309 | 0.25309 |
| GTTGATC | M | 2653 | 46XX | 46XY | 34 | 148 | 29 | 0.164518 | 1003.738 | 998.0583 | 0.501419 | 0.498581 | 0.435957 | -0.435967 |
| GATGTCT | M | 7488 | 46XX | 46XY | 36 | 148 | 21 | 0.056635 | 1012.154 | 1002.257 | 0.502456 | 0.497544 | 1.114241 | -1.11424 |
| AGTGTGT | M | 2653 | 46XX | 46XY | 26 | 140 | 39 | 0.21197 | 1004.959 | 996.9646 | 0.501997 | 0.498003 | 0.813799 | -0.8138 |
| AATTCTG | F | 3780 | 46XX | 46XX | 35 | 133 | 43 | 0.259642 | 997.0406 | 997.6786 | 0.499833 | 0.500169 | -0.60140 | 0.601493 |
| CTAAGTT | M | 8136 | 46XX | 46XY | 26 | 151 | 33 | 0.082773 | 1007.02 | 1006.742 | 0.500069 | 0.499931 | -0.44599 | 0.445992 |
| GGCGGTT | M | 2228 | 46XX | 46XY | 37 | 134 | 37 | 0.15551 | 1004.912 | 1003.415 | 0.500323 | 0.499677 | -0.28021 | 0.280209 |
| TATAGKC | F | 4248 | 46XX | 46XX | 27 | 165 | 46 | 0.064469 | 1014.599 | 995.8518 | 0.504662 | 0.495338 | 2.556064 | -2.55606 |
| TAGGTAC | M | 3960 | 46XX | 46XY | 35 | 124 | 41 | 0.167184 | 997.8251 | 998.4044 | 0.499855 | 0.500145 | -0.58668 | 0.586381 |
| CAATCCG | F | 4140 | 46XX | 46XX | 24 | 127 | 43 | 0.129398 | 997.6895 | 996.5093 | 0.500271 | 0.499729 | -0.43425 | 0.314232 |
| TCATAAG | M | 4330 | 46XX | 46XY | 39 | 139 | 29 | 0.227198 | 1002.31 | 994.6654 | 0.502269 | 0.497331 | 1.253298 | -1.2533 |
| GAACCGT | F | 3744 | 46XX | 46XX | 36 | 118 | 39 | 0.094147 | 1007.442 | 994.0998 | 0.503333 | 0.496667 | 1.687193 | -1.68719 |

FIG. 7 (cont.)

| Sample | Sample Tag | Fetal Gender | Genome Equivs. | Maternal Karyotype | Fetal Karyotype | Mater Age | GestAge (Day) | Informative Loci | % Fetal | Mean18 | Mean21 | Prop18 | Prop21 | ZStat18 | ZStat21 |
|---|---|---|---|---|---|---|---|---|---|---|---|---|---|---|---|
| 43 | AAGGCGT | F | 6984 | 46XX | 46XX | 37 | 130 | 36 | 0.235387 | 998.8644 | 995.701 | 0.507793 | 0.499207 | 0.027059 | -0.02706 |
| 44 | AGGAATC | F | 5112 | 46XX | 46XX | 18 | 188 | 39 | 0.244261 | 1001.465 | 995.804 | 0.501417 | 0.498583 | 0.435058 | -0.43506 |
| 45 | AACATAG | F | 3503 | 46XX | 46XX | 41 | 141 | 22 | 0.106969 | 999.5094 | 990.8389 | 0.502178 | 0.497822 | 0.932375 | -0.93238 |
| 46 | TTTCGAT | F | 2866 | 46XX | 46XX | 39 | 143 | 32 | 0.196098 | 1001.959 | 1009.069 | 0.504472 | 0.495528 | -0.18279 | 0.182795 |
| 47 | TTGATGT | F | 5292 | 46XX | 46XX | 36 | 111 | 30 | 0.109084 | 1004.708 | 1002.777 | 0.500481 | 0.499519 | -0.17694 | 0.176939 |
| 48 | ATGCTTG | M | 5184 | 46XX | 46XY | 24 | 160 | 40 | 0.060517 | 1010.204 | 1006.293 | 0.510097 | 0.499813 | 0.143013 | -0.143 |
| 49 | GGGTAGT | M | 3996 | 46XX | 46XY | 23 | 153 | 30 | 0.151707 | 1003.952 | 998.371 | 0.501394 | 0.498606 | 0.419853 | -0.41955 |
| 50 | AGATGAT | F | 5256 | 46XX | 46XX | 26 | 118 | 26 | 0.126345 | 998.3654 | 996.1826 | 0.504497 | 0.499503 | -0.16635 | 0.166347 |
| 51 | GTGAAAG | M | 4068 | 46XX | 46XY | 33 | 140 | 29 | 0.214532 | 1004.428 | 996.9586 | 0.501866 | 0.498134 | 0.728436 | -0.72844 |
| 52 | AGTGAAG | M | 11412 | 46XX | 46XY | 18 | 196 | 24 | 0.140258 | 1007.84 | 998.7992 | 0.502253 | 0.497747 | 0.9811 | -0.9811 |
| 53 | ACAACGC | M | 3146 | 46XX | 46XY | 21 | 147 | 32 | 0.180869 | 1010.525 | 999.8358 | 0.502659 | 0.497341 | 1.24639 | -1.24639 |
| 54 | GACGAGG | F | 5508 | 46XX | 46XX | 35 | 114 | 32 | 0.053622 | 994.8149 | 1005.452 | 0.497341 | 0.502659 | -2.22916 | 2.229159 |
| 55 | GGAATAC | F | 6624 | 46XX | 46XX | 28 | 140 | 37 | 0.21338 | 999.7187 | 1006.639 | 0.498275 | 0.501725 | -1.61846 | 1.618464 |
| 56 | GTTCGCG | M | 6192 | 46XX | 46XY | 44 | 115 | 25 | 0.083131 | 1009.447 | 999.2224 | 0.502555 | 0.497445 | 1.178758 | -1.17876 |
| 57 | GTCTTAT | F | 7056 | 46XX | 46XX | 25 | 115 | 37 | 0.135201 | 1005.611 | 996.4 | 0.5023 | 0.4977 | 1.031226 | -1.03123 |
| 58 | TAGTGTT | F | 5148 | 46XX | 46XX | 22 | 99 | 38 | 0.124127 | 996.363 | 999.6895 | 0.499167 | 0.500833 | -1.05787 | 1.035871 |
| 59 | TGCTTTC | M | 4104 | 46XX | 46XY | 30 | 197 | 28 | 0.310846 | 1004.506 | 1009.571 | 0.498743 | 0.501257 | -1.31256 | 1.312564 |
| 60 | TCTGTGG | M | 5364 | 46XX | 46XY | 27 | 122 | 26 | 0.118328 | 997.1746 | 992.0824 | 0.501128 | 0.498672 | 0.345307 | -0.34531 |
| 61 | TGGCCTC | F | 3636 | 46XX | 46XX | 28 | 178 | 30 | 0.138146 | 989.5388 | 999.8624 | 0.497405 | 0.502595 | -2.18759 | 2.187092 |
| 62 | TGAGTAT | M | 17856 | 46XX | 46XY | NA | NA | 45 | 0.064088 | 993.7189 | 996.5081 | 0.499299 | 0.500701 | -0.94924 | 0.949237 |
| 63 | TCCAAAT | F | 5604 | 46XX | 46XX | 35 | 109 | 39 | 0.076783 | 1003.939 | 992.77595 | 0.5028 | 0.4972 | 1.33858 | -1.33858 |

FIG. 7 (cont.)

| Sample | Sample Tag | Fetal Gender | Genome Equivs. | Maternal Karyotype | Fetal Karyotype | Mater Age | GestAge (Day) | Informative Loci | % Fetal | Mean18 | Mean21 | Prop18 | Prop21 | ZStat18 | ZStat21 |
|---|---|---|---|---|---|---|---|---|---|---|---|---|---|---|---|
| 64 | TATCAAT | M | 8712 | 46XX | 46XY | 35 | 119 | 33 | 0.077373 | 1014.37 | 996.8203 | 0.501886 | 0.498114 | 0.741595 | -0.74159 |
| 65 | TAAGAGT | F | 2552 | 46XX | 46XX+13 | 35 | 90 | 41 | 0.144442 | 999.7136 | 986.3962 | 0.502846 | 0.497154 | 1.369064 | -1.369066 |
| 66 | TAAAGAT | F | 7668 | 46XX | 46XX+13 | 30 | 141 | 37 | 0.057793 | 998.6741 | 990.8426 | 0.501968 | 0.498032 | 0.795353 | -0.79515 |
| 67 | TCTGCAC | M | 3996 | 46XX | 46XY+13 | 35 | 161 | 26 | 0.21564 | 1001.317 | 998.1811 | 0.500784 | 0.499216 | 0.021337 | -0.02134 |
| 68 | GTYGGCT | F | 7580 | 46XX | 46XX+21 | 35 | 125 | 28 | 0.0925662 | 983.1548 | 1024.755 | 0.489641 | 0.510359 | -7.2619 | 7.2619 |
| 69 | GTGACTT | F | 13248 | 46XX | 46XX+21 | 19 | 132 | 30 | 0.085949 | 980.027 | 1020.997 | 0.489763 | 0.510237 | -7.18225 | 7.182254 |
| 70 | GGTCAGC | F | 7452 | 46XX | 46XX+21 | 40 | 91 | 31 | 0.056151 | 990.5328 | 1011.076 | 0.494868 | 0.505132 | -3.84552 | 3.845324 |
| 71 | GGGCGAG | M | 5568 | 46XX | 46XY+21 | 18 | 166 | 32 | 0.140102 | 965.1286 | 1037.339 | 0.48197 | 0.51803 | -12.2758 | 12.27579 |
| 73 | GGCTAAC | M | 5384 | 46XX | 46XY+18 | 29 | 147 | 29 | 0.157072 | 1044.147 | 963.7049 | 0.52081 | 0.47919 | 13.11032 | -13.1101 |
| 75 | GAGTGCG | F | 2689 | 46XX | 46XX+18 | 40 | 93 | 24 | 0.129256 | 1038.787 | 958.3378 | 0.520141 | 0.479859 | 12.67306 | -12.6731 |
| 76 | GAATGAC | F | 7632 | 46XX | 46XX+18 | 43 | 133 | 24 | 0.048391 | 1015.894 | 982.9916 | 0.508823 | 0.491177 | 4.887983 | -4.88796 |
| 78 | GCTTGTG | F | 7128 | 46XX | 46XX+18 | 25 | 128 | 30 | 0.06035 | 1018.978 | 985.6703 | 0.506378 | 0.491692 | 4.938613 | -4.93861 |
| 79 | GCAGAAC | M | 4464 | 46XX | 46XY+18 | 40 | 82 | 31 | 0.082749 | 1022.638 | 974.749 | 0.511988 | 0.488012 | 7.344068 | -7.34467 |
| 80 | ATCGAAT | F | 2160 | 46XX | 46XX+18 | 42 | 98 | 39 | 0.094043 | 1023.162 | 977.342 | 0.511452 | 0.488548 | 6.993832 | -6.99383 |
| 81 | ATCAGAT | M | 4176 | 46XX | 46XY+21 | 35 | 147 | 33 | 0.148476 | 957.3759 | 1038.729 | 0.479622 | 0.520378 | -13.8302 | 13.81016 |
| 82 | AGTTACT | M | 4508 | 46XX | 46XY+21 | 39 | 124 | 19 | 0.2054496 | 932.9748 | 1049.25 | 0.475955 | 0.524042 | -16.205 | 16.20502 |
| 83 | AGTAGAC | M | 8640 | 46XX | 46XY+21 | 37 | 125 | 30 | 0.130907 | 973.5572 | 1028.835 | 0.486146 | 0.513854 | -9.54628 | 9.546281 |
| 84 | AGGTCTT | M | 16092 | 46XX | 46XY+21 | 43 | 94 | 35 | 0.126545 | 976.6225 | 1029.797 | 0.486749 | 0.513251 | -9.1521 | 9.152097 |
| 85 | AGGATAT | M | 4212 | 46XX | 46XY+21 | 40 | 157 | 24 | 0.119821 | 969.1251 | 1025.932 | 0.485763 | 0.514237 | -9.79643 | 9.796425 |
| 86 | AGGACGG | M | 4644 | 46XX | 46XY+21 | 33 | 97 | 33 | 0.053737 | 992.2248 | 1011.59 | 0.495168 | 0.504832 | -3.64943 | 3.649465 |
| 87 | AGAGATT | M | 4320 | 46XX | 46XY+21 | 51 | 119 | 37 | 0.08022 | 978.7159 | 1014.132 | 0.491114 | 0.508886 | -6.29894 | 6.298937 |

FIG. 7 (cont.)

| Sample | Sample Tag | Fetal Gender | Genome Equivs. | Maternal Karyotype | Fetal Karyotype | Mater Age | GestAge (Day) | Informative Loci | % Fetal | Mean18 | Mean21 | Prop18 | Prop21 | ZSta18 | ZSta21 |
|---|---|---|---|---|---|---|---|---|---|---|---|---|---|---|---|
| 89 | AGCTGCCC | F | 6768 | 46XX | 46XX+21 | 31 | 98 | 35 | 0.126696 | 963.2256 | 1024.818 | 0.484509 | 0.515491 | -10.616 | 10.61595 |
| 90 | AGCGCTG | M | 1375 | 46XX | 46XY+21 | 36 | 162 | 36 | 0.133202 | 961.1764 | 1032.034 | 0.482225 | 0.517775 | -12.1088 | 12.10879 |
| 91 | AGCATGC | M | 5155 | 46XX | 46XY+21 | 41 | 154 | 37 | 0.095349 | 967.2823 | 1017.613 | 0.487322 | 0.512678 | -8.77777 | 8.777767 |
| 92 | AATGTT | F | 2549 | 46XX | 46XX+21 | 41 | 119 | 32 | 0.09505 | 965.3134 | 1025.737 | 0.484831 | 0.515169 | -10.4856 | 10.4856 |
| 93 | AAGTAAG | F | 9216 | 46XX | 46XX+21 | 42 | 253 | 32 | 0.209915 | 946.0902 | 1052.948 | 0.472273 | 0.526727 | -17.96 | 17.96002 |
| 94 | AAATAGC | F | 2941 | 46XX | 46XX+21 | 36 | 161 | 32 | 0.102554 | 973.7957 | 1025.545 | 0.487058 | 0.512942 | -8.94982 | 8.949816 |
| 95 | AAATCCT | M | 1843 | 46XX | 46XY+21 | 42 | 93 | 35 | 0.137238 | 965.4467 | 1031.552 | 0.483449 | 0.516551 | -11.309 | 11.30904 |

FIG. 7 (cont.)

SEQUENCE LISTING

<160> NUMBER OF SEQ ID NOS: 11

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 1

```
tacaccggcg ttatgcgtcg agac                                           24

<210> SEQ ID NO 2
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 2
attgcgggga ccgatgatcg cgtc                                           24

<210> SEQ ID NO 3
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 3
taatgatacg gcgaccaccg agatctacac cggcgttatg cgtcgaga                 48

<210> SEQ ID NO 4
<211> LENGTH: 53
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (26)..(26)
<223> OTHER INFORMATION: n = a, c, g, or t

<400> SEQUENCE: 4
tcaagcagaa gacggcatac gagatnaaac gacgcgatca tcggtccccg caa           53

<210> SEQ ID NO 5
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 5
taatgatacg gcgaccaccg a                                              21

<210> SEQ ID NO 6
<211> LENGTH: 25
<212> TYPE: DNA
<213> ORGANISM: Artificial Sequence
<220> FEATURE:
<223> OTHER INFORMATION: Synthetic Oligonucleotide

<400> SEQUENCE: 6
atctcgtatg ccgtcttctg cttga                                          25

<210> SEQ ID NO 7
<211> LENGTH: 48
<212> TYPE: DNA
<213> ORGANISM: Artificial Sequence
<220> FEATURE:
<223> OTHER INFORMATION: Synthetic Oligonucleotide

<400> SEQUENCE: 7
aatgatacgg cgaccaccga gatctacacc ggcgttatgc gtcgagac                 48
```

<210> SEQ ID NO 8
<211> LENGTH: 60
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (26)..(32)
<223> OTHER INFORMATION: n = a, c, g, or t

<400> SEQUENCE: 8
tcaagcagaa gacggcatac gagatnnnnn nnaaacgacg cgatcatcgg tccccgcaat    60

<210> SEQ ID NO 9
<211> LENGTH: 52
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (27)..(27)
<223> OTHER INFORMATION: w = a or t

<400> SEQUENCE: 9
tttacatgtc tttgggcatt ttaggtwgag tgaaatctag gccttgcaaa tc            52

<210> SEQ ID NO 10
<211> LENGTH: 52
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (27)..(27)
<223> OTHER INFORMATION: w = a or t

<400> SEQUENCE: 10
ttgtgtaacg ttaacctcag ggaccawgag atgtacttag tattaatttg cc            52

<210> SEQ ID NO 11
<211> LENGTH: 52
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: (27)..(27)
<223> OTHER INFORMATION: w = a or t

<400> SEQUENCE: 11
ggaagaagtg cagtgtagta gacaacwctg gcattgtgtt ttgtgaactg gg            52

ASSAY SYSTEMS FOR GENETIC ANALYSIS

CROSS-REFERENCE TO RELATED APPLICATIONS

This application is a continuation of U.S. application Ser. No. 13/205,490, filed Aug. 8, 2011, which is a continuation-in-part of U.S. application Ser. No. 13/013,732, filed Jan. 25, 2011, which claims priority to U.S. Ser. No. 61/371,605, filed Aug. 6, 2010, which are herein incorporated by reference in their entities.

INCORPORATION-BY-REFERENCE OF A SEQUENCE LISTING

The content of the following submission of ASCII text file is incorporated herein by reference in its entirety: a computer readable form (CFR) of the Sequence Listing (file name: 50876-502C03US_SEQLIST.txt, date recorded: Nov. 28, 2016, size: 2,995 bytes).

FIELD OF THE INVENTION

This invention relates to the detection and quantification of genetic variation in mixed samples in a single assay.

BACKGROUND OF THE INVENTION

In the following discussion certain articles and methods will be described for background and introductory purposes. Nothing contained herein is to be construed as an "admission" of prior art. Applicant expressly reserves the right to demonstrate, where appropriate, that the articles and methods referenced herein do not constitute prior art under the applicable statutory provisions.

Genetic abnormalities account for a wide number of pathologies, including pathologies caused by chromosomal aneuploidy (e.g., Down syndrome), germline mutations in specific genes (e.g., sickle cell anemia), and pathologies caused by somatic mutations (e.g., cancer). Diagnostic methods for determining such genetic anomalies have become standard techniques for identifying specific diseases and disorders, as well as providing valuable information on disease source and treatment options.

Although conventional technology provides detection methods for these different genetic abnormalities, it currently requires different techniques to interrogate different classes of mutations. An assay providing detection of a copy number variation with simultaneous detection of individual gene polymorphisms would be a powerful tool in the treatment. The present invention addresses this need.

There is thus a need for non-invasive methods of screening for genetic abnormalities, including copy number variations, in mixed samples comprising normal and putative abnormal DNA. The present invention addresses this need.

SUMMARY OF THE INVENTION

This Summary is provided to introduce a selection of concepts in a simplified form that are further described below in the Detailed Description. This Summary is not intended to identify key or essential features of the claimed subject matter, nor is it intended to be used to limit the scope of the claimed subject matter. Other features, details, utilities, and advantages of the claimed subject matter will be apparent from the following written Detailed Description including those aspects illustrated in the accompanying drawings and defined in the appended claims.

The present invention provides assay systems and related methods for determining genetic variation in mixed samples comprising genomic material (e.g., cell free DNA) from a major and one or more minor sources from a subject. More particularly, the present invention provides assay systems and methods for detection of copy number variation of one or more loci and detection of polymorphisms in one or more loci in a sample comprising nucleic acids from a major source and a minor source within an individual. The present invention utilizes a single assay system that allows the identification of both genetic copy number variations (CNVs) and single gene polymorphisms, and the ability to distinguish between these CNVs and polymorphisms in the major and minor sources.

In one aspect, the assay system utilizes amplification and detection of selected loci in a mixed sample from an individual to identify the copy number and presence of polymorphisms in selected loci from a major and one or more minor sources.

In one specific aspect, the invention provides single assay systems with the ability to determine 1) the presence or absence of CNVs at one or more loci and; 2) the presence or absence of polymorphisms at one or more loci in a mixed sample from an individual. The assay system can specifically detect copy number of selected loci and polymorphisms present in selected loci from a minor source within the mixed sample, and to distinguish this from the copy number and polymorphisms present in selected loci from a major source in the mixed sample. Preferably, the loci are analyzed through use of cell free nucleic acids, and preferably the cell free nucleic acids analyzed in the assay system are cell free DNA (cfDNA).

Thus, in a specific aspect, the invention provides an assay system for detection of the presence or absence of a copy number variation (CNV) of a genomic region and presence or absence of one or more polymorphisms in a mixed sample using a single assay, the assay comprising the steps of introducing a first set of fixed sequence oligonucleotides to a mixed sample under conditions that allow the fixed sequence oligonucleotides to specifically hybridize to complementary regions on one or more loci in or associated with a genomic region; introducing a second set of fixed sequence oligonucleotides comprising universal primer regions to the mixed sample under conditions that allow the fixed sequence oligonucleotides to specifically hybridize to complementary regions on one or more loci with a putative polymorphism; ligating the hybridized oligonucleotides to create contiguous ligation products complementary to the loci corresponding to a genomic region and/or the loci with a putative polymorphism; amplifying the contiguous ligation products to create amplification products; and detecting the amplification products. The detection of the amplification products correlates to the copy number of one or more genomic regions and the presence or absence of a polymorphism in one or more loci in the mixed sample.

In certain aspects, the fixed sequence oligonucleotides hybridize to adjacent regions in the loci, and the fixed sequence oligonucleotides are directly ligated during the ligation step of the assay. In other aspects, the fixed sequence oligonucleotides hybridize to non-adjacent regions in the loci that are separated by one, a few, or several nucleotides, and the region between the fixed sequence oligonucleotides is used as a template for primer extension to close the gap between the fixed sequence oligonucleotides prior to the ligation step.

Thus, in a second aspect, the invention provides an assay system for detection of the presence or absence of CNV of a genomic region and presence or absence of one or more polymorphisms in a mixed sample using a single assay, the assay comprising the steps of: introducing a first set of fixed sequence oligonucleotides to a mixed sample under conditions that allow the fixed sequence oligonucleotides to specifically hybridize to complementary regions on one or more loci in or associated with a genomic region; introducing a second set of fixed sequence oligonucleotides to the mixed sample under conditions that allow the fixed sequence oligonucleotides to specifically hybridize to complementary regions on one or more loci with a putative polymorphism; extending the region between the first and second hybridized oligonucleotide of at least one fixed sequence oligonucleotide set with a polymerase and dNTPs to create two adjacently hybridized fixed sequence oligonucleotides from that set; ligating the hybridized oligonucleotides to create contiguous ligation products complementary to the loci corresponding to a genomic region and/or the loci with a putative polymorphism; amplifying the contiguous ligation products using the universal primer regions to create amplification products; and detecting the amplification products. The detection of the amplification products correlates to the copy number of one or more genomic region and the presence or absence of a polymorphism in one or more loci in the mixed sample.

In a preferred aspect, the fixed sequence oligonucleotides used to interrogate the specific loci comprise universal primer regions that are common to substantially all of the fixed sequence oligonucleotides used in a particular assay. This allows substantially all of the ligation products produced in a single assay to be amplified, isolated and/or analyzed using similar mechanisms (e.g., sequence determination or hybridization). Use of such universal primer regions obviates the need for individually distinguishable detectable moieties associated with particular loci or alleles, and provides a more efficient and cost-effective mechanisms for multiplexing interrogation and/or analysis of multiple loci from one or multiple samples. In a preferred aspect, the universal primer regions are used in sequence determination of the amplification products. In another preferred aspect, the same universal primer regions are used in the fixed sequence oligonucleotides used for detection of genomic regions and the fixed sequence oligonucleotides used for detection of polymorphisms.

Each set of fixed sequence nucleic acids is designed to hybridize to at least two separate regions in a selected locus. In preferred aspects, two or more separate oligos are used in a set to hybridize to these regions to provide adjacent nucleic acids complementary to the selected loci. In some aspects, however, a set can comprise a single probe with two or more distinct non-adjacent regions that are complementary to the selected loci (e.g., padlock probes), as described in more detail herein. The sets of fixed sequence oligos can be provided in the assay sequentially or simultaneously in the assay.

The genomic region can be a single locus, or it may be a larger region, up to and including a chromosome. For determination of larger genomic regions, sets of loci may be used to determine the size and in certain aspects the boundaries of such genomic regions for which CNV has been detected.

In certain aspects, the amplification products of the assay are isolated prior to detection. Preferably, the amplification products are isolated as individual molecules prior to detection. These isolated amplification products can optionally be further amplified to create identical copies of all or a portion of the individual amplification products prior to detection, or further amplified to create identical copies of molecules complementary to all or a portion of the individual amplification products prior to detection.

The multiplexed assays of the invention allow the analysis of 5 or more, preferably 10 or more, preferably 16 or more, preferably 20 or more, preferably 30 or more, preferably 32 or more, preferably 40 or more, preferably 48 or more, preferably 50 or more, preferably 60 or more, preferably 70 or more, preferably 80 or more, preferably 90 or more, and more preferably 96 or more selected loci simultaneously. These selected loci may be different loci from a single sample, or they may be loci from two or more individuals. In the latter case, at least one of the two fixed sequence oligonucleotides used for analysis of a selected locus may comprise a sample identifier (e.g., a "sample index") that will allow the locus to be associated with a particular sample. Alternatively, a sample index may be added during amplification of the ligation product by using a primer comprising the sample index.

Preferably, at least one locus interrogated for CNV in a mixed sample is different from all loci interrogated for polymorphisms in the mixed sample. In specific aspects, several loci interrogated for CNV in a mixed sample are different from the loci interrogated for polymorphisms in the mixed sample. In more specific aspects, the majority of loci interrogated for CNV in a mixed sample are different from the loci interrogated for polymorphisms in the mixed sample.

In some aspects of the invention, the fixed sequence oligonucleotides hybridize to adjacent regions on a locus, and ligation of these oligonucleotides results in a ligation product that joins the two fixed sequence oligonucleotides. In other aspects, the fixed sequence oligonucleotides hybridize to non-adjacent regions on a locus, and the regions between the fixed sequence oligonucleotides is extended using a polymerase and dNTPs. In preferred aspects, the fixed sequence oligonucleotides hybridize to non-adjacent regions on a locus, and one or more bridging oligonucleotides hybridize to the region between and adjacent to the set of fixed sequence oligonucleotides. In certain preferred aspects, the bridging oligonucleotides used can provide content information on polymorphisms in the loci as well as information on frequency of loci for CNV analysis.

In other preferred aspects, the interrogation of these loci utilizes universal amplification techniques that allow amplification of multiple loci in a single amplification reaction. The selected nucleic acids for detection of both the CNV and polymorphisms using the assay system of the invention can be amplified using universal amplification methods following the initial selective amplification from the mixed sample. The use of universal amplification allows multiple nucleic acids regions from a single or multiple samples to be amplified using a single or limited number of amplification primers, and is especially useful in amplifying multiple selected regions in a single reaction.

Thus, in a preferred aspect of the invention, sequences complementary to primers for use in universal amplification are introduced to the selected loci during or following selective amplification. Preferably such sequences are introduced to the ends of such selected nucleic acids, although they may be introduced in any location that allows identification of the amplification product from the universal amplification procedure.

In certain preferred aspects, one or both of the primers used comprise a sample index or other identifier. In a specific aspect, a sample index is included in one or more of the universal primers. The sample index is incorporated into the amplification products, and amplification products from different samples may then be combined. The sample index is preferably detected concurrently with the detection of the CNV or chromosomal abnormality and the detection of polymorphism such that the CNV and polymorphism may be properly assigned to the sample of origin.

Frequencies of selected loci can be determined for a genomic region of interest and compared to the frequencies of loci of one or more other genomic regions of interest and/or one or more reference genomic regions to detect potential CNVs based on loci frequencies in the mixed sample.

In the assay systems of the invention, the amplification products are optionally isolated prior to detection. When isolated, they are preferably isolated as individual molecules to assist in subsequent detection. Following isolation, the amplification products can be further amplified to create identical copies of all or a portion of the individual amplification products prior to detection. Alternatively, the isolated amplification products can be further amplified to create identical copies of molecules complementary to all or a portion of the individual amplification products prior to detection.

Various methods of detection of CNVs can be employed in conjunction with the detection of the polymorphisms in the assay systems of the invention. In one general aspect, the assay system employs a method for determination of a CNV in one or more loci in a mixed sample, comprising the steps of amplifying one or more selected nucleic acids from a first genomic region of interest in a mixed sample; amplifying one or more selected nucleic acids from a second locus of interest in the mixed sample, determining the relative frequency of the selected loci, comparing the relative frequency of the selected loci, and identifying the presence or absence of a CNV based on the compared relative frequencies of the selected nucleic acids from the first and second loci. Preferably, the assay method amplifies two or more selected loci from different genomic regions, although the loci may be located in the same general genomic region for confirmation of CNVs arising from chromosomal abnormalities rather than CNVs from a single locus.

In other aspects, the bridging oligos are degenerate oligos. In other aspects, the bridging oligos are provided as pools of oligos with random sequences that comprise substantially every combination for the particular size of the bridging oligo used with the fixed sequence oligonucleotides.

Although the aspects of the invention using bridging oligonucleotides are described primarily using a single bridging oligo, it is envisioned that multiple bridging oligos that hybridize to adjacent, complementary regions between fixed sequence oligonucleotides can be used in the described methods.

In one preferred aspect, the invention provides an assay system for detection of the presence or absence of copy number variation (CNV) of a genomic region and presence or absence of one or more polymorphisms in a mixed sample using a single assay, the assay comprising the steps of: introducing a first set of fixed sequence oligonucleotides comprising universal primer regions to a mixed sample under conditions that allow the fixed sequence oligonucleotides to specifically hybridize to complementary regions on one or more loci in or associated with a genomic region; introducing a second set of fixed sequence oligonucleotides comprising universal primer regions to the mixed sample under conditions that allow the fixed sequence oligonucleotides to specifically hybridize to complementary, non-adjacent regions on one or more loci with a putative polymorphism; introducing one or more bridging oligonucleotides under conditions that allow the bridging oligonucleotides to specifically hybridize to regions in the loci between the regions complementary to the fixed sequence oligonucleotides of the sets; ligating the hybridized oligonucleotides to create contiguous ligation products complementary to the loci corresponding to a genomic region and/or the loci with a putative polymorphism; amplifying the contiguous ligation products using the universal primer regions to create amplification products; and detecting the amplification products. The detection of the amplification products correlates to the copy number of one or more genomic region and the presence or absence of a polymorphism in one or more loci in the mixed sample.

In another specific aspect, the invention provides an assay system for detection of the presence or absence of CNV of a genomic region and presence or absence of one or more polymorphisms in a mixed sample using a single assay, the assay comprising the steps of: introducing a first set of fixed sequence oligonucleotides to a mixed sample under conditions that allow the fixed sequence oligonucleotides to specifically hybridize to complementary regions on one or more loci in or associated with a genomic region; introducing a second set of fixed sequence oligonucleotides to the mixed sample under conditions that allow the fixed sequence oligonucleotides to specifically hybridize to complementary regions on one or more loci with a putative polymorphism; introducing one or more bridging oligonucleotides under conditions that allow the bridging oligonucleotides to specifically hybridize to regions in the loci between the regions complementary to the fixed sequence oligonucleotides of the set; extending the region between at least one fixed sequence oligonucleotide and a bridging oligonucleotide with a polymerase and dNTPs to create adjacently hybridized fixed sequence oligonucleotides and bridging oligonucleotides; ligating the hybridized oligonucleotides to create contiguous ligation products complementary to the loci corresponding to a genomic region and/or the loci with a putative polymorphism; amplifying the contiguous ligation products using the universal primer regions to create amplification products; and detecting the amplification products. The detection of the amplification products correlates to the copy number of one or more genomic region and the presence or absence of a polymorphism in one or more loci in the mixed sample.

In preferred aspects of the aspects of the invention using bridging oligonucleotides, the first and second set of fixed sequence oligonucleotides are introduced prior to introduction of the bridging oligonucleotides. More preferably, the unhybridized fixed sequence oligonucleotides are removed prior to introduction of the bridging oligonucleotides. In some aspects, the bridging oligonucleotides are introduced simultaneously with the ligation mixture. In other aspects, the hybridization products of the fixed sequence oligonucleotides and the locus are isolated prior to introduction of the bridging oligonucleotides.

In a preferred aspect, the assay system provides highly multiplexed loci interrogation using one or more common bridging oligonucleotides that are complementary to regions in two or more interrogated loci. Thus, the number of bridging oligonucleotides used in the multiplexed assay system will be less than the number of loci interrogated in the assay. In certain specific aspects, the assay system uses a pool of bridging oligonucleotides that are each designed to be compatible with two or more loci interrogated using the assay system of the invention. In these aspects, the bridging oligonucleotides used in the multiplexed assay are preferably designed to have a $T_m$ in a range of ±5° C., more preferably in a range of ±2° C.

In certain aspects, the assay system multiplexes loci interrogation using one or more common bridging oligonucleotides that are complementary to regions in two or more interrogated loci. Thus, the number of bridging oligonucleotides used in the multiplexed assay system will be less than the number of loci interrogated in the assay. In certain specific aspects, the assay system uses a pool of bridging oligonucleotides that are each designed to be compatible with two or more loci interrogated using the assay system of the invention.

In certain aspects, the bridging oligonucleotides are between 2-45 nucleotides in length. In a specific aspect, the bridging oligonucleotides are between 3-9 nucleotides in length. In yet another specific aspect, the oligonucleotides are between 10-30 nucleotides in length.

The loci interrogated for CNV can in some instances be indicative of a duplication of a larger genomic region, e.g., all or part of a chromosome. Preferably, the assay systems can distinguish the copy number of these loci between a major source and a minor source within a mixed sample.

In such aspects, the invention provides assay systems that comprise a single assay system with the ability to detect within a mixed sample from an individual 1) presence or absence of a chromosomal abnormality associated with one or more CNV; and 2) presence or absence of one or more polymorphisms at one or more selected locus. The presence or absence of the chromosomal abnormality is preferably detected through the use of informative loci that allow the assay system to distinguish between nucleic acids from a major source and a minor source.

Thus, in a specific aspect, the invention provides an assay system for detection of the presence or absence of a chromosomal abnormality and the presence or absence of one or more polymorphisms in a mixed sample using a single assay, the assay comprising the steps of: introducing a first set of fixed sequence oligonucleotides comprising universal primer regions to a mixed sample under conditions that allow the fixed sequence oligonucleotides to specifically hybridize to complementary regions on one or more loci with a putative polymorphism; introducing a second set of fixed sequence oligonucleotides comprising universal primer regions to the mixed sample under conditions that allow the fixed sequence oligonucleotides to specifically hybridize to complementary regions on two or more loci from a first chromosome; introducing a third set of fixed sequence oligonucleotides comprising universal primer regions to the mixed sample under conditions that allow the fixed sequence oligonucleotides to specifically hybridize to complementary regions on two or more loci from a second chromosome; introducing one or more bridging oligonucleotides under conditions that allow the bridging oligonucleotides to specifically hybridize to regions in the loci between the regions complementary to the fixed sequence oligonucleotides of the set; ligating the hybridized oligonucleotides to create contiguous ligation products complementary to the nucleic acids; amplifying the contiguous ligation products to create amplification products; and detecting the amplification products. The detection of the amplification products correlates to the presence or absence of a chromosomal abnormality and the presence or absence of a polymorphism in one or more loci in the mixed sample.

In another specific aspect, the invention provides an assay system for detection of the presence or absence of a chromosomal abnormality and presence or absence of one or more polymorphisms in a mixed sample using a single assay, the assay comprising the steps of: introducing a first set of fixed sequence oligonucleotides comprising universal primer regions to a mixed sample under conditions that allow the fixed sequence oligonucleotides to specifically hybridize to complementary regions on one or more loci with a putative polymorphism; introducing a second set of fixed sequence oligonucleotides comprising universal primer regions to the mixed sample under conditions that allow the fixed sequence oligonucleotides to specifically hybridize to complementary regions on two or more loci from a first chromosome; introducing a third set of fixed sequence oligonucleotides comprising universal primer regions to the mixed sample under conditions that allow the fixed sequence oligonucleotides to specifically hybridize to complementary regions on two or more loci from a second chromosome; introducing one or more bridging oligonucleotides under conditions that allow the bridging oligonucleotides to specifically hybridize to regions in the loci between the regions complementary to the fixed sequence oligonucleotides of the set; extending the region between the first and second hybridized oligonucleotide of at least one fixed sequence oligonucleotide set with a polymerase and dNTPs to create two adjacently hybridized fixed sequence oligonucleotides from that set; ligating the hybridized oligonucleotides to create contiguous ligation products complementary to the nucleic acids; amplifying the contiguous ligation products to create amplification products; and detecting the amplification products. The detection of the amplification products correlates to the presence or absence of a chromosomal abnormality and the presence or absence of a polymorphism in one or more loci in the mixed sample.

In some instances, the chromosomal abnormality is associated with gene duplication or loci expansion on a chromosome of interest. In other instances, the chromosomal abnormality is associated with a translocation resulting in the presence of an extra portion of a chromosome in the genome. In yet other instances, the chromosomal abnormality is associated with aneuploidy of a chromosome of interest.

Thus, in one aspect, the invention provides an assay system for detection of the presence or absence of a chromosomal abnormality and the presence or absence of polymorphisms at one or more loci using a single assay, the assay comprising the steps of introducing a first set of fixed sequence oligonucleotides to a mixed sample under conditions that allow the fixed sequence oligonucleotides to specifically hybridize to complementary regions in two or more nucleic acids corresponding to informative loci on two or more chromosomes; introducing a second set of fixed sequence oligonucleotides to the mixed sample under conditions that allow the fixed sequence oligonucleotides to specifically hybridize to complementary regions in nucleic acids indicative of the presence or absence of polymorphisms at one or more loci; introducing one or more bridging oligonucleotides under conditions that allow the fixed sequence oligonucleotides to specifically hybridize to complementary regions in the nucleic acids, wherein one or more bridging oligonucleotides are complementary to a region of the nucleic acids between and immediately adjacent to the regions complementary to the fixed sequence oligonucleotides of each set; ligating the hybridized oligonucleotides to create contiguous ligation products complementary to the nucleic acids; amplifying the contiguous ligation products to create amplification products; and detecting the amplification products. Detection of the amplification product correlates to the detection of the loci in the mixed sample, and can be used to determine the quantity of loci associated with the presence or absence of the chromosomal abnormality and the genetic status of one or more loci in the mixed sample. Detected levels of these nucleic acids can thus be used to determine the presence or absence of the chromosomal abnormality and the presence or absence of a polymorphism at one or more loci from a major source and/or a minor source within a mixed sample.

Thus, in one aspect, the invention provides an assay system for detection of the presence or absence of a chromosomal abnormality and the presence or absence of polymorphisms at one or more loci using a single assay, the assay comprising the steps of introducing a first set of fixed sequence oligonucleotides to a mixed sample under conditions that allow the fixed sequence oligonucleotides to specifically hybridize to complementary regions in two or more nucleic acids corresponding to informative loci on two or more chromosomes; introducing a second set of fixed sequence oligonucleotides to the mixed sample under conditions that allow the fixed sequence oligonucleotides to specifically hybridize to complementary regions in nucleic acids indicative of the presence or absence of polymorphisms at one or more loci; introducing one or more bridging oligonucleotides under conditions that allow the bridging sequence oligonucleotides to specifically hybridize to complementary regions in the nucleic acids, wherein one or more bridging oligonucleotides are complementary to a region of the loci between the regions complementary to the fixed sequence oligonucleotides of each set and immediately adjacent to a first fixed sequence oligonucleotides; extending the region between the bridging oligonucleotide and the second fixed sequence oligonucleotide using polymerase and dNTPs; ligating the hybridized oligonucleotides to create contiguous ligation products complementary to the nucleic acids; amplifying the contiguous ligation products to create amplification products; and detecting the amplification products. Detection of the amplification product correlates to the detection of the loci in the mixed sample, and can be used to determine the quantity of loci associated with the presence or absence of the chromosomal abnormality and the genetic status of one or more loci in the mixed sample. Detected levels of these nucleic acids can thus be used to determine the presence or absence of the chromosomal abnormality and the presence or absence of a polymorphism at one or more loci from a major source and/or a minor source within a mixed sample.

In another aspect, the present invention utilizes techniques that allow the identification of both CNVs and infectious agents in a mixed sample. This may be especially helpful to monitor patients in which the clinical outcome may be compromised by the presence of an infectious agent. For example, a patient that has undergone a transplant will likely be taking immunosuppressant medication, and so more prone to infection in general. Similarly, pregnant women have changes in their immune system and thus may be more susceptible to infection with pathogens that may have an adverse effect on the mother and/or fetus. Also, certain types of cancer are associated with infectious agents (e.g., liver cancer associated with hepatitis B and C infections, cervical cancer associated with human papilloma virus infection), and identification of the infectious agents may be informative in predicting clinical outcome or determining the preferred course of medical treatment for the patient.

Thus, in certain aspects, the invention provides an assay system for detection of the presence or absence of genetic copy number variation (CNV) of a genomic region and the presence or absence of an infectious agent in a mixed sample using a single assay, the assay comprising the steps of: introducing a first set of fixed sequence oligonucleotides to a mixed sample under conditions that allow the fixed sequence oligonucleotides to specifically hybridize to complementary regions on one or more loci in or associated with a genomic region; introducing a second set of fixed sequence oligonucleotides to the mixed sample under conditions that allow the fixed sequence oligonucleotides to specifically hybridize to complementary regions in nucleic acids indicative of an infectious agent; ligating the hybridized oligonucleotides to create a contiguous ligation product complementary to the nucleic acids; amplifying the contiguous ligation product to create amplification products; and detecting the amplification products. The detection of the amplification products correlates to copy number of the genomic region and the presence or absence of an infectious agent in the mixed sample.

In other certain aspects. The invention provides an assay system for detection of the presence or absence of copy number variation (CNV) of a genomic region, the presence or absence of one or more polymorphisms, and the presence or absence of an infectious agent in a mixed sample from an individual using a single assay, the assay comprising the steps of: introducing a first set of fixed sequence oligonucleotides to a mixed sample under conditions that allow the fixed sequence oligonucleotides to specifically hybridize to complementary regions on one or more loci in or associated with a genomic region; introducing a second set of fixed sequence oligonucleotides to the mixed sample under conditions that allow the fixed sequence oligonucleotides to specifically hybridize to complementary regions on one or more loci with a putative polymorphism; introducing a third set of fixed sequence oligonucleotides to the mixed sample under conditions that allow the fixed sequence oligonucleotides to specifically hybridize to complementary regions in nucleic acids indicative of an infectious agent; ligating the hybridized oligonucleotides to create a contiguous ligation product complementary to the nucleic acids; amplifying the contiguous ligation product to create amplification products; and detecting the amplification products. The detection of the amplification products correlates to copy number of the genomic region, the presence or absence of a polymorphism at one or more loci, and the presence or absence of an infectious agent in the mixed sample.

In these aspects, the assays can also comprise introducing one or more bridging oligonucleotides under conditions that allow the bridging oligonucleotides to specifically hybridize to complementary regions in the nucleic acids, wherein the one or more bridging oligonucleotides are complementary to a region of the nucleic acids between the regions complementary to the fixed sequence oligonucleotides of each set.

In another general aspect, the assay system employs a method for determining the presence or absence of a chromosomal abnormality associated with CNV in a genomic region, comprising the steps of amplifying one or more selected loci from a first chromosome of interest in a mixed sample; amplifying one or more selected loci from a second chromosome of interest in the mixed sample, determining the relative frequency of the selected regions from the first and second chromosomes of interest, comparing the relative frequency of the selected regions from the first and second chromosomes of interest, and identifying the presence or absence of an abnormality based on the compared relative frequencies of the selected regions. Preferably, two or more nucleic acids regions are selected from each chromosome, and more preferably five or more loci are selected from each chromosome.

In yet another general aspect, the assay system employs a method for determination of the presence or absence of an aneuploidy in a mixed sample from an individual, comprising the steps of amplifying two or more selected loci in the cfDNA corresponding to a first chromosome of interest in a mixed sample; amplifying two or more selected loci in the cfDNA corresponding to a second chromosome of interest in the mixed sample, determining the relative frequency of the selected regions from the first and second chromosomes of interest, comparing the relative frequency of the selected regions from the first and second chromosomes of interest, and identifying the presence or absence of an aneuploidy based on the compared relative frequencies of the selected regions. In a specific aspect, the loci of the first and second chromosomes are amplified in a single reaction, and preferably in a single reaction contained within a single vessel.

Preferably, the assay system detects the presence or absence of loci in samples that can be easily obtained from a subject, such as blood, plasma, serum and the like. In one general aspect, the assay system utilizes detection of selected regions in cfDNA in a mixed sample. In one more specific aspect, the assay system utilizes detection of selected regions in cfDNA of a mixed sample from an individual to identify the presence or absence of CNVs in a genomic region and the presence or absence of a polymorphism in one or more loci. Copy number within a genomic region can be determined based on detection of quantities of selected loci and comparison to the quantities of selected loci from another genomic region and/or to the quantities of selected loci from a reference genomic region. In a particular aspect, the ratio of the frequencies of the nucleic acid are compared to a reference mean ratio that has been determined for a statistically significant population of genetically "normal" subjects, i.e. subjects that do not have a CNV associated with the particular loci interrogated in the assay system.

In a preferred aspect of the invention, the amplification products corresponding to the selected nucleic acids are isolated as individual molecules for analysis of the selected loci. These individual amplification products are isolated from one another, and preferably physically isolated (e.g., on a substrate or in individual vessels). The individual molecules may be further amplified following isolation to make multiple, identical copies of the amplification product, a portion thereof, or a nucleic acid complementary to the amplification product or a portion thereof. The detection of the individual molecules or the amplification product may be done through sequencing.

In some aspects, the ligation product is not amplified, but rather is directly detected following hybridization, e.g., using single molecule sequencing techniques.

Thus, in a specific aspect, the invention provides an assay system for detection of the presence or absence of a chromosomal abnormality and polymorphisms in one or more loci in a mixed sample using a single assay, the assay comprising the steps of: introducing a first set of fixed sequence oligonucleotides to a mixed sample under conditions that allow the fixed sequence oligonucleotides to specifically hybridize to complementary regions in two or more nucleic acids corresponding to a particular chromosome; introducing a second set of fixed sequence oligonucleotides to the mixed sample under conditions that allow the fixed sequence oligonucleotides to specifically hybridize to complementary regions in nucleic acids with a putative polymorphism; introducing one or more bridging oligonucleotides under conditions that allow the bridging oligonucleotides to specifically hybridize to complementary regions in the nucleic acids, wherein one or more bridging oligonucleotides are complementary to a region of the nucleic acids between and immediately adjacent to the regions complementary to the fixed sequence oligonucleotides of each set; ligating the hybridized oligonucleotides to create contiguous ligation products complementary to the nucleic acids; amplifying the contiguous ligation products to create amplification products having the sequence of the loci; isolating individual amplification products; and analyzing the individual amplification products to determine the sequence of all or part of the individual amplification products. The analysis of the individual amplification products correlates to the presence or absence of a chromosomal abnormality and the genetic status of one or more loci in the mixed sample. For example, the levels of the nucleic acids corresponding to a particular chromosome may be compared by also using nucleic acids corresponding to another chromosome, or they may be compared to reference levels for the chromosome being interrogated.

In a preferred aspect, the individual amplification products are analyzed through sequence determination. In other aspects, the individual amplification products are analyzed using hybridization techniques.

It is a feature of the present invention that copy number of the selected loci can be detected using non-polymorphic detection methods, i.e., detection methods that are not dependent upon the presence or absence of a particular polymorphism to identify the selected nucleic acid region. In a preferred aspect, the assay detection systems utilize non-polymorphic detection methods to "count" the relative numbers of selected loci present in a mixed sample. These numbers can be utilized to determine if, statistically, a mixed sample is likely to have a CNV in a genomic region in a major and/or minor source within the mixed sample. Similarly, these numbers can be utilized to determine, if statistically, nucleic acids from the major source and/or minor source has one or more polymorphisms. Such information can be used to identify a particular pathology or genetic disorder, to confirm a diagnosis or recurrence of a disease or disorder, to determine the prognosis of a disease or disorder, to assist in determining potential treatment options, etc.

In some aspects, the methods for determination of copy number variation of multiple selected loci from two or more chromosomes in a sample. The levels of the different selected loci corresponding to specific chromosomes can be individually quantified and compared to determine the presence or absence of a chromosomal aneuploidy in one or more cell source in a mixed sample. The individually quantified regions may undergo a normalization calculation or the data may be subjected to outlier exclusion prior to comparison to determine the presence or absence of an aneuploidy in a mixed sample.

In other aspects, the relative frequencies of the selected loci are used to determine a chromosome frequency of the first and second chromosomes of interest, and the presence or absence of an aneuploidy is based on the compared chromosome frequencies of the first and second chromosomes of interest.

In yet other aspects, the relative frequencies of the selected loci are used to determine a chromosome frequency of a chromosome of interest and a reference chromosome, and the presence or absence of an aneuploidy is based on the compared chromosome frequencies of the chromosome of interest and the reference chromosome.

In one particular aspect, the selected loci are isolated prior to detection. The selected loci can be isolated from the mixed sample using any means that selectively isolate the particular nucleic acids present in the mixed sample for analysis, e.g., hybridization, amplification or other form of sequence-based isolation of the nucleic acids from the mixed sample. Following isolation, the selected nucleic acids are individually distributed in a suitable detection format, e.g., on a microarray or in a flow cell, for determination of the sequence and/or relative quantities of each selected nucleic acid in the mixed sample. The relative quantities of the detected nucleic acids are indicative of the number of copies of chromosomes that correspond to the selected nucleic acids present in the mixed sample.

Following isolation and distribution of the selected nucleic acids in a suitable format, the selected sequences are identified, e.g., through sequence determination of the selected sequence.

In one specific aspect, the invention provides an assay system for detection of the presence or absence of a fetal aneuploidy, comprising the steps of providing a mixed sample comprising maternal and fetal cfDNA, amplifying two or more selected loci from a first and second chromosome of interest in the mixed sample, amplifying two or more selected loci from the first and second chromosome of interest in the mixed sample, determining the relative frequency of the selected regions from the chromosomes of interest, comparing the relative frequency of the selected loci from the first and second chromosomes of interest, and identifying the presence or absence of a fetal aneuploidy based on the compared relative frequencies of the selected loci.

In some specific aspects, the relative frequencies of the loci from a genomic region are individually calculated, and the relative frequencies of the individual loci are compared to determine the presence or absence of a chromosomal abnormality. In other specific aspects, the relative frequencies of the selected loci are used to determine a chromosome frequency of a first and second chromosome of interest and a reference chromosome, and the copy number variation for the chromosome or a genomic region of the chromosome is based on the compared chromosome frequencies of the first and second chromosomes of interest.

The mixed sample used for analysis can be obtained or derived from any sample which contains the nucleic acid of interest to be analyzed using the assay system of the invention. For example, a mixed sample may be from any maternal fluid which comprises both maternal and fetal cell free nucleic acids, including but not limited to maternal plasma, maternal serum, or maternal blood. A mixed sample from a transplant patient would be any fluid or tissue which contains cell free nucleic acids from both the donor cells and the cells of the patient. A mixed sample from a patient with a malignancy would contain cell free nucleic acids from the patient's normal, healthy tissue as well as cell free nucleic acids from the cancerous cells.

Although preferably the assay system is used to detect cfDNA in a mixed sample, in certain aspects the DNA of interest to be analyzed using the assay system of the invention comprises DNA directly from the different cell types rather than from a mixed sample containing DNA from the major and minor cell types. Such samples can be obtained from various sources depending upon the target DNA. For example, fetal cells for analysis can be derived from samples such as amniotic fluid, placenta (e.g., the chorionic villi), and the like. Samples of donor organs can be obtained in an individual by biopsy. Infectious organisms can be isolated directly from an individual and analyzed following isolation. DNA can be extracted from cancerous cells or tissues and used for analysis.

It is a feature of the invention that the nucleic acids analyzed in the assay system do not require polymorphic differences between the cell sources to determine frequency, and thus potential CNVs, in loci from a mixed sample. It is another feature of the invention that the substantial majority of the nucleic acids isolated from the mixed sample and detected in the assay system provide information relevant to the presence, quantity and/or polymorphic nature of a particular locus in the mixed sample. This ensures that the majority of nucleic acids analyzed in the assay system of the invention are informative.

In some aspects, multiple loci are determined for each genomic region under interrogation, and the quantity of the selected regions present in the mixed sample are individually summed to determine the relative frequency of a locus in a mixed sample. This includes determination of the frequency of the locus for the combined maternal and fetal DNA present in the mixed sample. Preferably, the determination does not require a distinction between the DNA from separate sources, although in certain aspects this information may be obtained in addition to the information of relative frequencies in the sample as a whole.

In preferred aspects, selected nucleic acids corresponding to informative loci are detected and summed to determine the relative frequency of a genomic region in the mixed sample. Frequencies that are higher than expected for loci from a first genomic region when compared to the loci from a second locus in a mixed sample is indicative of a CNV of the first genomic region in the mixed sample.

Comparison of genomic regions can be a comparison of part or all of a chromosome. For example, the genomic region detected for CNV may be an entire chromosome in the fetus (e.g., chromosomes 18 and 21), where the likelihood of both being aneuploid is minimal. This can also be a comparison of chromosomes where one is putatively aneuploid (e.g., chromosome 21) and the other acts as a reference chromosome (e.g. an autosome such as chromosome 2). In yet other aspects, the comparison may utilize two or more chromosomes that are putatively aneuploid and one or more reference chromosomes.

In one aspect, the assay system of the invention analyzes multiple nucleic acids representing selected loci on chromosomes of interest, and the relative frequency of each selected locus from the sample is analyzed to determine a relative chromosome frequency for each particular chromosome of interest in the sample. The chromosomal frequency of two or more chromosomes or portions thereof is then compared to statistically determine whether a chromosomal abnormality exists.

In another aspect, the assay system of the invention analyzes multiple nucleic acids representing selected loci on chromosomes of interest, and the relative frequency of each selected nucleic acid from the sample is analyzed and independently quantified to determine a relative amount for each selected locus in the sample. The sum of the loci in the sample is compared to statistically determine whether a CNV exists for one or more loci in a genomic region of one cell source in a mixed sample.

In another aspect, subsets of loci on each chromosome are analyzed to determine whether a chromosomal abnormality exists. The loci frequency can be summed for a particular chromosome, and the summations of the loci used to determine aneuploidy. This aspect of the invention sums the frequencies of the individual loci in each genomic region and then compares the sum of the loci on a genomic region of one chromosome against a genomic region of another chromosome to determine whether a chromosomal abnormality exists. The subsets of loci can be chosen randomly but with sufficient numbers of loci to yield a statistically significant result in determining whether a chromosomal abnormality exists. Multiple analyses of different subsets of loci can be performed within a mixed sample to yield more statistical power. In another aspect, particular loci can be selected that are known to have less variation between samples, or by limiting the data used for determination of chromosomal frequency, e.g., by ignoring the data from loci with very high or very low frequency within a sample.

In a particular aspect, the measured quantities of one or more particular loci are normalized to account for differences in loci quantity in the sample. This can be done by normalizing for known variation from sources such as the assay system (e.g., temperature, reagent lot differences), underlying biology of the sample (e.g., nucleic acid content), operator differences, or any other variables.

In certain specific aspects, determining the relative percentage of nucleic acids from the minor source in a mixed sample may be beneficial in performing the assay system, as it will provide important information on the relative statistical presence of loci that may be indicative of copy number variation within the minor source in that sample. Determining the loci contributed to the mixed sample from the minor source can provide information used to calculate the statistically significant differences in frequencies for genomic regions of interest. Such loci could thus provide two forms of information in the assay—allelic information can be used for determining the percent minor cell contribution in a mixed sample and a summation of the allelic information can be used to determine the relative overall frequency of that locus in a mixed sample. The allelic information is not needed to determine the relative overall frequency of that locus.

In another specific aspect, the assay system of the invention can be utilized to determine potential mosaicism in a cell population, and whether further confirmatory tests should be undertaken to confirm the identification of mosaicism in the major and/or minor source. In certain instances, determination of the percent nucleic acids from the minor source in a mixed sample could assist in quantification of the estimated level of mosaicism. Mosaicism could be subsequently confirmed using other testing methods that could distinguish mosaic full or partial aneuploidy in specific cells or tissue.

In yet another specific aspect, the assay system of the invention can be utilized to determine contamination in a sample, with the minor species representing a contaminant species.

In another aspect, the oligonucleotides for a given selected nucleic acid can be connected at the non-sequence specific ends such that a circular or unimolecular probe may bind thereto. In this aspect, the 3' end and the 5' end of the circular probe binds to the selected locus and at least one universal amplification region is present in the non-selected specific sequence of the circular probe.

It is an important feature of the assay that the amplification products are analyzed directly without the need for enrichment of polymorphic regions from the initial mixed sample. Thus, the current invention allows detection of both CNV and polymorphisms from a maternal sample without an intervening polymorphic enrichment step prior to sequence determination of the selected loci.

It is another important feature of the assay that both CNV and polymorphism detection are determined using a targeted approach of selected amplification and detection. This allows the majority of information gathered in the assay to be useful for the determination of the CNV and/or polymorphism interrogated in the locus of interest, and obviates the need to generate sequence reads that must be aligned with a reference sequence.

These and other aspects, features and advantages will be provided in more detail as described herein.

BRIEF DESCRIPTION OF THE FIGURES

FIG. 7 is a summary of patient and sample information and data for a subset of a second cohort of pregnant subjects.

DEFINITIONS

Figure 1:
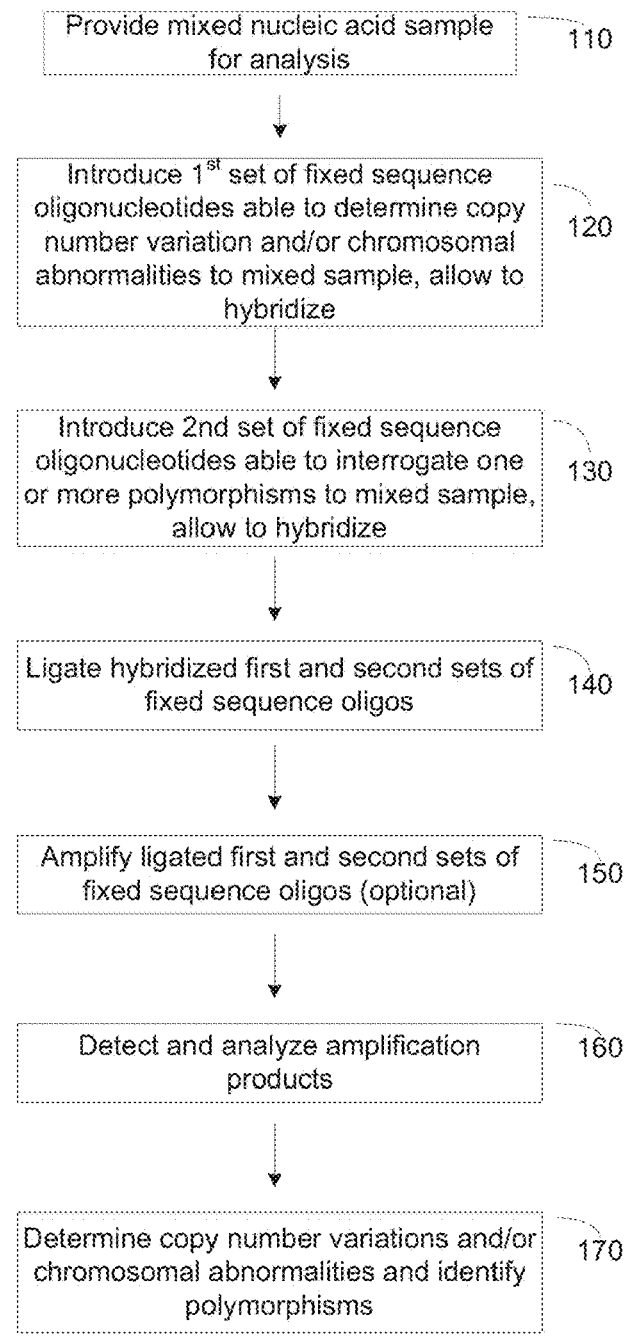
FIG. 1 is a simplified flow chart of the general steps utilized in the assay systems of the invention.

The terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated.

The term "amplified nucleic acid" is any nucleic acid molecule whose amount has been increased at least two fold by any nucleic acid amplification or replication method performed in vitro as compared to its starting amount in a mixed sample.

The term "amplification product" as used herein refers to the product resulting from an amplification reaction using the contiguous ligation product as a template, or the product resulting from an amplification reaction using a molecule complementary to the contiguous ligation product as a template.

The term "chromosomal abnormality" refers to any genetic variation that affects all or part of a chromosome larger than a single locus. The genetic variants may include but not be limited to any CNV such as duplications or deletions, translocations, inversions, and mutations. Examples of chromosomal abnormalities include, but are not limited to, Down Syndrome (Trisomy 21), Edwards Syndrome (Trisomy 18), Patau Syndrome (Trisomy 13), Klinefelter's Syndrome (XXY), Triple X syndrome, XYY syndrome, Trisomy 8, Trisomy 16, Turner Syndrome, Robertsonian translocation, DiGeorge Syndrome and Wolf-Hirschhorn Syndrome.

The terms "complementary" or "complementarity" are used in reference to nucleic acid molecules (i.e., a sequence of nucleotides) that are related by base-pairing rules. Complementary nucleotides are, generally, A and T (or A and U), or C and G. Two single stranded RNA or DNA molecules are said to be substantially complementary when the nucleotides of one strand, optimally aligned and with appropriate nucleotide insertions or deletions, pair with at least about 90% to about 95% complementarity, and more preferably from about 98% to about 100% complementarity, and even more preferably with 100% complementarity. Alternatively, substantial complementarity exists when an RNA or DNA strand will hybridize under selective hybridization conditions to its complement. Selective hybridization conditions include, but are not limited to, stringent hybridization conditions. Stringent hybridization conditions will typically include salt concentrations of less than about 1 M, more usually less than about 500 mM and preferably less than about 200 mM. Hybridization temperatures are generally at least about 2° C. to about 6° C. lower than melting temperatures ($T_m$).

The term "copy number variation" or "CNV" as used interchangeably herein are alterations of the DNA of a genome that results in a cell having an abnormal number of copies of one or more loci in the DNA. CNVs that are clinically relevant can be limited to a single gene or include a contiguous set of genes. A CNV can also correspond to relatively large regions of the genome that have been deleted, inverted or duplicated on certain chromosomes, up to an including one or more additional copies of a complete chromosome. The term CNV as used herein does not refer to any sequence-related information, but rather to quantity or "counts" of genetic regions present in a sample.

The term "correction index" refers to an index that may contain additional nucleotides that allow for identification and correction of amplification, sequencing or other experimental errors including the detection of deletion, substitution, or insertion of one or more bases during sequencing as well as nucleotide changes that may occur outside of sequencing such as oligo synthesis, amplification, and any other aspect of the assay. These correction indices may be stand-alone indices that are separate sequences, or they may be embedded within other regions to assist in confirming accuracy of the experimental techniques used, e.g., a correction index may be a subset of sequences used for universal amplification or a subset of nucleotides of a sample locus.

The term "diagnostic tool" as used herein refers to any composition or assay of the invention used in combination as, for example, in a system in order to carry out a diagnostic test or assay on a patient sample.

The term "disease trait" refers to a monogenic or polygenic trait associated with a pathological condition, e.g., a disease, disorder, syndrome or predisposition.

The term "hybridization" generally means the reaction by which the pairing of complementary strands of nucleic acid occurs. DNA is usually double-stranded, and when the strands are separated they will re-hybridize under the appropriate conditions. Hybrids can form between DNA-DNA, DNA-RNA or RNA-RNA. They can form between a short strand and a long strand containing a region complementary to the short one. Imperfect hybrids can also form, but the more imperfect they are, the less stable they will be (and the less likely to form).

The term "informative locus" as used herein refers to a locus that is homozygous for one cell source and heterozygous for a second cell source on a particular chromosome or portion of a chromosome interrogated for purposes of determining a CNV of all or part of that chromosome. Informative loci for use in the assay system of the invention include loci used for interrogation of a reference chromosome as well as loci used for interrogation of a chromosome that is putatively aneuploid in a cell source. Informative loci can also distinguish copy number of loci in cell sources from different individuals within a single individual (e.g., detection of transplant donor cells in a transplant recipient or detection of a fetal DNA within a maternal mixed sample).

The terms "locus" and "loci" as used herein refer to a locus of known location in a genome.

The term "major source" refers to a source of nucleic acids in a sample from an individual that is representative of the predominant genomic material in that individual.

The term "maternal sample" as used herein refers to any sample taken from a pregnant mammal which comprises both fetal and maternal cell free genomic material (e.g., DNA). Preferably, maternal samples for use in the invention are obtained through relatively non-invasive means, e.g., phlebotomy or other standard techniques for extracting peripheral samples from a subject.

The term "melting temperature" or $T_m$ is commonly defined as the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+16.6(\log 10[Na+])$ $0.41(\%[G+C])-675/n-1.0$ m, when a nucleic acid is in aqueous solution having cation concentrations of 0.5 M or less, the (G+C) content is between 30% and 70%, n is the number of bases, and m is the percentage of base pair mismatches (see, e.g., Sambrook J et al., *Molecular Cloning, A Laboratory Manual,* 3rd Ed., Cold Spring Harbor Laboratory Press (2001)). Other references include more sophisticated computations, which take structural as well as sequence characteristics into account for the calculation of $T_m$.

"Microarray" or "array" refers to a solid phase support having a surface, preferably but not exclusively a planar or substantially planar surface, which carries an array of sites containing nucleic acids such that each site of the array comprises substantially identical or identical copies of oligonucleotides or polynucleotides and is spatially defined and not overlapping with other member sites of the array; that is, the sites are spatially discrete. The array or microarray can also comprise a non-planar interrogatable structure with a surface such as a bead or a well. The oligonucleotides or polynucleotides of the array may be covalently bound to the solid support, or may be non-covalently bound. Conventional microarray technology is reviewed in, e.g., Schena, Ed., *Microarrays: A Practical Approach*, IRL Press, Oxford (2000). "Array analysis", "analysis by array" or "analysis by microarray" refers to analysis, such as, e.g., sequence analysis, of one or more biological molecules using a microarray.

The term "minor source" refers to a source of nucleic acids within an individual that is present in limited amounts and which is distinguishable from the major source due to differences in its genomic makeup and/or expression. Examples of minor sources include, but are not limited to, fetal cells in a pregnant female, cancerous cells in a patient with a malignancy, cells from a donor organ in a transplant patient, nucleic acids from an infectious organism in an infected host, and the like.

The term "mixed sample" as used herein refers to any sample comprising cell free genomic material (e.g., DNA) from two or more cell types of interest, one being a major source and the other being a minor source within a single individual. Mixed samples include samples with genomic material from both a major and a minor source in an individual, which may be e.g., normal and atypical somatic cells, or cells that comprise genomes from two different individuals, e.g., a sample with both maternal and fetal genomic material or a sample from a transplant patient that comprises cells from both the donor and recipient. Mixed samples are preferably peripherally derived, e.g., from blood, plasma, serum, etc.

The term "monogenic trait" as used herein refers to any trait, normal or pathological, that is associated with a mutation or polymorphism in a single gene. Such traits include traits associated with a disease, disorder, or predisposition caused by a dysfunction in a single gene. Traits also include non-pathological characteristics (e.g., presence or absence of cell surface molecules on a specific cell type).

The term "non-maternal" allele means an allele with a polymorphism and/or mutation that is found in a fetal allele (e.g., an allele with a de novo SNP or mutation) and/or a paternal allele, but which is not found in the maternal allele.

By "non-polymorphic", when used with respect to detection of selected loci, is meant a detection of such locus, which may contain one or more polymorphisms, but in which the detection is not reliant on detection of the specific polymorphism within the region. Thus a selected locus may contain a polymorphism, but detection of the region using the assay system of the invention is based on occurrence of the region rather than the presence or absence of a particular polymorphism in that region.

As used herein "nucleotide" refers to a base-sugar-phosphate combination. Nucleotides are monomeric units of a nucleic acid sequence (DNA and RNA). The term nucleotide includes ribonucleoside triphosphates ATP, UTP, CTG, GTP and deoxyribonucleoside triphosphates such as dATP, dCTP, dITP, dUTP, dGTP, dTTP, or derivatives thereof. Such derivatives include, for example, [αS]dATP, 7-deaza-dGTP and 7-deaza-dATP, and nucleotide derivatives that confer nuclease resistance on the nucleic acid molecule containing them. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP.

According to the present invention, a "nucleotide" may be unlabeled or detectably labeled by well known techniques. Fluorescent labels and their attachment to oligonucleotides are described in many reviews, including Haugland, *Handbook of Fluorescent Probes and Research Chemicals*, 9th Ed., Molecular Probes, Inc., Eugene Oreg. (2002); Keller and Manak, *DNA Probes*, 2nd Ed., Stockton Press, New York (1993); Eckstein, Ed., *Oligonucleotides and Analogues: A Practical Approach*, IRL Press, Oxford (1991); Wetmur, *Critical Reviews in Biochemistry and Molecular Biology*, 26:227-259 (1991); and the like. Other methodologies applicable to the invention are disclosed in the following sample of references: Fung et al., U.S. Pat. No. 4,757,141; Hobbs, Jr., et al., U.S. Pat. No. 5,151,507; Cruickshank, U.S. Pat. No. 5,091,519; Menchen et al., U.S. Pat. No. 5,188,934; Begot et al., U.S. Pat. No. 5,366,860; Lee et al., U.S. Pat. No. 5,847,162; Khanna et al., U.S. Pat. No. 4,318,846; Lee et al., U.S. Pat. No. 5,800,996; Lee et al., U.S. Pat. No. 5,066,580: Mathies et al., U.S. Pat. No. 5,688,648; and the like. Labeling can also be carried out with quantum dots, as disclosed in the following patents and patent publications: U.S. Pat. Nos. 6,322,901; 6,576,291; 6,423,551; 6,251,303; 6,319,426; 6,426,513; 6,444,143; 5,990,479; 6,207,392; 2002/0045045; and 2003/0017264. Detectable labels include, for example, radioactive isotopes, fluorescent labels, chemiluminescent labels, bioluminescent labels and enzyme labels. Fluorescent labels of nucleotides may include but are not limited fluorescein, 5-carboxyfluorescein (FAM), 2'7'-dimethoxy-4'5'-dichloro-6-carboxyfluorescein (JOE), rhodamine, 6-carboxyrhodamine (R6G), N,N,N',N'-tetramethyl-6-carboxyrhodamine (TAMRA), 6-carboxy-X-rhodamine (ROX), 4-(4'dimethylaminophenylazo) benzoic acid (DABCYL), Cascade Blue, Oregon Green, Texas Red, Cyanine and 5-(2'-aminoethyl)aminonaphthalene-1-sulfonic acid (EDANS). Specific examples of fluorescently labeled nucleotides include [R6G]dUTP, [TAMRA]dUTP, [R110]dCTP, [R6G]dCTP, [TAMRA] dCTP, [JOE]ddATP, [R6G]ddATP, [FAM]ddCTP, [R110] ddCTP, [TAMRA]ddGTP, [ROX]ddTTP, [dR6G]ddATP, [dR110]ddCTP, [dTAMRA]ddGTP, and [dROX]ddTTP available from Perkin Elmer, Foster City, Calif. FluoroLink DeoxyNucleotides, FluoroLink Cy3-dCTP, FluoroLink Cy5-dCTP, FluoroLink FluorX-dCTP, FluoroLink Cy3-dUTP, and FluoroLink Cy5-dUTP available from Amersham, Arlington Heights, Ill.; Fluorescein-15-dATP, Fluorescein-12-dUTP, Tetramethyl-rodamine-6-dUTP, IR770-9-dATP, Fluorescein-12-ddUTP, Fluorescein-12-UTP, and Fluorescein-15-2'-dATP available from Boehringer Mannheim, Indianapolis, Ind.; and Chromosomee Labeled Nucleotides, BODIPY-FL-14-UTP, BODIPY-FL-4-UTP, BODIPY-TMR-14-UTP, BODIPY-TMR-14-dUTP, BODIPY-TR-14-UTP, BODIPY-TR-14-dUTP, Cascade Blue-7-UTP, Cascade Blue-7-dUTP, fluorescein-12-UTP, fluorescein-12-dUTP, Oregon Green 488-5-dUTP, Rhodamine Green-5-UTP, Rhodamine Green-5-dUTP, tetramethylrhodamine-6-UTP, tetramethylrhodamine-6-dUTP, Texas Red-5-UTP, Texas Red-5-dUTP, and Texas Red-12-dUTP available from Molecular Probes, Eugene, Oreg.

The terms "oligonucleotides" or "oligos" as used herein refer to linear oligomers of natural or modified nucleic acid monomers, including deoxyribonucleotides, ribonucleotides, anomeric forms thereof, peptide nucleic acid monomers (PNAs), locked nucleotide acid monomers (LNA), and the like, or a combination thereof, capable of specifically binding to a single-stranded polynucleotide by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides ranging in size from a few monomeric units, e.g., 8-12, to several tens of monomeric units, e.g., 100-200 or more. Suitable nucleic acid molecules may be prepared by the phosphoramidite method described by Beaucage and Carruthers (Tetrahedron Lett., 22:1859-1862 (1981)), or by the triester method according to Matteucci, et al. (J. Am. Chem. Soc., 103:3185 (1981)), both incorporated herein by reference, or by other chemical methods such as using a commercial automated oligonucleotide synthesizer.

The term "polygenic trait" as used herein refers to any trait, normal or pathological, that is associated with a mutation or polymorphism in more than a single gene. Such traits include traits associated with a disease, disorder, syndrome or predisposition caused by a dysfunction in two or more genes. Traits also include non-pathological characteristics associated with the interaction of two or more genes.

As used herein the term "polymerase" refers to an enzyme that links individual nucleotides together into a long strand, using another strand as a template. There are two general types of polymerase—DNA polymerases, which synthesize DNA, and RNA polymerases, which synthesize RNA. Within these two classes, there are numerous sub-types of polymerases, depending on what type of nucleic acid can function as template and what type of nucleic acid is formed.

As used herein "polymerase chain reaction" or "PCR" refers to a technique for replicating a specific piece of selected DNA in vitro, even in the presence of excess non-specific DNA. Primers are added to the selected DNA, where the primers initiate the copying of the selected DNA using nucleotides and, typically, Taq polymerase or the like. By cycling the temperature, the selected DNA is repetitively denatured and copied. A single copy of the selected DNA, even if mixed in with other, random DNA, can be amplified to obtain billions of replicates. The polymerase chain reaction can be used to detect and measure very small amounts of DNA and to create customized pieces of DNA. In some instances, linear amplification methods may be used as an alternative to PCR.

The term "polymorphism" as used herein refers to any genetic changes or sequence variants in a locus, including but not limited to single nucleotide polymorphisms (SNPs), methylation differences, short tandem repeats (STRs), single gene polymorphisms, point mutations, trinucleotide repeats, indels and the like.

Generally, a "primer" is an oligonucleotide used to, e.g., prime DNA extension, ligation and/or synthesis, such as in the synthesis step of the polymerase chain reaction or in the primer extension techniques used in certain sequencing reactions. A primer may also be used in hybridization techniques as a means to provide complementarity of a locus to a capture oligonucleotide for detection of a specific locus.

The term "research tool" as used herein refers to any composition or assay of the invention used for scientific enquiry, academic or commercial in nature, including the development of pharmaceutical and/or biological therapeutics. The research tools of the invention are not intended to be therapeutic or to be subject to regulatory approval; rather, the research tools of the invention are intended to facilitate research and aid in such development activities, including any activities performed with the intention to produce information to support a regulatory submission.

The term "sample index" refers generally to a series of unique nucleotides (i.e., each sample index is unique to a sample in a multiplexed assay system for analysis of multiple samples). The sample index can thus be used to assist in locus identification for multiplexing of different samples in a single reaction vessel, such that each sample can be identified based on its sample index. In a preferred aspect, there is a unique sample index for each sample in a set of samples, and the samples are pooled during sequencing. For example, if twelve samples are pooled into a single sequencing reaction, there are at least twelve unique sample indexes such that each sample is labeled uniquely.

The term "selected locus" as used herein refers to a locus corresponding to a loci interrogated, e.g., for copy number, the presence or absence of one or more polymorphism, presence or absence of an infectious organism, etc. Such selected loci may be directly isolated and amplified from the sample for detection, e.g., based on hybridization and/or other sequence-based techniques, or they may be amplified using the sample as a template prior to detection of the sequence. Nucleic acids regions for use in the assay systems of the present invention may be selected on the basis of DNA level variation between individuals, based upon specificity for a particular chromosome, based on CG content and/or required amplification conditions of the selected loci, or other characteristics that will be apparent to one skilled in the art upon reading the present disclosure.

The terms "sequencing", "sequence determination" and the like as used herein refers generally to any and all biochemical methods that may be used to determine the order of nucleotide bases in a nucleic acid.

The term "specifically binds", "specific binding" and the like as used herein, when referring to a binding partner (e.g., a nucleic acid probe or primer, antibody, etc.) that results in the generation of a statistically significant positive signal under the designated assay conditions. Typically the interaction will subsequently result in a detectable signal that is at least twice the standard deviation of any signal generated as a result of undesired interactions (background).

The term "status" as used herein in relationship to a gene refers to the sequence status of the alleles of a particular gene, including the coding regions and the non-coding regions that affect the translation and/or protein expression from that gene. The status of a gene associated with an autosomal dominant disease such as achondroplasia (e.g., the gene encoding the fibroblast growth factor receptor) or Huntington's disease (e.g., the Huntingtin gene), or for an X-linked disease in the case of a male fetus, can be classified as affected i.e., one allele possesses mutation(s) that is causative of the diseases or disorder, or non-affected, i.e. both alleles lack such mutations(s). The status of a gene associated with an autosomal recessive disease or a maternal gene associated with an X-linked recessive disorder, may be classified as affected, i.e., both alleles possess mutation(s) causative of the diseases or disorder; carrier, i.e. one allele possesses mutation(s) causative of the diseases or disorder; or non-affected, i.e. both alleles lack such mutations(s). The status of a gene may also indicate the presence or absence of a particular allele associated with a risk of developing a polygenic disease, e.g., a polymorphism that is protective against a particular disease or disorder or a polymorphism associated with an enhanced risk for a particular disease or disorder.

DETAILED DESCRIPTION OF THE INVENTION

The assay systems and methods described herein may employ, unless otherwise indicated, conventional techniques and descriptions of molecular biology (including recombinant techniques), cell biology, biochemistry, microarray and sequencing technology, which are within the skill of those who practice in the art. Such conventional techniques include polymer array synthesis, hybridization and ligation of oligonucleotides, sequencing of oligonucleotides, and detection of hybridization using a label. Specific illustrations of suitable techniques can be had by reference to the examples herein. However, equivalent conventional procedures can, of course, also be used. Such conventional techniques and descriptions can be found in standard laboratory manuals such as Green, et al., Eds., *Genome Analysis: A Laboratory Manual Series* (Vols. I-IV) (1999); Weiner, et al., Eds., *Genetic Variation: A Laboratory Manual* (2007); Dieffenbach, Dveksler, Eds., *PCR Primer: A Laboratory Manual* (2003); Bowtell and Sambrook, *DNA Microarrays:*

*A Molecular Cloning Manual* (2003); Mount, *Bioinformatics: Sequence and Genome Analysis* (2004); Sambrook and Russell, *Condensed Protocols from Molecular Cloning: A Laboratory Manual* (2006); and Sambrook and Russell, *Molecular Cloning: A Laboratory Manual* (2002) (all from Cold Spring Harbor Laboratory Press); Stryer, L., *Biochemistry* (4th Ed.) W.H. Freeman, New York (1995); Gait, "*Oligonucleotide Synthesis: A Practical Approach*" IRL Press, London (1984); Nelson and Cox, *Lehninger, Principles of Biochemistry*, $3^{rd}$ Ed., W. H. Freeman Pub., New York (2000); and Berg et al., *Biochemistry*, $5^{th}$Ed., W.H. Freeman Pub., New York (2002), all of which are herein incorporated by reference in their entirety for all purposes.

Before the present compositions, research tools and methods are described, it is to be understood that this invention is not limited to the specific methods, compositions, targets and uses described, as such may, of course, vary. It is also to be understood that the terminology used herein is for the purpose of describing particular aspects only and is not intended to limit the scope of the present invention, which will be limited only by appended claims.

It should be noted that as used herein and in the appended claims, the singular forms "a," "an," and "the" include plural referents unless the context clearly dictates otherwise. Thus, for example, reference to "a locus" refers to one, more than one, or mixtures of such regions, and reference to "an assay" includes reference to equivalent steps and methods known to those skilled in the art, and so forth.

Where a range of values is provided, it is to be understood that each intervening value between the upper and lower limit of that range—and any other stated or intervening value in that stated range—is encompassed within the invention. Where the stated range includes upper and lower limits, ranges excluding either of those included limits are also included in the invention.

Unless expressly stated, the terms used herein are intended to have the plain and ordinary meaning as understood by those of ordinary skill in the art. The following definitions are intended to aid the reader in understanding the present invention, but are not intended to vary or otherwise limit the meaning of such terms unless specifically indicated. All publications mentioned herein are incorporated by reference for the purpose of describing and disclosing the formulations and methodologies that are described in the publication and which might be used in connection with the presently described invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

The Invention in General

The present invention provides single assay systems with the ability to detect copy number variations, polymorphisms and infectious disease in a mixed sample from a single individual. The assay methods comprise identifying the copy number of selected loci (including multiple loci that are associated with chromosomal abnormalities) and detection of polymorphisms that are found in a major source and/or a minor source. These methods are useful for any mixed sample containing genomic material (e.g., DNA) from a major and a minor source that are present in a single individual.

The use of selected loci in the assay methods of the invention provides amplification of loci for detection of copy number variation. A distinct advantage of the invention is that the selected loci corresponding to copy number variation and/or polymorphisms can be further analyzed using a variety of detection and quantification techniques, including but not limited to hybridization techniques, digital PCR and high throughput sequencing determination techniques. Selection probes can be designed against any number of loci for any chromosome. Although amplification of the mixed sample prior to the identification and quantification of the selection nucleic acids regions is not mandatory, limited amplification prior to detection can be performed, in particular if the initial amounts of nucleic acid are limited.

FIG. 1 is a simplified flow chart of the general steps utilized in the assay systems of the invention. FIG. 1 shows method 100, where in a first step 110, a mixed nucleic acid sample is provided for analysis. The mixed sample can be prepared from virtually any sample as such techniques are known to those of skill in the art (see, e.g., Tietz Textbook of Clinical Chemistry and Molecular Diagnostics, 4th Ed., Chapter 2, Burtis, C. Ashwood E. and Bruns, D, eds. (2006); Chemical Weapons Convention Chemicals Analysis: Sample Collection, Preparation and Analytical Methods, Mesilaakso, M., ed., (2005); Pawliszyn, J., Sampling and Sample Preparation for Field and Laboratory, (2002); Venkatesh Iyengar, G., et al., Element Analysis of Biological Samples: Principles and Practices (1998); Drielak, S., Hot Zone Forensics: Chemical, Biological, and Radiological Evidence Collection (2004); Wells, D., High Throughput Bioanalytical Sample Preparation (Progress in Pharmaceutical and Biomedical Analysis) (2002)), each of which is incorporated by reference). Depending on the type of mixed sample chosen, additional processing and/or purification steps may be performed to obtain nucleic acid fragments of a desired purity or size, using processing methods including but not limited to sonication, nebulization, gel purification, PCR purification systems, nuclease cleavage, or a combination of these methods. In a preferred aspect, samples comprising cell-free DNA (cfDNA) are used.

At step 120, a first set of fixed sequence oligonucleotides are introduced to the mixed nucleic acid sample, under conditions that allow the first set of fixed sequence oligonucleotides to hybridize to the mixed nucleic acid sample. The first set of fixed sequence oligonucleotides comprise nucleic acid sequences that are complementary to a selected locus or loci in the mixed sample, which as will be described in detail herein are useful in determining copy number variations and/or chromosomal abnormalities. The nucleic acid sequences capable of determining copy number variations and/or chromosomal abnormalities include sequences that allow for identification of chromosomal abnormalities such as duplications or deletions, aneuploidies, translocations, or inversions.

At step 130, a second set of fixed sequence oligonucleotides are introduced to the mixed nucleic acid sample and first set of fixed sequence oligonucleotides under conditions that allow the second set of fixed sequence oligonucleotides to hybridize to the mixed nucleic acid sample. The second set of fixed sequence oligonucleotides comprise nucleic acid sequences that are complementary to a selected locus or loci in the mixed sample, able to detect polymorphisms. Washing steps optionally may be included between steps 120 and 130, and 130 and 140.

Although the invention is described as the two sets of oligos introduced to the mixed sample sequentially, the order of the sets may be reversed from that described in the figures or, in preferred aspects, they can be introduced simultaneously.

At step 140, first and second sets of fixed sequence oligonucleotides that have hybridized to adjacent regions of the selected loci in the mixed sample are ligated, and at step 150, the ligated oligonucleotides are amplified. The ligated and amplified oligonucleotides are then detected and analyzed, which allows for determination of copy number variations or chromosomal abnormalities and identification of polymorphisms at step 160.

The sets of fixed sequence nucleic acids are designed to hybridize to at least two separate regions in a selected locus. In preferred aspects, two or more separate oligos are used to hybridize to these regions to provide adjacent nucleic acids complementary to the selected locus. In some aspects, however, a single probe can be used which comprises two or more distinct non-adjacent regions that are complementary to the selected loci including precircular probes such as so-called "padlock probes" or "molecular inversion probes (MIPs)".

The present invention provides an improved system over more random techniques such as massively parallel sequencing, shotgun sequencing, and the use of random digital PCR which have been used by others to detect CNVs. These aforementioned approaches rely upon sequencing of all or a statistically significant population of DNA fragments in a sample, followed by mapping of these fragments or otherwise associating the fragments to their appropriate chromosomes. The identified fragments are then compared against each other or against some other reference (e.g., normal chromosomal makeup) to determine CNVs on particular chromosomes. These methods are inherently inefficient as compared to the present invention, as the primary chromosomes of interest only constitute a minority of data that is generated from the detection of such DNA fragments in the mixed samples.

The assays of the present invention provide targeted detection of selected loci, which provides information on both the content of the selected region (i.e., presence of a polymorphic region) and information on the frequency of the detected region in a sample (with or without detecting any putative polymorphisms in that region). This key feature provides the ability to detect both copy number of selected regions and the presence or absence of polymorphisms in a selected region as a single data set from performance of a multiplexed assay of the invention.

Techniques that are dependent upon a very broad sampling of DNA in a sample provide a very broad coverage of the DNA analyzed, but in fact are sampling the DNA contained within a sample on a 1× or less basis (i.e., subsampling). In contrast, the selective amplification used in the present assays are specifically designed to provide depth of coverage of particular loci of interest, and provide a "super-sampling" of such selected loci with an average sequence coverage of preferably 2× or more, more preferably sequence coverage of 100× of more, even more preferably sequence coverage of 1000× or more of the selected loci (including from the one or more minor sources) present in the initial mixed sample.

A distinct advantage of the invention is that the ligation products resulting from the assays corresponding to chromosomal abnormalities and/or chromosomal abnormalities and polymorphisms can be analyzed using a variety of detection and quantification techniques, including but not limited to hybridization techniques, digital PCR and high throughput sequencing determination techniques.

The assay systems of the invention provide a more efficient and economical use of data, and the substantial majority of sequences analyzed following sample amplification result in affirmative information about the presence of a particular CNV in the mixed sample. Thus, unlike techniques relying on massively parallel sequencing or random digital "counting" of chromosome regions and subsequent identification of relevant data from such counts, the assay system of the invention provides a much more efficient use of data collection than the random approaches taught by others in the art.

Assay Methods

The assay systems of the invention utilize a general scheme as described above, though many different configurations and variations can be employed, a few of which are described below and more of which are exemplified in U.S. Ser. No. 61/371,605 filed Aug. 6, 2010, and U.S. Ser. No. 13/013,732, both of which are incorporated by reference herein in their entirety.

Figure 2:
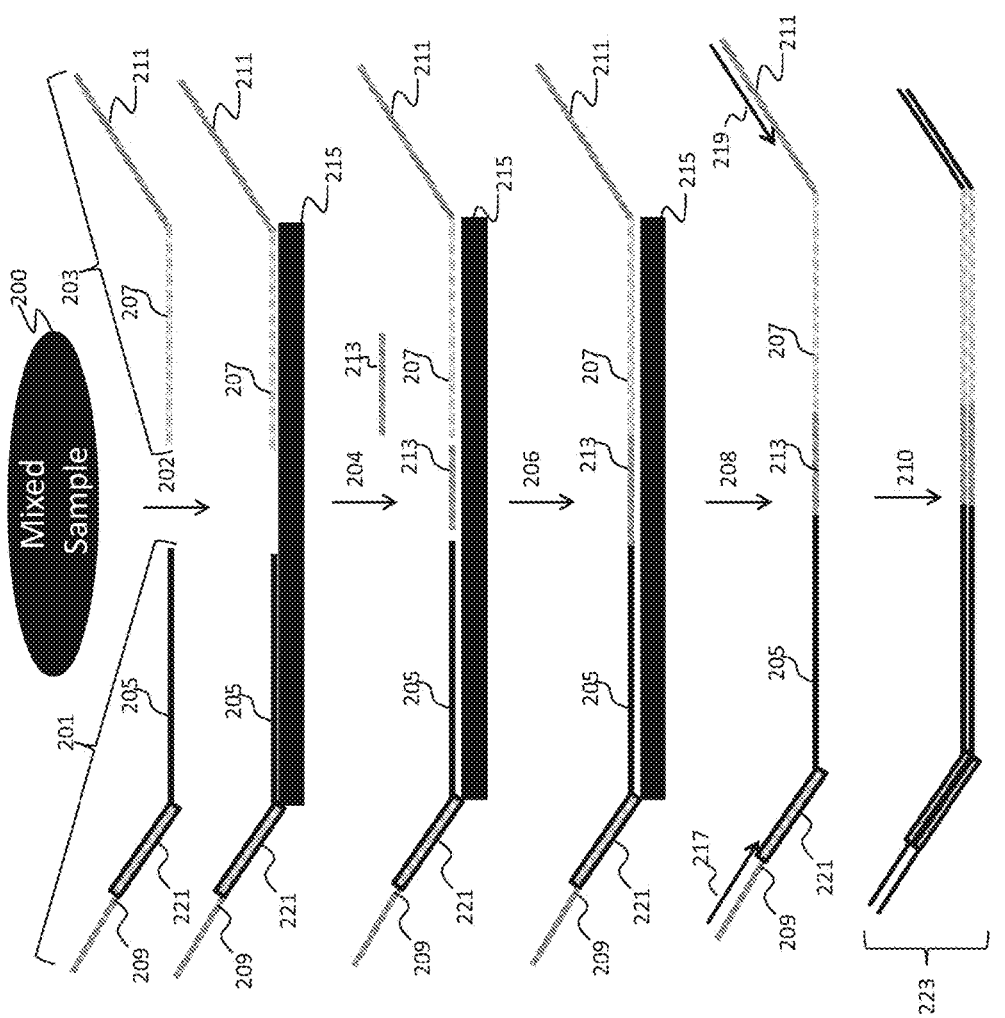
FIG. 2 illustrates a first general schematic for a ligation-based assay system of the invention.

FIG. 2 illustrates a first general schematic for a ligation-based assay system of the invention. The fixed sequence oligonucleotides 201, 203 comprise universal primer regions 209 and 211, respectively, and regions complementary to the selected locus 205 and 207, respectively. However, in addition, the assay system in FIG. 2 employs a sample index region 221 on the first fixed sequence oligonucleotide 201. In certain aspects, all or a portion of the sequences of the selected loci are directly detected using the described techniques, e.g., by sequence determination or hybridization techniques. In the example of FIG. 2, a sample index is associated with the first fixed sequence oligonucleotide 201. The detection of the indices can identify a sequence from a specific sample in a highly multiplexed assay system.

At step 202, the fixed sequence oligonucleotides 201, 203 are introduced in step 202 to the mixed sample 200 and allowed to specifically bind to the selected locus 215. Following hybridization, the unhybridized fixed sequence oligonucleotides are preferably separated from the remainder of the genetic sample (by, e.g., washing—not shown). A bridging oligo is then introduced and allowed to hybridize in step 204 to the region of the locus 215 between the first 201 and second 203 fixed sequence oligonucleotides. The bound oligonucleotides are ligated at step 206 to create a contiguous nucleic acid spanning and complementary to the locus of interest. In certain aspects of the invention, the bridging oligonucleotides of are between 2-45 nucleotides in length. In a specific aspect, the bridging oligonucleotides are between 3-9 nucleotides in length. In yet another specific aspect, the bridging oligonucleotides are between 10-30 nucleotides in length.

Following ligation, the ligation product is eluted from the gDNA template. Universal primers 217, 219 are introduced in step 208 to amplify the ligated first and second fixed sequence oligonucleotides to create 210 amplification products 223 that comprise the sequence of the locus of interest. These products 223 are isolated, detected, identified and quantified to provide information regarding the presence and amount of the selected loci in the mixed sample. Preferably, the amplification products are detected and quantified through sequence determination. In specific aspects, it is desirable to determine the sequences of both the index and the amplification products, for example, to provide identification of the sample as well as the locus. The indices envisioned in the invention may be associated with the first fixed sequence oligonucleotides, the second fixed sequence oligonucleotides or both. Alternatively or in addition, indices may be associated with primers that are used to amplify the ligated first and second fixed sequence oligonucleotides, which also serves to incorporate indices into the amplification products.

In preferred aspects, indices representative of the mixed sample from which a nucleic acid may be isolated are used to identify the source of the selected loci in a multiplexed assay system. In such aspects, the nucleic acids are uniquely identified with the sample index. Uniquely identified oligonucleotides may then be combined into a single reaction vessel with nucleic acids from other mixed samples prior to sequencing. In such a case, the sequencing data is segregated by the unique sample index to determine the frequency of each target locus for each mixed sample and to determine whether there is a chromosomal abnormality in an individual sample.

In aspects of the invention using sample indices, the fixed sequence oligonucleotides preferably are designed so that sample indices comprising identifying information are located between the universal primer regions 209 and 211 and the regions complementary to the selected loci in the sample 205 and 207. Alternatively, the indices and universal amplification sequences can be added to the ligated first and second fixed sequence oligos (and the bridging oligo, if present) by including these indices in the primers used to amplify the ligation products for separate samples. In either case, preferably the indices are encoded upstream of the locus-specific sequences but downstream of the universal primers so that they are preserved upon amplification.

Figure 3:
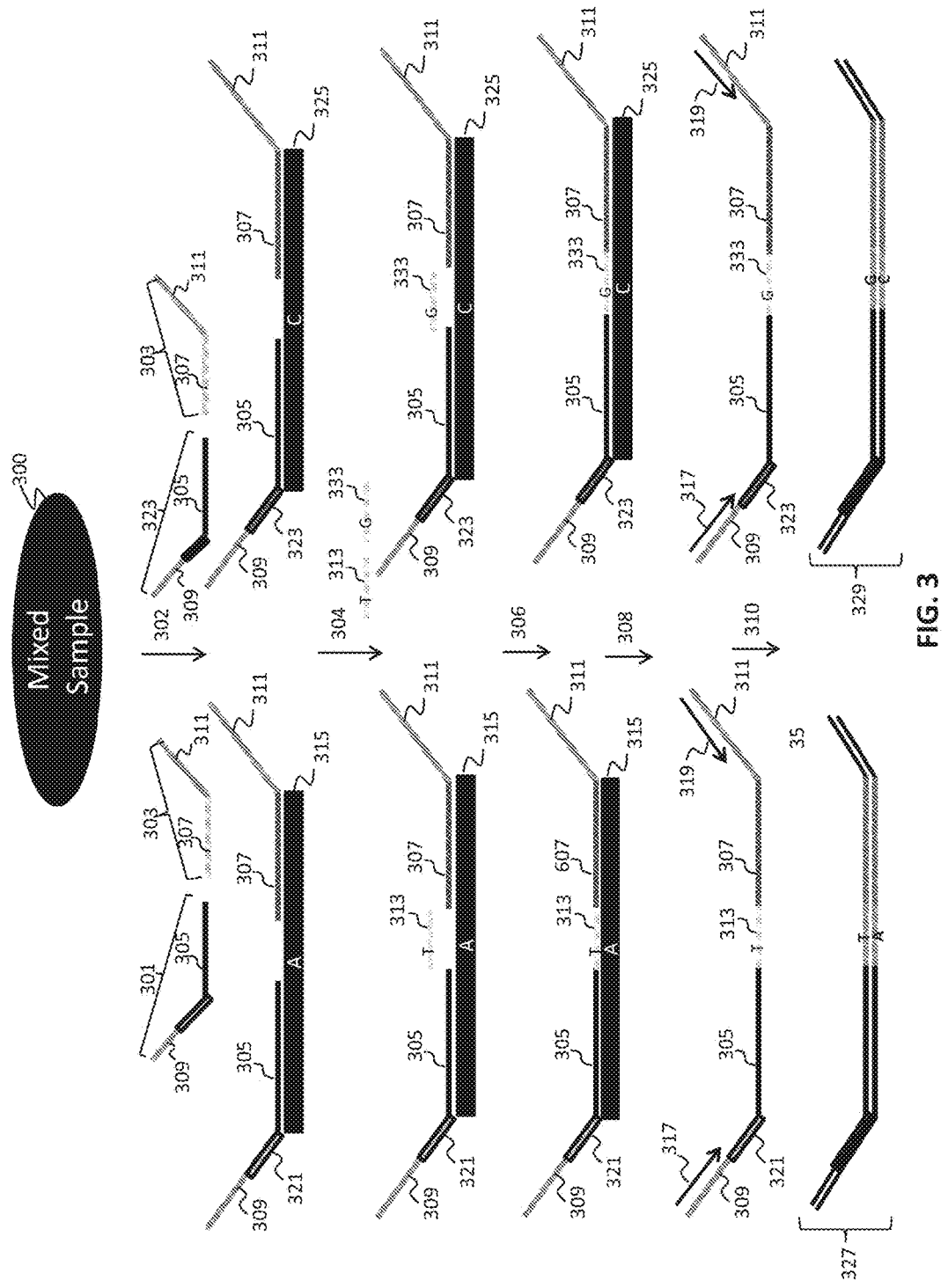
FIG. 3 illustrates a second general schematic for a ligation-based assay system of the invention.

FIG. 3 exemplifies methods of the assay system in which one or more bridging oligonucleotides are employed and exemplifies how polymorphisms may be detected and identified. In FIG. 3, two fixed sets of sequence oligonucleotides are used which comprise substantially the same universal primers 309, 311 and sequence-specific regions 305, 307, but comprise different sample indices, 321, 323 on the fixed sequence oligonucleotides of the set where the different indices correspond to different base sequences for the single nucleotide polymorphism present in a particular sample. The ligation reactions are carried out with material from the same mixed sample 300, but in separate tubes with the different allele-specific oligo sets. Bridging oligonucleotides corresponding to two possible nucleotides for this SNP in the selected loci 313, 333 are used to detect of the selected locus in each ligation reaction. Two allele indices 321, 323 that are indicative of the particular polymorphic alleles are incorporated into the amplification products so that sequence determination of the actual sequence of the ligated first, second and bridging oligonucleotides are not necessarily needed, although the sequences of the entire ligation products may still be determined to identify and/or provide confirmation.

Each of the fixed sequence oligonucleotides comprises a region complementary to the selected locus 305, 307, and universal primer regions 309, 311 used to amplify the different selected loci following initial selection and/or isolation of the selected loci from the mixed sample. The universal primer regions are located at the ends of the fixed sequence oligonucleotides 301, 303, and 323 flanking the indices and the regions complementary to the nucleic acid of interest, thus preserving the nucleic acid-specific sequences and the sample indices in the products of any universal amplification methods. The fixed sequence oligonucleotides 301, 303, 323 are introduced at step 302 to an aliquot of the genetic sample 300 and allowed to specifically bind to the selected loci 315 or 325. Following hybridization, the unhybridized fixed sequence oligonucleotides are preferably separated from the remainder of the genetic sample by, e.g., washing (not shown).

The bridging oligos corresponding to an A/T SNP 313 or a G/C SNP 333 are introduced and allowed to bind in step 304 to the region of the selected locus 315 or 325 between the first 305 and second 307 nucleic acid-complementary regions of the fixed sequence oligonucleotides. Alternatively, the bridging oligos 313, 333 can be introduced to the sample simultaneously with the fixed sequence oligonucleotides. The bound oligonucleotides are ligated in step 306 in the single reaction mixture to create a contiguous nucleic acid spanning and complementary to the selected locus.

Following ligation, the separate reactions may preferably be combined for the universal amplification and detection steps. Universal primers 317, 319 are introduced to the combined reactions at step 308 to amplify the ligated template regions and create at step 310 ligated first and second fixed sequence oligos and bridging oligo products 327, 329 that comprise the sequence of the selected locus representing both SNPs in the selected locus. These ligation products 327, 329 are detected and quantified through sequence determination of the ligation product, through the sample index and/or the region of the product containing the SNP in the selected locus.

Figure 4:
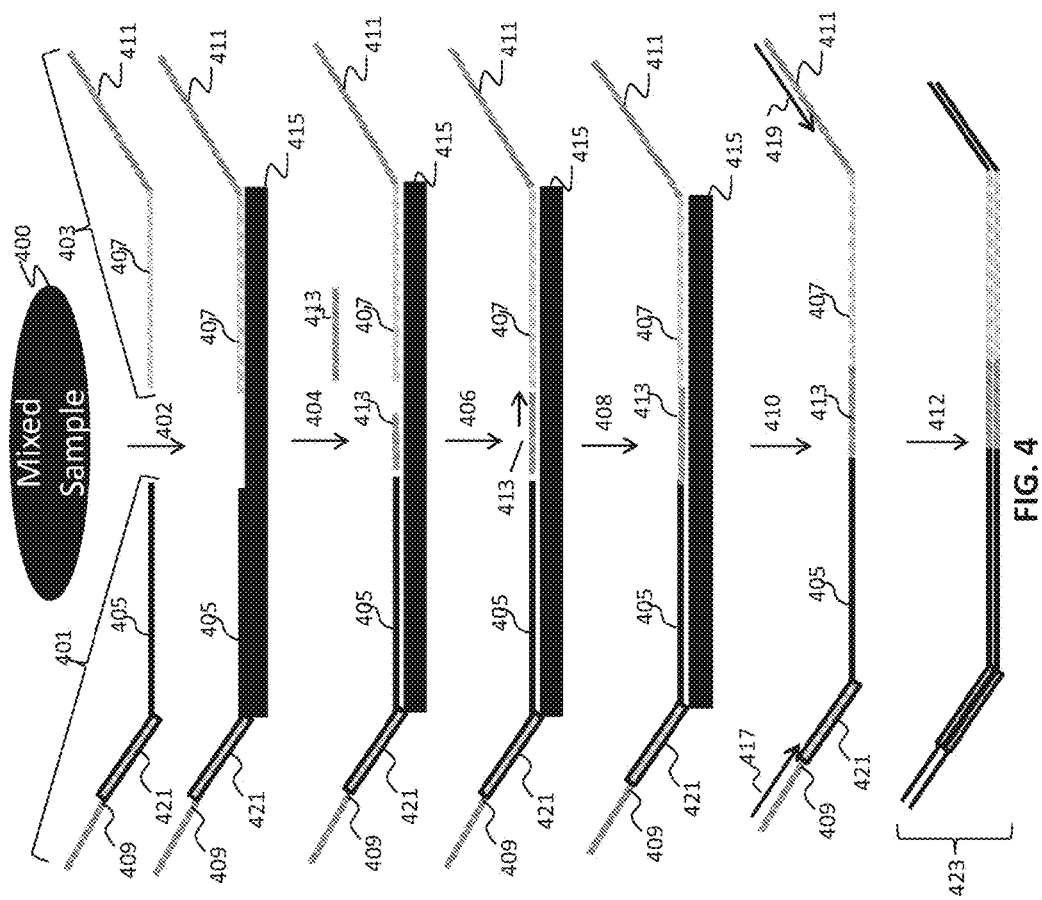
FIG. 4 is a third general schematic for a ligation-based assay system of the invention.

In an alternative configuration of the methods of the assay systems of the invention, the bridging oligo may hybridize to a region that is not directly adjacent to the region complementary to one or both of the fixed sequence oligos, and an intermediate step requiring extension of one or more of the oligos is necessary prior to ligation. For example, as illustrated in FIG. 4, each set of oligonucleotides preferably contains two oligonucleotides 401, 403 of fixed sequence and one or more bridging oligonucleotides 413. Each of the fixed sequence oligonucleotides comprises a region complementary to the selected locus 405, 407, and primer sequences, preferably universal primer sequences, 409, 411, i.e., oligo regions complementary to universal primers. The primer sequences 409, 411 are located at or near the ends of the fixed sequence oligonucleotides 401, 403, and thus preserve the nucleic acid-specific sequences in the products of any universal amplification methods. The fixed sequence oligonucleotides 401, 403 are introduced at step 402 to the mixed sample 400 and allowed to specifically bind to the complementary portions of the locus of interest 415. Following hybridization, the unhybridized fixed sequence oligonucleotides are preferably separated from the remainder of the genetic sample (not shown).

The bridging oligonucleotide is then introduced at step 404 and allowed to bind to the region of the selected locus 415 between the first 401 and second 403 fixed sequence oligonucleotides. Alternatively, the bridging oligo can be introduced simultaneously with the fixed sequence oligonucleotides. In this exemplary aspect, the bridging oligo hybridizes to a region directly adjacent to the first fixed sequence oligo region 405, but is separated by one or more nucleotides from the complementary region of the second fixed sequence oligonucleotide 407. Following hybridization of the fixed sequence and bridging oligos, the bridging oligo 413 is extended at step 406, e.g., using a polymerase and dNTPs, to fill the gap between the bridging oligo 413 and the second fixed sequence oligo 403. Following extension, the bound oligonucleotides are ligated at step 408 to create a contiguous nucleic acid spanning and complementary to the locus of interest 415. After ligation, universal primers 417, 419 are introduced at step 410 to amplify the ligated first, second and bridging oligos to create at step 412 amplification products 423 that comprise the sequence of the selected locus of interest. Amplification products 423 are optionally isolated, detected, and quantified to provide information on the presence and amount of the selected locus(s) in the mixed sample.

Detecting Copy Number Variations

The assay systems utilize nucleic acid probes designed to identify, and preferably to isolate, selected nucleic acids regions in a mixed sample. Certain of the probes identify sequences of interest in selected loci interrogated for copy number (i.e. loci frequency), and other probes identify sequences that correspond to polymorphisms of interest (i.e. loci content) in nucleic acids corresponding to a major source or minor source in a mixed sample.

In specific aspects, the assay systems of the invention employ one or more selective amplification steps (e.g., using one or more primers that specifically hybridize to a selected locus) for isolating, amplifying or analyzing substantially all of the selected loci analyzed. This is in direct contrast to the random amplification approach used by others employing, e.g., massively parallel sequencing, as such amplification techniques generally involve random amplification of all or a substantial portion of the genome. In addition, although the initial sample can be enriched using methods such as general amplification to increase the copy number of nucleic acids in the mixed sample, preferably no enrichment steps are used prior to the hybridization, ligation, and amplification steps used to identify the loci of interest.

In a general aspect, the user of the invention analyzes multiple selected loci on different chromosomes. When multiple loci are analyzed for a sample, a preferred embodiment is to amplify all of the selected loci for each sample in one reaction vessel. The frequency or amount of the multiple selected loci are analyzed to determine whether a chromosomal abnormality exists, and the presence or absence of a polymorphism is analyzed to determine the presence or absence or likelihood calculation of a chromosomal abnormality in a source in the mixed sample.

In preferred aspects, multiple selected loci from two or more samples may be amplified in a single reaction vessel, and the information simultaneously analyzed in a single data set, e.g., through sequence determination. The resulting data is then analyzed to separate the results for the different sample and used to determine the presence of absence of CNV and/or the presence of absence of polymorphisms for individual samples.

In one aspect, chromosomal abnormalities are identified in the assay system of the invention using multiple selected loci on multiple chromosomes, and the frequency of the selected loci on the multiple chromosomes compared to identify an increase likelihood of aneuploidy based on the ratios of the chromosomes. Normalization or standardization of the frequencies can be performed for one or more selected loci.

In another aspect, the assay system sums the frequencies of the selected loci on two or more chromosomes and then compares the sum of the selected loci on one chromosome against another chromosome to determine whether a chromosomal aneuploidy exists. In another aspect, the assay system analyzes subsets of selected loci on two or more chromosomes to determine whether a chromosomal aneuploidy exists for one of the two chromosomes. The comparison can be made either within the same or different chromosomes.

In certain aspects, the data used to determine the frequency of the selected loci may exclude outlier data that appear to be due to experimental error, or that have elevated or depressed levels based on an idiopathic genetic bias within a particular sample. In one example, the data used for summation may exclude DNA regions with a particularly elevated frequency in one or more samples. In another example, the data used for summation may exclude selected loci that are found in a particularly low abundance in one or more samples.

In another aspect subsets of loci can be chosen randomly but with sufficient numbers of loci to yield a statistically significant result in determining whether a chromosomal abnormality exists. Multiple analyses of different subsets of loci can be performed within a mixed sample to yield more statistical power. For example, if there are 100 selected regions for chromosome 21 and 100 selected regions for chromosome 18, a series of analyses could be performed that evaluate fewer than 100 regions for each of the chromosomes. In this example, selected loci are not being selectively excluded.

The quantity of different nucleic acids detectable on certain chromosomes may vary depending upon a number of factors, including general representation of loci in different cell sources in maternal samples, degradation rates of the different nucleic acids representing different loci in mixed samples, sample preparation methods, and the like. Thus, in another aspect, the quantity of particular loci on a chromosome is summed to determine the loci quantity for different chromosomes in the sample. The loci frequencies are summed for a particular chromosome, and the sum of the loci are used to determine aneuploidy. This aspect of the invention sums the frequencies of the individual loci on each chromosome and then compares the sum of the loci on one chromosome against another chromosome to determine whether a chromosomal abnormality exists.

The nucleic acids analyzed using the assay systems of the invention are preferably selectively amplified and optionally isolated from the mixed sample using primers specific to the locus of interest (e.g., to a locus of interest in a mixed sample). The primers for such selective amplification designed to isolate regions may be chosen for various reasons, but are preferably designed to 1) efficiently amplify a region from the chromosome of interest; 2) have a predictable range of expression from maternal and/or fetal sources in different mixed samples; 3) be distinctive to the particular chromosome, i.e., not amplify homologous regions on other chromosomes. The following are exemplary techniques that may be employed in the assay system or the invention.

The assay system of the invention detects both fetal aneuploidies and specific chromosomal abnormalities through identification and quantification of specific loci of interest. Such additional abnormalities include, but are not limited to, deletion mutations, insertion mutations, copy number polymorphisms, copy number variants, chromosome 22q11 deletion syndrome, 11q deletion syndrome on chromosome 11, 8p deletion syndrome on chromosome 8, and the like. Generally, at least two selected nucleic acid sequences present on the same or separate chromosomes are analyzed, and at least one of the selected loci is associated with the fetal allelic abnormality. The sequences of the two selected loci and number of copies of the two selected loci are then compared to determine whether the chromosomal abnormality is present, and if so, the nature of the abnormality.

While much of the description contained herein describes detecting aneuploidy by counting the abundance of loci on one or more putative aneuploid chromosomes and the abundance of loci on one or more normal chromosomes, the same techniques may be used to detect copy number variations where such copy number variation occurs on only a portion of a chromosome. In this detection of the copy number variations, multiple loci within the putative copy number variation location are compared to multiple loci outside of the putative copy number variation location. For instance, one may detect a chromosome 22q11 deletion syndrome in a fetus in a maternal sample by selecting two or more nucleic regions within the 22q11 deletion and two or more loci outside of the 22q11 deletion. The loci outside of the 22q11 deletion may be on another region of Chromosome 22 or may be on a completely different chromosome. The abundance of each loci is determined by the methods described in this application.

In some aspects a universal amplification may be used for amplifying the loci. In some aspects, the loci for each sample are assayed in a single reaction in a single vessel. In other aspects, loci from multiple samples can be assayed in a single reaction in a single vessel.

Certain aspects of the invention can detect a deletion, including the boundaries of such deletions. In some aspects, at least 24 selected loci may be used within the region of the putative deletion and at least 24 selected loci may be used outside of the region of the putative deletion. In another aspect at least 48 selected loci may be used within the region of the putative deletion and at least 48 selected loci may be used outside of the region of the putative deletion. In another aspect at least 48 selected loci may be used within the region of the putative deletion and at least 96 selected loci may be used outside of the region of the putative deletion. In another aspect at least 48 selected loci may be used within the region of the putative deletion and at least 192 selected loci may be used outside of the region of the putative deletion. In a preferred aspect at least 384 selected loci may be used within the region of the putative deletion and at least 384 selected loci may be used outside of the region of the putative deletion. The loci within the deletion are then summed as are the loci outside of the deletion. These sums are then compared to each other to determine the presence or absence of a deletion. Optionally, the sums are put into a ratio and that ratio may be compared to an average ratio created from a normal population. When the ratio for a sample falls statistically outside of an expected ratio, the deletion is detected. The threshold for the detection of a deletion may be twice or more, preferably four or more times the variation calculated in the normal population.

Polymorphisms Associated with Diseases or Predispositions

The assay systems of the invention are utilized to detect polymorphisms, such as those associated with an autosomal dominant or recessive disease or predisposition disorder. Given the multiplexed nature of the assay systems of the invention, this detection takes place in the same assay as the detection of chromosomal abnormalities. Thus a single assay system can provide diagnostic information on different classes of genetic mutations. Accordingly, as the preferred assay systems of the invention are highly multiplexed and able to interrogate hundreds or even thousands of nucleic acids within a mixed sample, in certain aspects it is desirable to interrogate the sample for nucleic acid markers within the mixed sample, e.g., nucleic acids associated with genetic risk or that identify the presence or absence of infectious organisms. Thus, the assay systems provide detection of such nucleic acids in conjunction with the detection of nucleic acids for copy number determination within a mixed sample.

Thus, the assay system of the invention can be used to detect polymorphisms in a mixed sample, where such polymorphisms are associated with genes associated with autosomal recessive disorders, mutations associated with autosomal dominant disorders; polymorphisms associated with risk of developing a disease and/or disease progression (e.g., metastasis) and prognosis indicators.

In other specific aspects, the assay system of the invention can be used to detect fetal mutations or polymorphisms in a maternal sample, where such mutations or polymorphisms are associated with polygenic disorders such as coronary heart disease, diabetes, hypertension, congenital heart defects, and epilepsy. Examples include mutations in genes associated with predispositions such as mutations in cancer susceptibility genes, (e.g. mutations in BRCAI or II or in p53); polymorphisms associated with increased risk of developing later onset diseases, such as the apoE3 gene polymorphism associated with Alzheimer's risk, In addition to detection of chromosomal abnormalities and single gene mutations or polymorphisms associated with monogenic or polygenic disease, disorders or predispositions, the assay systems of the invention may identify infectious agents in the mixed sample.

Selected Amplification

Numerous selective amplification methods can be used to provide the amplified nucleic acids that are analyzed in the assay systems of the invention, and such methods are preferably used to increase the copy numbers of a locus of interest in a mixed sample in a manner that allows preservation of information concerning the initial content of the locus in the mixed sample. Although not all combinations of amplification and analysis are described herein in detail, it is well within the skill of those in the art to utilize different amplification methods and/or analytic tools to isolate and/or analyze the nucleic acids of region consistent with this specification, and such variations will be apparent to one skilled in the art upon reading the present disclosure.

Such amplification methods include but are not limited to, polymerase chain reaction (PCR) (U.S. Pat. Nos. 4,683,195; and 4,683,202; PCR Technology: Principles and Applications for DNA Amplification, ed. H. A. Erlich, Freeman Press, NY, N.Y., 1992), ligase chain reaction (LCR) (Wu and Wallace, Genomics 4:560, 1989; Landegren et al., Science 241:1077, 1988), strand displacement amplification (SDA) (U.S. Pat. Nos. 5,270,184; and 5,422,252), transcription-mediated amplification (TMA) (U.S. Pat. No. 5,399,491), linked linear amplification (LLA) (U.S. Pat. No. 6,027,923), and the like, self-sustained sequence replication (Guatelli et al., Proc. Nat. Acad. Sci. USA, 87, 1874 (1990) and WO90/06995), selective amplification of target polynucleotide sequences (U.S. Pat. No. 6,410,276), consensus sequence primed polymerase chain reaction (CP-PCR) (U.S. Pat. No. 4,437,975), arbitrarily primed polymerase chain reaction (AP-PCR) (U.S. Pat. Nos. 5,413,909, 5,861,245) and nucleic acid based sequence amplification (NASBA). (See, U.S. Pat. Nos. 5,409,818, 5,554,517, and 6,063,603, each of which is incorporated herein by reference). Other amplification methods that may be used include: Qbeta Replicase, described in PCT Patent Application No. PCT/US87/00880, isothermal amplification methods such as SDA, described in Walker et al., Nucleic Acids Res. 20(7):1691-6 (1992), and rolling circle amplification, described in U.S. Pat. No. 5,648,245. Other amplification methods that may be used are described in, U.S. Pat. Nos. 5,242,794, 5,494,810, 4,988,617 and in U.S. Ser. No. 09/854,317 and US Pub. No. 20030143599, each of which is incorporated herein by reference. In some aspects DNA is amplified by multiplex locus-specific PCR.

In a preferred aspect the DNA is amplified using adaptor-ligation and single primer PCR. Other available methods of amplification, such as balanced PCR (Makrigiorgos, et al., Nature Biotechnol, 20:936-9 (2002)) and isothermal amplification methods such as nucleic acid sequence based amplification (NASBA) and self-sustained sequence replication (Guatelli et al., PNAS USA 87:1874 (1990)). Based on such methodologies, a person skilled in the art readily can design primers in any suitable regions 5' and 3' to a locus of interest. Such primers may be used to amplify DNA of any length so long that it contains the locus of interest in its sequence.

The length of an amplified selected locus from a genomic region of interest is long enough to provide enough sequence information to distinguish it from other nucleic acids that are amplified and/or selected. Generally, an amplified nucleic acid is at least about 16 nucleotides in length, and more typically, an amplified nucleic acid is at least about 20 nucleotides in length. In a preferred aspect of the invention, an amplified nucleic acid is at least about 30 nucleotides in length. In a more preferred aspect of the invention, an amplified nucleic acid is at least about 32, 40, 45, 50, or 60 nucleotides in length. In other aspects of the invention, an amplified nucleic acid can be about 100, 150 or up to 200 in length.

In certain aspects, the selected amplification comprises an initial linear amplification step. This can be particularly useful if the starting amount of DNA from the mixed sample is quite limited, e.g., where the cell-free DNA in a sample is available in limited quantities. This mechanism increases the amount of DNA molecules that are representative of the original DNA content, and help to reduce sampling error where accurate quantification of the DNA or a fraction of the DNA (e.g., fetal DNA contribution in a maternal sample) is needed.

Thus, in one aspect, a limited number of cycles of sequence-specific linear amplification are performed on the starting mixed sample comprising cfDNA. The number of cycles is generally less than that used for a typical PCR amplification, e.g., 5-30 cycles or fewer. Primers or probes may be designed to amplify specific genomic segments or regions. The primers or probes may be modified with an end label at the 5' end (e.g. with biotin) or elsewhere along the primer or probe such that the amplification products could be purified or attached to a solid substrate (e.g., bead or array) for further isolation or analysis. In a preferred aspect, the primers are multiplexed such that a single reaction yields multiple DNA fragments from different regions. Amplification products from the linear amplification could then be further amplified with standard PCR methods or with additional linear amplification.

For example, cfDNA can be isolated from blood, plasma, or serum from a pregnant woman, and incubated with primers against a set number of loci that correspond to chromosomes of interest. Preferably, the number of primers used for initial linear amplification will be 12 or more, more preferably 24 or more, more preferably 36 or more, even more preferably 48 or more, and even more preferably 96 or more. Each of the primers corresponds to a single locus, and is optionally tagged for identification and/or isolation. A limited number of cycles, preferably 10 or fewer, are performed with linear amplification. The amplification products are subsequently isolated, e.g., when the primers are linked to a biotin molecule the amplification products can be isolated via binding to avidin or streptavidin on a solid substrate. The products are then subjected to further biochemical processes such as further amplification with other primers and/or detection techniques such as sequence determination and hybridization.

Efficiencies of linear amplification may vary between sites and between cycles so that in certain systems normalization may be used to ensure that the products from the linear amplification are representative of the nucleic acid content starting material. One practicing the assay system of the invention can utilize information from various samples to determine variation in nucleic acid levels, including variation in different loci in individual samples and/or between the same loci in different samples following the limited initial linear amplification. Such information can be used in normalization to prevent skewing of initial levels of DNA content.

Universal Amplification

In preferred aspects of the invention, the selectively amplified loci are preferably further amplified through universal amplification of all or substantially all of the various loci to be analyzed using the assay systems of the invention. Universal primer regions are added to the fixed sequence oligonucleotides so that the selectively amplified loci may be further amplified in a single universal amplification reaction. These universal primer sequences may be added to the nucleic acids regions during the selective amplification process, i.e., the primers for selective amplification have universal primer sequences that flank a locus. Alternatively, adapters comprising universal amplification sequences can be added to the ends of the selected nucleic acids as adapters following amplification and isolation of the selected nucleic acids from the mixed sample.

In one exemplary aspect, nucleic acids are initially amplified from a mixed sample using primers complementary to selected regions of the chromosomes of interest, followed by a universal amplification step to increase the number of loci for analysis. This introduction of primer regions to the initial amplification products from a mixed sample allows a subsequent controlled universal amplification of all or a portion of selected nucleic acids prior to or during analysis, e.g. sequence determination.

Bias and variability can be introduced during DNA amplification, such as that seen during polymerase chain reaction (PCR). In cases where an amplification reaction is multiplexed, there is the potential that loci will amplify at different rates or efficiency. Part of this may be due to the variety of primers in a multiplex reaction with some having better efficiency (i.e. hybridization) than others, or some working better in specific experimental conditions due to the base composition. Each set of primers for a given locus may behave differently based on sequence context of the primer and template DNA, buffer conditions, and other conditions. A universal DNA amplification for a multiplexed assay system will generally introduce less bias and variability.

Accordingly, in a one aspect, a small number (e.g., 1-10, preferably 3-5) of cycles of selected amplification or nucleic acid enrichment of the initial sample in a multiplexed mixture reaction are performed, followed by universal amplification using introduced universal primers. The number of cycles using universal primers will vary, but will preferably be at least 10 cycles, more preferably at least 5 cycles, even more preferably 20 cycles or more. By moving to universal amplification following a lower number of amplification cycles, the bias of having certain loci amplify at greater rates than others is reduced.

Optionally, the assay system will include a step between the selected amplification and universal amplification to remove any excess nucleic acids that are not specifically amplified in the selected amplification.

The whole product or an aliquot of the product from the selected amplification may be used for the universal amplification. The same or different conditions (e.g., polymerase, buffers, and the like) may be used in the amplification steps, e.g., to ensure that bias and variability are not inadvertently introduced due to experimental conditions. In addition, variations in primer concentrations may be used to effectively limit the number of sequence specific amplification cycles.

In certain aspects, the universal primer regions of the primers or adapters used in the assay system are designed to be compatible with conventional multiplexed assay methods that utilize general priming mechanisms to analyze large numbers of nucleic acids simultaneously in one reaction in one vessel. Such "universal" priming methods allow for efficient, high volume analysis of the quantity of loci present in a mixed sample, and allow for comprehensive quantification of the presence of loci within such a mixed sample for the determination of aneuploidy.

Examples of such assay methods include, but are not limited to, multiplexing methods used to amplify and/or genotype a variety of samples simultaneously, such as those described in Oliphant et al., U.S. Pat. No. 7,582,420.

Some aspects utilize coupled reactions for multiplex detection of nucleic acid sequences where oligonucleotides from an early phase of each process contain sequences which may be used by oligonucleotides from a later phase of the process. Exemplary processes for amplifying and/or detecting nucleic acids in samples can be used, alone or in combination, including but not limited to the methods described below, each of which are incorporated by reference in their entirety.

In certain aspects, the assay system of the invention utilizes one of the following combined selective and universal amplification techniques: (1) ligase detection reaction ("LDR") coupled with polymerase chain reaction ("PCR"); (2) primary PCR coupled to secondary PCR coupled to LDR; and (3) primary PCR coupled to secondary PCR. Each of these aspects of the invention has particular applicability in detecting certain nucleic acid characteristics. However, each requires the use of coupled reactions for multiplex detection of nucleic acid sequence differences where oligonucleotides from an early phase of each process contain sequences which may be used by oligonucleotides from a later phase of the process.

Barany et al., U.S. Pat. Nos. 6,852,487, 6,797,470, 6,576, 453, 6,534,293, 6,506,594, 6,312,892, 6,268,148, 6,054,564, 6,027,889, 5,830,711, 5,494,810, describe the use of the ligase chain reaction (LCR) assay for the detection of specific sequences of nucleotides in a variety of nucleic acid samples.

Barany et al., U.S. Pat. Nos. 7,807,431, 7,455,965, 7,429, 453, 7,364,858, 7,358,048, 7,332,285, 7,320,865, 7,312,039, 7,244,831, 7,198,894, 7,166,434, 7,097,980, 7,083,917, 7,014,994, 6,949,370, 6,852,487, 6,797,470, 6,576,453, 6,534,293, 6,506,594, 6,312,892, and 6,268,148 describe LDR coupled PCR for nucleic acid detection.

Barany et al., U.S. Pat. Nos. 7,556,924 and 6,858,412, describe the use of precircle probes (also called "padlock probes" or "multi-inversion probes") with coupled LDR and polymerase chain reaction ("PCR") for nucleic acid detection.

Barany et al., U.S. Pat. Nos. 7,807,431, 7,709,201, and 7,198, 814 describe the use of combined endonuclease cleavage and ligation reactions for the detection of nucleic acid sequences.

Willis et al., U.S. Pat. Nos. 7,700,323 and 6,858,412, describe the use of precircle probes in multiplexed nucleic acid amplification, detection and genotyping.

Ronaghi et al., U.S. Pat. No. 7,622,281 describes amplification techniques for labeling and amplifying a nucleic acid using an adapter comprising a unique primer and a barcode.

In some cases, a single assay may employ a combination of the above-described methods. For example, some of the loci may be detected using fixed sequence oligonucleotides that bind to adjacent, complementary regions on a locus, while other loci may be detected using bridging loci in the same assay. In another example, some of the loci may be detected using fixed sequence oligonucleotides that bind to adjacent, complementary regions on a locus, while other loci may require a primer extension step to join the fixed sequence oligonucleotides.

In a preferred aspect, the amplification products are multiplexed, as described previously. In a preferred aspect, the multiplex amplification products are quantified by analysis of the amplification products. In a preferred aspect, a representational sample of individual molecules from the amplification processes is isolated from the other molecules for further analysis. To obtain a representational sample of individual molecules, the average number of molecules per locus must exceed the sampling noise created by the multiplexed reaction. In one aspect, the average number per locus is greater than 100. In another aspect, the average number per locus is greater than 500. In another aspect the average number per locus is greater than 1000.

Individual molecules from the amplification product are preferably isolated physically from the other molecules in a manner that allows the different amplification products to be distinguished from one another in analysis. In a preferred aspect, this isolation occurs on a solid substrate. The isolated molecule may be associated with a particular identifiable or physical address either prior to analysis, or the address may become known for the particular amplification products based on the outcome of the analysis. The substrate may be a planar surface or three-dimensional surface such as a bead.

Once isolated, the individual amplification product may be further amplified to make multiple identical copies of that molecule at the same known or identifiable location. The amplification may occur before or after that location becomes an identifiable or physical address. The amplification product and or its copies (which may be identical or complementary to the amplification product) are then analyzed based on the sequence of the amplification product or its copies to identify the particular locus and/or allele it represents.

In a preferred aspect, the entire length of the amplification product or a portion of the amplification product may be analyzed using sequence determination. The number of bases that need to be determined must be sufficient to uniquely identify the amplification product as belonging to a specific locus and/or allele. In one preferred aspect, the amplification product is analyzed through sequence determination of the selected amplification product.

Numerous methods of sequence determination are compatible with the assay systems of the inventions. Exemplary methods for sequence determination include, but are not limited to, including, but not limited to, hybridization-based methods, such as disclosed in Drmanac, U.S. Pat. Nos.

6,864,052; 6,309,824; and 6,401,267; and Drmanac et al, U.S. patent publication 2005/0191656, which are incorporated by reference, sequencing by synthesis methods, e.g., Nyren et al, U.S. Pat. Nos. 7,648,824, 7,459,311 and 6,210,891; Balasubramanian, U.S. Pat. Nos. 7,232,656 and 6,833,246; Quake, U.S. Pat. No. 6,911,345; Li et al, Proc. Natl. Acad. Sci., 100: 414-419 (2003); pyrophosphate sequencing as described in Ronaghi et al., U.S. Pat. Nos. 7,648,824, 7,459,311, 6,828,100, and 6,210,891; and ligation-based sequencing determination methods, e.g., Drmanac et al., U.S. Pat. Appln No. 20100105052, and Church et al, U.S. Pat. Appln Nos. 20070207482 and 20090018024.

Sequence information may be determined using methods that determine many (typically thousands to billions) of nucleic acid sequences in an intrinsically parallel manner, where many sequences are read out preferably in parallel using a high throughput serial process. Such methods include but are not limited to pyrosequencing (for example, as commercialized by 454 Life Sciences, Inc., Branford, Conn.); sequencing by ligation (for example, as commercialized in the SOLiD™ technology, Life Technology, Inc., Carlsbad, Calif.); sequencing by synthesis using modified nucleotides (such as commercialized in TruSeq™ and HiSeq™ technology by Illumina, Inc., San Diego, Calif., HELISCOPE' by Helicos Biosciences Corporation, Cambridge, Mass., and PacBio RS by Pacific Biosciences of California, Inc., Menlo Park, Calif.), sequencing by ion detection technologies (Ion Torrent, Inc., South San Francisco, Calif.); sequencing of DNA nanoballs (Complete Genomics, Inc., Mountain View, Calif.); nanopore-based sequencing technologies (for example, as developed by Oxford Nanopore Technologies, LTD, Oxford, UK), and like highly parallelized sequencing methods.

Alternatively, in another aspect, the entire length of the amplification product or a portion of the amplification product may be analyzed using hybridization techniques. Methods for conducting polynucleotide hybridization assays for detection of have been well developed in the art. Hybridization assay procedures and conditions will vary depending on the application and are selected in accordance with the general binding methods known including those referred to in: Maniatis et al. Molecular Cloning: A Laboratory Manual (2nd Ed. Cold Spring Harbor, N.Y., 1989); Berger and Kimmel Methods in Enzymology, Vol. 152, Guide to Molecular Cloning Techniques (Academic Press, Inc., San Diego, Calif., 1987); Young and Davis, P.N.A.S, 80: 1194 (1983). Methods and apparatus for carrying out repeated and controlled hybridization reactions have been described in U.S. Pat. Nos. 5,871,928, 5,874,219, 6,045,996 and 6,386,749, 6,391,623 each of which are incorporated herein by reference.

The present invention also contemplates signal detection of hybridization between ligands in certain preferred aspects. See U.S. Pat. Nos. 5,143,854, 5,578,832; 5,631,734; 5,834,758; 5,936,324; 5,981,956; 6,025,601; 6,141,096; 6,185,030; 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

Methods and apparatus for signal detection and processing of intensity data are disclosed in, for example, U.S. Pat. Nos. 5,143,854, 5,547,839, 5,578,832, 5,631,734, 5,800,992, 5,834,758; 5,856,092, 5,902,723, 5,936,324, 5,981,956, 6,025,601, 6,090,555, 6,141,096, 6,185,030, 6,201,639; 6,218,803; and 6,225,625, in U.S. Patent application 60/364,731 and in PCT Application PCT/US99/06097 (published as WO99/47964), each of which also is hereby incorporated by reference in its entirety for all purposes.

Variation Minimization within and Between Samples

One challenge with the detection of chromosomal abnormalities in a fetus by detection in a mixed sample is that the nucleic acids from the minor source are present in much lower abundance than the nucleic acids from normal cell type.

The variation between levels found between samples and/or for loci within a sample may be minimized in a combination of analytical methods, many of which are described in this application. For instance, variation is lessened by using an internal reference in the assay. An example of an internal reference is the use of a chromosome present in a "normal" abundance (e.g., disomy for an autosome) to compare against a chromosome present in putatively abnormal abundance, such as aneuploidy, in the same sample. While the use of one such "normal" chromosome as a reference chromosome may be sufficient, it is also possible to use two or more normal chromosomes as the internal reference chromosomes to increase the statistical power of the quantification.

One method of using an internal reference is to calculate a ratio of abundance of the putatively abnormal chromosomes to the abundance of the normal chromosomes in a sample, called a chromosomal ratio. In calculating the chromosomal ratio, the abundance or counts of each of the loci for each chromosome are summed together to calculate the total counts for each chromosome. The total counts for one chromosome are then divided by the total counts for a different chromosome to create a chromosomal ratio for those two chromosomes.

Alternatively, a chromosomal ratio for each chromosome may be calculated by first summing the counts of each of the loci for each chromosome, and then dividing the sum for one chromosome by the total sum for two or more chromosomes. Once calculated, the chromosomal ratio is then compared to the average chromosomal ratio from a normal population.

The average may be the mean, median, mode or other average, with or without normalization and exclusion of outlier data. In a preferred aspect, the mean is used. In developing the data set for the chromosomal ratio from the normal population, the normal variation of the measured chromosomes is calculated. This variation may be expressed a number of ways, most typically as the coefficient of variation, or CV. When the chromosomal ratio from the sample is compared to the average chromosomal ratio from a normal population, if the chromosomal ratio for the sample falls statistically outside of the average chromosomal ratio for the normal population, the sample contains an aneuploidy. The criteria for setting the statistical threshold to declare an aneuploidy depend upon the variation in the measurement of the chromosomal ratio and the acceptable false positive and false negative rates for the desired assay. In general, this threshold may be a multiple of the variation observed in the chromosomal ratio. In one example, this threshold is three or more times the variation of the chromosomal ratio. In another example, it is four or more times the variation of the chromosomal ratio. In another example it is five or more times the variation of the chromosomal ratio. In another example it is six or more times the variation of the chromosomal ratio. In the example above, the chromosomal ratio is determined by summing the counts of loci by chromosome. Typically, the same number of selected loci for each chromosome is used. An alternative method for generating the chromosomal ratio would be to calculate the average counts for the loci for each chromosome. The average may be any estimate of the mean, median or mode, although typically an average is used. The average may be the mean of all counts or some variation such as a trimmed or weighted average. Once the average counts for each chromosome have been calculated, the average counts for each chromosome may be divided by the other to obtain a chromosomal ratio between two chromosomes, the average counts for each chromosome may be divided by the sum of the averages for all measured chromosomes to obtain a chromosomal ratio for each chromosome as described above. As highlighted above, the ability to detect an aneuploidy in a maternal sample where the putative DNA is in low relative abundance depends greatly on the variation in the measurements of different selected loci in the assay. Numerous analytical methods can be used which reduce this variation and thus improve the sensitivity of this method to detect aneuploidy. One method for reducing variability of the assay is to increase the number of selected loci used to calculate the abundance of the chromosomes. In general, if the measured variation of a single selected locus of a chromosome is X % and Y different selected loci are measured on the same chromosome, the variation of the measurement of the chromosomal abundance calculated by summing or averaging the abundance of each selected locus on that chromosome will be approximately X % divided by $Y^{1/2}$. Stated differently, the variation of the measurement of the chromosome abundance would be approximately the average variation of the measurement of each selected locus' abundance divided by the square root of the number of loci.

In a preferred aspect of this invention, the number of loci measured for each chromosome is at least 24. In another preferred aspect of this invention, the number of selected loci measured for each chromosome is at least 48. In another preferred aspect of this invention, the number of selected loci measured for each chromosome is at least 100. In another preferred aspect of this invention the number of selected loci measured for each chromosome is at least 200. There is incremental cost to measuring each locus and thus it is important to minimize the number of each selected locus. In a preferred aspect of this invention, the number of selected loci measured for each chromosome is less than 2000. In a preferred aspect of this invention, the number of selected loci measured for each chromosome is less than 1000. In a most preferred aspect of this invention, the number of selected loci measured for each chromosome is at least 48 and less than 1000. In one aspect, following the measurement of abundance for each selected locus, a subset of the selected loci may be used to determine the presence or absence of aneuploidy. There are many standard methods for choosing the subset of selected loci. These methods include outlier exclusion, where the selected loci with detected levels below and/or above a certain percentile are discarded from the analysis. In one aspect, the percentile may be the lowest and highest 5% as measured by abundance. In another aspect, the percentile may be the lowest and highest 10% as measured by abundance. In another aspect, the percentile may be the lowest and highest 25% as measured by abundance.

Another method for choosing the subset of selected loci includes the elimination of regions that fall outside of some statistical limit. For instance, selected loci that fall outside of one or more standard deviations of the mean abundance may be removed from the analysis. Another method for choosing the subset of selected loci may be to compare the relative abundance of a selected locus to the expected abundance of the same selected locus in a healthy population and discard any selected loci that fail the expectation test. To further minimize the variation in the assay, the number of times each selected locus is measured may be increased. As discussed, in contrast to the random methods of detecting aneuploidy where the genome is measured on average less than once, the assay systems of the present invention intentionally measures each selected locus multiple times. In general, when counting events, the variation in the counting is determined by Poisson statistics, and the counting variation is typically equal to one divided by the square root of the number of counts. In a preferred aspect of the invention, the selected loci are each measured on average at least 100 times. In a preferred aspect to the invention, the selected loci are each measured on average at least 500 times. In a preferred aspect to the invention, the selected loci are each measured on average at least 1000 times. In a preferred aspect to the invention, the selected loci are each measured on average at least 2000 times. In a preferred aspect to the invention, the selected loci are each measured on average at least 5000 times.

In another aspect, subsets of loci can be chosen randomly but with sufficient numbers of loci to yield a statistically significant result in determining whether a chromosomal abnormality exists. Multiple analyses of different subsets of loci can be performed within a mixed sample to yield more statistical power. In this example, it may or may not be necessary to remove or eliminate any loci prior to the random analysis. For example, if there are 100 selected loci for chromosome 21 and 100 selected loci for chromosome 18, a series of analyses could be performed that evaluate fewer than 100 loci for each of the chromosomes.

In addition to the methods above for reducing variation in the assay, other analytical techniques, many of which are described earlier in this application, may be used in combination. In general, the variation in the assay may be reduced when all of the loci for each sample are interrogated in a single reaction in a single vessel. Similarly, the variation in the assay may be reduced when a universal amplification system is used. Furthermore, the variation of the assay may be reduced when the number of cycles of amplification is limited.

Use of Assay Systems for Detection in Mixed Samples from Cancer Patients

The assay system allow the detection of quantitative and qualitative tumor-specific alterations of cfDNA, such as DNA strand integrity, frequency of mutations, abnormalities of microsatellites, and methylation of genes, as diagnostic, prognostic, and monitoring markers in cancer patients. The ability to combine such detection of single gene alterations (including point mutations, indels and copy number variation) with CNV detection provides a powerful methods for assisting with clinical diagnosis, treatments, outcome prediction and progression monitoring in patients with or suspected of having a malignancy.

In some aspects, the assay system of the invention is used for diagnostic purposes e.g., to detect the presence and/or nature of a malignancy in a patient or to provide a quantitative estimate of tumor load in a patient. Circulating tumor DNA and microRNAs have been associated with certain cancers, such as lung cancer (Roth C et al., Mol Oncol. 2011 June; 5(3):281-91. Epub 2011 Feb. 24). Copy number variations have also been detected in certain cancers, such as amplified HER2 and estrogen receptor in the cfDNA in breast cancer patients. (Page K., Br J Cancer. 2011 Apr. 12; 104(8):1342-8. Epub 2011 Mar. 22).

In other aspects of the invention, the assay system is used in cancer patients to monitor a response to treatment and/or to follow progress of the disease, e.g., to measure single gene alterations and cfDNA in patients receiving chemoradiotherapy (CRT). For certain cancers, it has been shown that cfDNA integrity index can be significantly and independently associated with tumor response to treatment. Agostini M et al., Ann Surg Oncol. 2011 Mar. 17. Also, the presence or absence of certain genetic alterations and/or differences in copy number variation has been associated with response to chemotherapy and/or prognosis of a disease. See, e.g., Savas S., Acta Oncol. 2010 November; 49(8):1217-26. Epub 2010 Jul. 29, which describes useful genetic variations for determination of treatment response and survival in cancer. For example, the detection of cfDNA levels combined with detection of mutations in the K-RAS gene and/or the p53 gene provide a powerful, relatively non-invasive tool in measuring the prognosis of various cancers, including ovarian cancer, endometrial cancer and lymphomas. Dobrzycka B et al., Ann Oncol. 2011 May; 22(5):1133-40. Epub 2010 Nov. 23; Dobrzycka B et al., Int J Cancer. 2010 Aug. 1; 127(3):612-21; Hosny G et al., Cancer Lett. 2009 Mar. 18; 275(2):234-9. Epub 2008 Nov. 28. Such analysis can be further assisted using tools such as Varietas, a functional database portal for identification of genetic variation and association with treatment outcomes and prognosis. Paananen J et al., Database (Oxford). 2010 Jul. 29; 2010:baq016.

Use of Assay Systems for Detection of Mixed Samples from Transplant Patients

The assay systems of the invention can be used to monitor organ health in a transplant patient using a combination of detection of cfDNA and detection of SNPs or mutations in one or more single genes. Transplanted organs have genomes that are distinct from the genome of a recipient patient, and organ health can be detected using assay system. For example, acute cellular rejection has been shown to be associated with significantly increased levels of cell-free DNA from the donor genome in heart transplant recipients. Snyder T M et al., Proc Natl Acad Sci USA. 2011 Apr. 12; 108(15):6229-34. Epub 2011 Mar. 28. In addition, chemokines and adhesion molecules mediate allograft rejection by recruiting leukocytes into the allograft, and SNPs located in interleukin (IL)-8, CXCR1, CXCR2, have been shown to correlate with allograft outcomes. Ro H. et al., Transplantation. 2011 Jan. 15; 91(1):57-64. Thus, the assay systems of the invention can provide noninvasive tests for monitoring solid organ transplant recipients, and can aid in identification of early signs of rejection without the necessity of organ biopsies or other more onerous diagnostic or prognostic techniques.

Use of Assay Systems for Detection in Maternal Samples

In certain specific aspects, determining the relative percentage of fetal DNA in a maternal sample may be beneficial in analyzing the amplification products, as percentage fetal DNA in the sample provides important information on the expected statistical presence of chromosomes, and variation from that expectation may be indicative of fetal aneuploidy. This may be especially helpful in circumstances where the level of fetal DNA in a maternal sample is low, as the percent fetal contribution can be used in determining the quantitative statistical significance in the variations of levels of identified selected loci in a maternal sample. In other aspects, the determining of the relative percent fetal cfDNA in a maternal sample may be beneficial in estimating the level of certainty or power in detecting a fetal aneuploidy.

In some specific aspects, the relative fetal contribution of maternal DNA at the allele of interest can be compared to the paternal contribution at that allele to determine approximate fetal DNA concentration in the sample. In other specific aspects, the relative quantity of solely paternally-derived sequences (e.g., Y-chromosome sequences or paternally-specific polymorphisms) can be used to determine the relative concentration of fetal DNA in a maternal sample.

Another exemplary approach to determining the percent fetal contribution in a maternal sample through the analysis of DNA fragments with different patterns of DNA methylation between fetal and maternal DNA. In a preferred aspect, the amplified DNA from plasma free DNA is by polymerase chain reaction (PCR). Other mechanisms for amplification can be used as well, including those described in more detail herein, as will be apparent to one skilled in the art upon reading the present disclosure.

In particular aspects, the percentage of free fetal DNA in the maternal sample can determined by PCR using serially diluted DNA isolated from the maternal sample, which can accurately quantify the number of genomes comprising the amplified genes.

In circumstances where the fetus is male, percent fetal DNA in a sample can be determined through detection of Y-specific loci and comparison to calculated maternal DNA content. Quantities of an amplified Y-specific locus, such as a region from the sex-determining region Y gene (SRY), which is located on the Y chromosome and is thus representative of fetal DNA, can be determined from the sample and compared to one or more amplified selected loci which are present in both maternal DNA and fetal DNA and which are preferably not from a chromosome believed to potentially be aneuploid in the fetus, e.g., an autosomal region that is not on chromosome 21 or 18. Preferably, this amplification step is performed in parallel with the selective amplification step, although it may be performed either before or after the selective amplification depending on the nature of the multiplexed assay.

In particular aspects, the percentage of cell-free fetal DNA in a maternal sample can determined by PCR using serially diluted DNA isolated from the maternal sample, which can accurately quantify the number of genomes comprising the amplified genes. PCR using serially diluted DNA isolated from the maternal sample may be preferred when determining percent fetal DNA with a male fetus. For example, if the blood sample contains 100% male fetal DNA, and 1:2 serial dilutions are performed, then on average the Y-linked signal will disappear 1 dilution before the autosomal signal, since there is 1 copy of the Y-linked gene and 2 copies of the autosomal gene.

In a specific aspect, the percentage of free fetal DNA in maternal plasma is calculated for a male fetus using the following formula: percentage of free fetal DNA=(No. of copies of Y-linked gene×2×100)/(No. of copies of autosomal gene), where the number of copies of each gene is determined by observing the highest serial dilution in which the gene was detected. The formula contains a multiplication factor of 2, which is used to normalize for the fact that there is only 1 copy of the Y-linked gene compared to two copies of the autosomal gene in each genome, fetal or maternal.

Determination of Minor Source DNA Content in a Mixed Sample

In certain aspects of the invention, determination of the contribution of DNA form a minor source may be useful in determining copy number variation of loci in those samples. For example, in each maternally-derived sample, the DNA from a fetus will have approximately 50% of its loci inherited from the mother and 50% of the loci inherited from the father. Determining the loci contributed to the fetus from paternal sources can allow the estimation of fetal DNA in a maternal sample, and thus provide information used to calculate the statistically significant differences in chromosomal frequencies for chromosomes of interest.

In certain aspects, the determination of minor source polymorphisms requires targeted SNP and/or mutation analysis to identify the presence of the minor source DNA in a mixed sample. In some aspects, the use of prior genotyping is helpful, e.g., genotyping of the donor of a transplant, genotyping of the father and mother in a maternal sample. But generally this information pertaining to the prior genotyping is not necessary prior to performing the assay, and preferably the genotyping is performed simultaneously with the determination of copy number of selected loci within a mixed sample.

In one preferred aspect, the percent minor source nucleic acids in a mixed sample can be quantified using multiplexed SNP detection without using prior genotypic knowledge. In this aspect, two or more selected polymorphic loci with a known SNP in each region are used. In a preferred aspect, the selected polymorphic loci are lociamplified. In a preferred aspect, the amplification is universal. In a preferred embodiment, the selected polymorphic loci are amplified in one reaction in one vessel. Each allele of the selected polymorphic loci in the maternal sample is determined and quantified. In a preferred aspect, high throughput sequencing is used for such determination and quantification. Loci are identified where the major and minor source genotypes are different, e.g., the donor genotype is homozygous and the recipient genotype is heterozygous. This identification is done by observing a high relative frequency of one allele (>80%) and a low relative frequency (<20% and >0.15%) of the other allele for a particular selected locus. The use of multiple loci is particularly advantageous as it reduces the amount of variation in the measurement of the abundance of the alleles. All or a subset of the loci that meet this requirement are used to determine minor source nucleic acid concentration through statistical analysis. In one aspect, concentration is determined by summing the low frequency alleles from two or more loci together, dividing by the sum of the high frequency alleles and multiplying by two. In another aspect, the percent minor source nucleic acid is determined by averaging the low frequency alleles from two or more loci, dividing by the average of the high frequency alleles and multiplying by two.

For many alleles, major and minor source nucleic acid sequences may be homozygous and identical, and as this information is not distinguishing it is not useful in the determination of minor source nucleic acid in a mixed sample. The present invention utilizes allelic information where there is a distinguishable difference between the cell sources (e.g., a fetal allele containing at least one allele that differs from the maternal allele) in calculations of minor source nucleic acid percentages. Data pertaining to allelic regions that are the same for the major and minor source are thus not selected for analysis, or are removed from the pertinent data prior to determination of percentage so as not to swamp out the useful data.

Exemplary methods for quantifying fetal DNA in maternal plasma can be found, e.g., in Chu et al., *Prenat Diagn* 2010; 30:1226-1229, which is incorporated herein by reference.

In one aspect, selected loci may be excluded if the amount or frequency of the region appears to be an outlier due to experimental error, or from idiopathic genetic bias within a particular sample. In another aspect, selected nucleic acids may undergo statistical or mathematical adjustment such as normalization, standardization, clustering, or transformation prior to summation or averaging. In another aspect, selected nucleic acids may undergo both normalization and data experimental error exclusion prior to summation or averaging.

In a preferred aspect, 12 or more loci are used for the analysis. In another preferred aspect, 24 or more loci are used for the analysis. In another preferred aspect, 48 or more loci are used for the analysis. In another aspect, one or more indices are used to identify the sample In a specific aspect, minor source contribution can be quantified using tandem SNP detection. Techniques for identifying tandem SNPs in DNA extracted from, e.g., a maternal sample are disclosed in Mitchell et al, U.S. Pat. No. 7,799,531 and U.S. patent application Ser. Nos. 12/581,070, 12/581,083, 12/689,924, and 12/850,588. These describe the differentiation of fetal and maternal loci through detection of at least one tandem single nucleotide polymorphism (SNP) in a maternal sample that has a different haplotype between the fetal and maternal genome. Identification and quantification of these haplotypes can be performed directly on the maternal sample, as described in the Mitchell et al. disclosures, and used to determine the percent fetal contribution in the maternal sample.

Once the percent cfDNA has been calculated for the minor source, this data may be combined with methods for aneuploidy detection to determine the likelihood that a mixed sample may contain an aneuploidy. In one aspect, an aneuploidy detection methods that utilizes analysis of random DNA segments is used, such as that described in, e.g., Quake, U.S. patent application Ser. No. 11/701,686; Shoemaker et al., U.S. patent application Ser. No. 12/230,628. In a preferred aspect, aneuploidy detection methods that utilize analysis of selected loci in a mixed sample include both regions for determination of minor source DNA content as well as non-polymorphic regions from two or more chromosomes to detect a chromosomal abnormality in a single reaction. The single reaction helps to minimize the risk of contamination or bias that may be introduced during various steps in the assay system which may otherwise skew results when utilizing minor source DNA content to help determine the presence or absence of a chromosomal abnormality. In other aspects, a selected locus or regions may be utilized both for determination of minor source DNA content as well as detection of minor source chromosomal abnormalities. Utilizing the same regions for both DNA content and detection of chromosomal abnormalities may further help minimize any bias due to experimental error or contamination.

EXAMPLES

The following examples are put forth so as to provide those of ordinary skill in the art with a complete disclosure and description of how to make and use the present invention, and are not intended to limit the scope of what the inventors regard as their invention, nor are they intended to represent or imply that the experiments below are all of or the only experiments performed. It will be appreciated by persons skilled in the art that numerous variations and/or modifications may be made to the invention as shown in the specific aspects without departing from the spirit or scope of the invention as broadly described. The present aspects are, therefore, to be considered in all respects as illustrative and not restrictive.

Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees centigrade, and pressure is at or near atmospheric.

Example 1: General Aspects of the Assay Systems of the Invention

A number of assay formats were tested to demonstrate the ability to perform selective amplification and detection of independent loci to demonstrate multiplexed, ligation-based detection of a large number (e.g., 96 or more) of loci of interest. These loci included loci that were indicative of the presence of a particular chromosome or the presence or absence of a mutation or polymorphism in a particular allele.

These assays were designed based on human genomic sequences, and each interrogation consisted of two fixed sequence oligos per selected locus interrogated in the assay. The first oligo, complementary to the 3' region of a genomic region, comprised the following sequential (5' to 3') oligo elements: a universal PCR priming sequence common to all assays: TACACCGGCGTTATGCGTCGAGAC (SEQ ID NO:1); a nine nucleotide identification index specific to the selected locus; a 9 base locus- or locus/allele-specific sequence that acts as a locus index in the first SNP-independent set and a locus/allele index in the polymorphism-specific second set; a hybridization breaking nucleotide which is different from the corresponding base in the genomic locus; and a 20-24 bp sequence complementary to the selected genomic locus. In cases where a SNP or mutation was detected in this portion of the selected genomic locus, the allele-specific interrogation set consisted of two first fixed sequence tandem ligation primers, each with a different locus/allele index and a different allele-specific base at the SNP position. These first oligos were designed for each selected nucleic acid to provide a predicted uniform $T_m$ with a two degree variation across all interrogations in the assay set.

The second fixed sequence oligo, complementary to the 5' region of the genomic loci, comprised the following sequential (5' to 3') elements: a 20-24b sequence complimentary to the 5' region in the genomic locus; a hybridization breaking nucleotide different from the corresponding base in the genomic locus; and a universal PCR priming sequence which was common to all third oligos in the assay set: ATTGCGGGGACCGATGATCGCGTC (SEQ ID NO:2).

In cases where a SNP or mutation was detected in the selected genomic locus, the allele-specific interrogation set consisted of two tandem ligation primers, each with a different locus/allele index and a different allele-specific base at the mutation/SNP position. This second fixed sequence oligo was designed for each selected nucleic acid to provide a predicted uniform $T_m$ with a two degree variation across all interrogations in the assay set that was substantially the same $T_m$ range as the first oligo set.

In certain tested aspects, one or more bridging oligos were used that were complementary to the genomic locus sequence between the region complementary to the first and second fixed sequence oligos used for each selected locus. In specific aspects tested, more than one bridging oligo was used to span the gap between the fixed sequence oligonucleotides, and the one or more bridging oligo may optionally be designed to identify one or more mutations or SNPs in the sequence. The length of the bridging oligonucleotides used in the assay systems varied from 5 to 36 base pairs.

All oligonucleotides used in the tandem ligation formats were synthesized using conventional solid-phase chemistry. The second fixed sequence oligos and the bridging oligonucleotides were synthesized with 5' phosphate moieties to enable ligation to 3' hydroxyl termini of adjacent oligonucleotides.

Example 2: Preparation of DNA for Use in Tandem Ligation Procedures

Genomic DNA from a Caucasian male (NA12801) or a Caucasian female (NA11995) was obtained from Coriell Cell Repositories (Camden, N.J.) and fragmented by acoustic shearing (Covaris, Woburn, Mass.) to a mean fragment size of approximately 200 bp.

The Coriell DNA was biotinylated using standard procedures. Briefly, the Covaris fragmented DNA was end-repaired by generating the following reaction in a 1.5 ml microtube: 5 µg DNA, 12 µl 10× T4 ligase buffer (Enzymatics, Beverly Mass.), 50 U T4 polynucleotide kinase (Enzymatics, Beverly Mass.), and $H_2O$ to 120 µl. This was incubated at 37° C. for 30 minutes. The DNA was diluted using 10 mM Tris 1 mM EDTA pH 8.5 to desired final concentration of ~2 ng/µl.

5 µl DNA was placed in each well of a 96-well plate, and the plate sealed with an adhesive plate sealer and spun for 10 seconds at 250×g. The plate was then incubated at 95° C. for 3 minutes, cooled to 25° C., and spun again for 10 seconds at 250×g. A biotinylation master mix was prepared in a 1.5 ml microtube to final concentration of: 1× TdT buffer (Enzymatics, Beverly, Mass.), 8U TdT (Enzymatics, Beverly, Mass.), 250 µM $CoCl_2$, 0.01 nmol/µl biotin-16-dUTP (Roche, Nutley N.J.), and $H_2O$ to 1.5 ml. 15 µl of the master mix was aliquoted into each well of a 96 well plate, and the plate sealed with adhesive plate sealer. The plate was spun for 10 seconds at 250×g and incubated for 37° C. for 60 minutes. Following incubation, the plate was spun again for 10 seconds at 250×g, and 7.5 µl precipitation mix (1 µg/µl Dextran Blue, 3 mM NaOAC) was added to each well.

The plate was sealed with an adhesive plate sealer and mixed using an IKA plate vortexer for 2 minutes at 3000 rpm. 27.5 µl of isopropanol was added into each well, the plate sealed with adhesive plate sealer, and vortexed for 5 minutes at 3000 rpm. The plate was spun for 20 minutes at 3000×g, the supernatant was decanted, and the plate inverted and centrifuged at 10×g for 1 minute onto an absorbent wipe. The plate was air-dried for 5 minutes, and the pellet resuspended in 30 µl 10 mM Tris pH8.0, 1 mM EDTA.

Example 3: Exemplary Assay Formats Using Tandem Ligation

Numerous tandem ligation assay formats using the biotinylated DNA were tested to illustrate proof of concept for the assay systems of the invention, and demonstrated the ability to perform highly multiplexed, targeted detection of a large number of independent loci using the series of different assay formats. The exemplary assay systems of the invention were designed to comprise 96 or more interrogations per loci in a genetic sample, and in cases where SNPs were detected the assay formats utilized 192 or more separate interrogations, each utilizing the detection of different alleles per 96 loci in genetic samples. The examples described for each assay format utilized two different sets of fixed sequence oligonucleotides and/or bridging oligos (as described in Example 1), comprising a total 96 or 192 interrogation reactions for the selected loci depending upon whether or not SNPs were identified.

A first exemplary assay format used locus-specific fixed sequence oligos and bridging oligos, where there was a one base gap between the first fixed sequence oligo and the bridging oligos, and a second one base gap between the bridging oligos and the second fixed sequence oligo. Each of the two gaps encompassed two different SNPs. In this format, a DNA polymerase was used to incorporate each of the SNP bases, and ligase was used to seal the nicks formed thereby. SNP base discrimination derived from the fidelity of base incorporation by the polymerase, and in the event of mis-incorporation, the tendency of ligase to not seal nicks adjacent to mismatched bases.

The second exemplary assay format used two locus-specific fixed sequence oligonucleotides without a bridging oligo, where there was a ~15-35 base gap between the fixed sequence oligos, and where the gap spanned one or more SNPs. In this format, a polymerase was used to incorporate the missing bases of the gap, and a ligase was used to seal the nick formed thereby. SNP base discrimination derived from the fidelity of base incorporation by the polymerase, and in the event of misincorporation, the tendency of ligase to not seal nicks adjacent to mismatched bases.

A third exemplary assay format used allele-specific first and second fixed sequence oligos without a bridging oligo, where there was a ~15-35 base gap between the first and second fixed sequence oligos, and where the gap spanned one or more SNPs. Two separate allele-specific first fixed sequence oligos and two separate allele-specific second fixed sequence oligos were used. A polymerase was used to incorporate the missing bases, and a ligase was used to seal the nick formed thereby. SNP base discrimination derived from hybridization specificity, the tendency of non-proofreading polymerase to not extend annealed primers with mismatches near the 3' end, and the tendency of the ligase to not seal nicks adjacent to mismatched bases.

A fourth exemplary format used allele-specific fixed sequence oligos and a locus-specific bridging oligo. In this format, two separate fixed sequence oligos complementary to the 3' end of the loci of interest, the first with a 3' base specific for one allele of the targeted SNP, and the second with a 3' base specific for the other allele of the targeted SNP. Similarly, two separate second fixed sequence oligos were used, the first with a 5' base specific for one allele of a second targeted SNP, and the second with a 5' base specific for the other allele of the second targeted SNP. The bridging oligos were complementary to the region directly adjacent to the locus regions complementary to the first and second fixed sequence oligos, and thus no polymerase was needed prior to ligation. Ligase was used to seal the nicks between the fixed sequence oligos and the bridging oligo. SNP base discrimination in this assay format derived from hybridization specificity and the tendency of the ligase to not seal nicks adjacent to mismatched bases. This exemplary format was tested using either T4 ligase or Taq ligase for creation of the contiguous template, and both were proved effective in the reaction as described below.

A fifth exemplary format used locus-specific fixed sequence oligos that were complementary to adjacent regions on the nucleic acid of interest, and thus no gap was created by hybridization of these oligos. In this format, no polymerase was required, and a ligase was used to seal the single nick between the oligos.

A sixth exemplary format used allele-specific fixed sequence oligos and locus-specific bridging oligos, where there was a short base gap of five bases between the loci region complementary to the fixed sequence oligos. The locus-specific bridging oligo in this example was a 5mer complementary to the regions directly adjacent to the regions complementary to the first and second fixed sequence oligos. In this format, no polymerase was required, and a ligase was used to seal the two nicks between the oligos.

A seventh exemplary format used locus-specific fixed sequence oligos and a locus-specific bridging oligo, where there was a shorter base gap of five bases containing a SNP in the region complementary to the bridging oligo. Allele-specific bridging oligos corresponding to the possible SNPs were included in the hybridization and ligation reaction. In this format, no polymerase was required, and a ligase was used to seal the two nicks between the oligos. SNP base discrimination in this assay format derived from hybridization specificity and the tendency of the ligase to not seal nicks adjacent to mismatched bases.

An eighth exemplary format used locus-specific fixed sequence oligos and two adjacent locus-specific bridging oligos, where there was a 10 base gap between the regions complementary to the first and second fixed sequence oligos. Locus-specific bridging oligos were included in the ligation reaction, with the gap requiring two contiguous 5mers to bridge the gap. In this format, no polymerase was required, and a ligase was used to seal the three nicks between the oligos.

For each of the above-described assay formats, an equimolar pool (40 nM each) of sets of first and second loci- or allele-specific fixed sequence oligonucleotides was created from the oligos prepared as set forth in Example 2. A separate equimolar pool (20 μM each) of bridging oligonucleotides was likewise created for the assay processes based on the sequences of the selected genomic loci.

100 μg of strepavidin beads were transferred into the wells of a 96 well plate, and the supernatant was removed. 60 μl BB2 buffer (100 mM Tris pH 8.0, 10 mM EDTA, 500 mM $NaCl_2$, 58% formamide, 0.17% Tween-80), 10 μL 40 nM fixed sequence oligo pool and 30 μL of the biotinylated template DNA prepared in Example 2 were added to the beads. The plate was sealed with an adhesive plate sealer and vortexed at 3000 rpm until beads were resuspended. The oligos were annealed to the template DNA by incubation at 70° C. for 5 minutes, followed by slow cooling to room temperature.

The plate was placed on a raised bar magnetic plate for 2 minutes to pull the magnetic beads and associated DNA to the side of the wells. The supernatant was removed by pipetting, and was replaced with 50 μl of 60% BB2 (v/v in water). The beads were resuspended by vortexing, placed on the magnet again, and the supernatant was removed. This bead wash procedure was repeated once using 50 μl 60% BB2, and repeated twice more using 50 μl wash buffer (10 mM Tris pH 8.0, 1 mM EDTA, 50 mM $NaCl_2$).

The beads were resuspended in 37 μl ligation reaction mix consisting of 1× Taq ligase buffer (Enzymatics, Beverly, Mass.), 1U Taq ligase, and 2 μM bridging oligo pool (depending on the assay format), and incubated at 37° C. for one hour. Where appropriate, and depending on the assay format, a non-proofreading thermostable polymerase plus 200 nM each dNTP was included in this mixture. The plate was placed on a raised bar magnetic plate for 2 minutes to pull the magnetic beads and associated DNA to the side of the wells. The supernatant was removed by pipetting, and was replaced with 50 μL wash buffer. The beads were resuspended by vortexing, placed on the magnet again, and the supernatant was removed. The wash procedure was repeated once.

To elute the products from the strepavidin beads, 30 μl of 10 mM Tris 1 mM EDTA, pH 8.0 was added to each well of 96-well plate. The plate was sealed and mixed using an IKA vortexer for 2 minutes at 3000 rpm to resuspend the beads. The plate was incubated at 95° C. for 1 minute, and the supernatant aspirated using an 8-channel pipetter. 25 μl of supernatant from each well was transferred into a fresh 96-well plate for universal amplification.

Example 4: Universal Amplification of Tandem Ligated Products

The polymerized and/or ligated nucleic acids were amplified using universal PCR primers complementary to the universal sequences present in the first and second fixed sequence oligos hybridized to the loci of interest. 25 µl of each of the reaction mixtures of Example 3 were used in each amplification reaction. A 50 µl universal PCR reaction consisting of 25 µl eluted ligation product plus 1× Pfusion buffer, 1M Betaine, 400 nM each dNTP, 1 U Pfusion error-correcting thermostable DNA polymerase (Thermo Fisher, Waltham Mass.), and the following primer pairs: TAATGATACGGCGACCACCGAGATCTACACCG-GCGTTATGCGTCGAGA (SEQ ID NO:3) and TCAAGCAGAAGACGGCATACGAGATXAAAC-GACGCGATCATCGGTCCCC GCAA (SEQ ID NO:4), where X represents one of 96 different sample indices used to uniquely identify individual samples prior to pooling and sequencing. The PCR was carried out under stringent conditions using a BioRad Tetrad™ thermocycler.

10 µl of universal PCR product from each of the samples were pooled and the pooled PCR product was purified using AMPureXP™ SPRI beads (Beckman-Coulter, Danvers, Mass.), and quantified using Quant-iT™ PicoGreen, (Invitrogen, Carlsbad, Calif.).

Example 5: Detection and Analysis of Selected Loci

The purified PCR products of each assay format were sequenced on a single lane of a slide on an Illumina HiSeq™ 2000 (Illumina, San Diego, Calif.). Sequencing runs typically give rise to ~100M raw reads, of which ~85M (85%) mapped to expected assay structures. This translated to an average of ~885K reads/sample across the experiment, and (in the case of an experiment using 96 loci) 9.2K reads/replicate/locus across 96 loci. The mapped reads were parsed into replicate/locus/allele counts, and various metrics were computed for each condition, including:

Yield: a metric of the proportion of input DNA that was queried in sequencing, computed as the average number of unique reads per locus (only counting unique identification index reads per replicate/locus) divided by the total number of genomic equivalents contained in the input DNA.

80 percentile locus frequency range: a metric of the locus frequency variability in the sequencing data, interpreted as the fold range that encompasses 80% of the loci. It was computed on the distribution of total reads per locus, across all loci, as the $90^{th}$ percentile of total reads per locus divided by the $10^{th}$ percentile of the total reads per locus.

SNP error rate: a metric of the error rate at the SNP position, and computed as the proportion of reads containing a discordant base at the SNP position.

These results are summarized in Table 1:

TABLE 1

Results Summary of Tandem Ligation Assay Formats

| ASSAY FORMAT | FIXED SEQUENCE OLIGO ($1^{st}$ and/or $2^{nd}$) | BRIDGING OLIGO USED | ENZYME USED | YIELD | 80% LOC FREQ RANGE | SNP ERROR RATE |
|---|---|---|---|---|---|---|
| 1 | LOCUS-SPECIFIC | Locus specific | pol + lig | 9.5% | 5.3 | 0.18% |
| 2 | LOCUS-SPECIFIC | No | pol + lig | 1.4% | 58.3 | 0.19% |
| 3 | ALLELE-SPECIFIC | No | pol + lig | 0.4% | 61.7 | 1.00% |
| 4 | ALLELE-SPECIFIC | Locus specific | Taq lig | 5.0% | 5.9 | 0.92% |
| 4 | ALLELE-SPECIFIC | Locus specific | T4 lig | 5.3% | 4.4 | 0.95% |
| 5 | LOCUS-SPECIFIC | No | Taq lig | 22.5% | 1.7 | N/A |
| 6 | LOCUS-SPECIFIC | Locus specific | Taq lig | 12.5 | 2.9 | N/A |
| 7 | LOCUS-SPECIFIC | Allele specific | Taq lig | 14.3 | 2.8 | 0.20% |
| 8 | LOCUS-SPECIFIC | 2 Locus specific | Taq lig | 18.5% | 2.8 | N/A |

Table 1 indicates that the locus-specific tandem ligation assay using a bridging oligo converted template DNA into targeted product with high yield (~10%), with a high proportion of product derived from targeted loci (15% of reads did not contain expected assay structures), with limited locus bias (80% of loci fall within a ~5-fold concentration range), and with high SNP accuracy (0.2% SNP error rate). The locus-specific tandem ligation assay without the use of a bridging oligo produced reduced yields and substantial locus bias, but still produced high accuracy SNP genotyping data. The allele-specific tandem ligation assay with a bridging oligo produced intermediate yields compared to the locus-specific assay using both T4 and Taq ligase, but still produced limited locus bias and high accuracy SNP genotyping data. The allele-specific tandem ligation assay without a bridging produced reduced yields and substantial locus bias, but still produced high accuracy SNP genotyping data.

Figure 5:
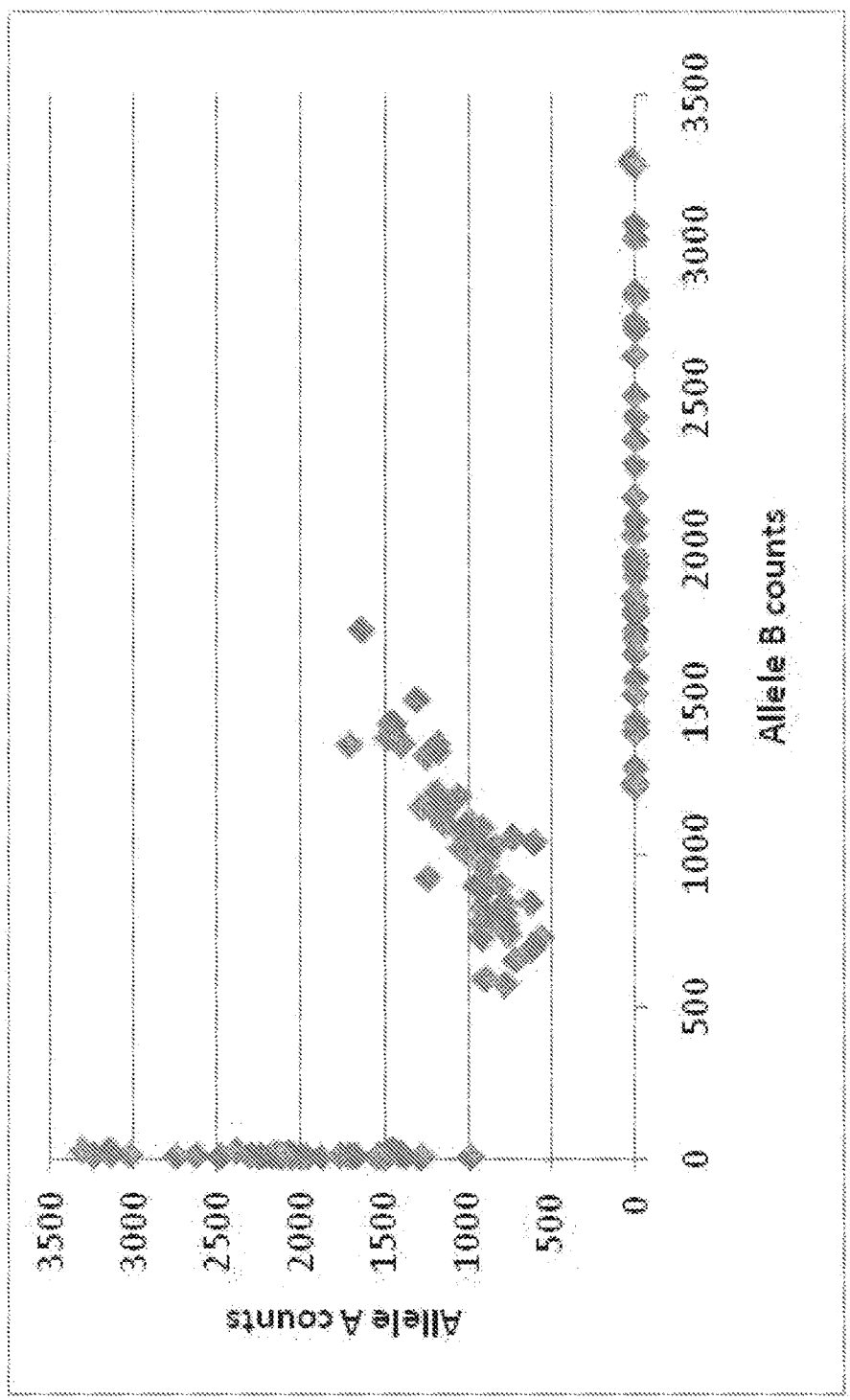
FIG. 5 illustrates the genotyping performance that was obtained using one assay system of the invention.

Assay formats six through eight showed that template DNA can be converted into targeted product with high yield (12-18%), with a high proportion of product derived from targeted loci (~76% of reads contained expected assay structures), and with limited locus bias (80% of loci fall within a 2-3-fold concentration range). FIG. 5 illustrates the genotyping performance that was obtained using assay format seven, comparing the sequence counts for the two alleles of all polymorphic assays observed in a single sample. Note the clear separation of the homozygous and heterozygous clusters, as well as the low background counts observed amongst the homozygous clusters.

Example 6: Detection of Aneuploidy in Patient Samples from Pregnant Subjects The assay systems of the invention were used in the detection of polymorphisms and chromosomal abnormalities in two separate cohorts of pregnant females. A first cohort of 190 normal, 36 T21, and 8 T18 pregnancies and a second cohort of 126 normal, 36 T21, and 8 T18 pregnancies were tested for fetal aneuploidy. The chromosomal aneuploidies were detected using 576 chromosome 21 and 576 chromosome 18 assays, pooled together and assayed in a single reaction, as set forth below.

Figure 6:
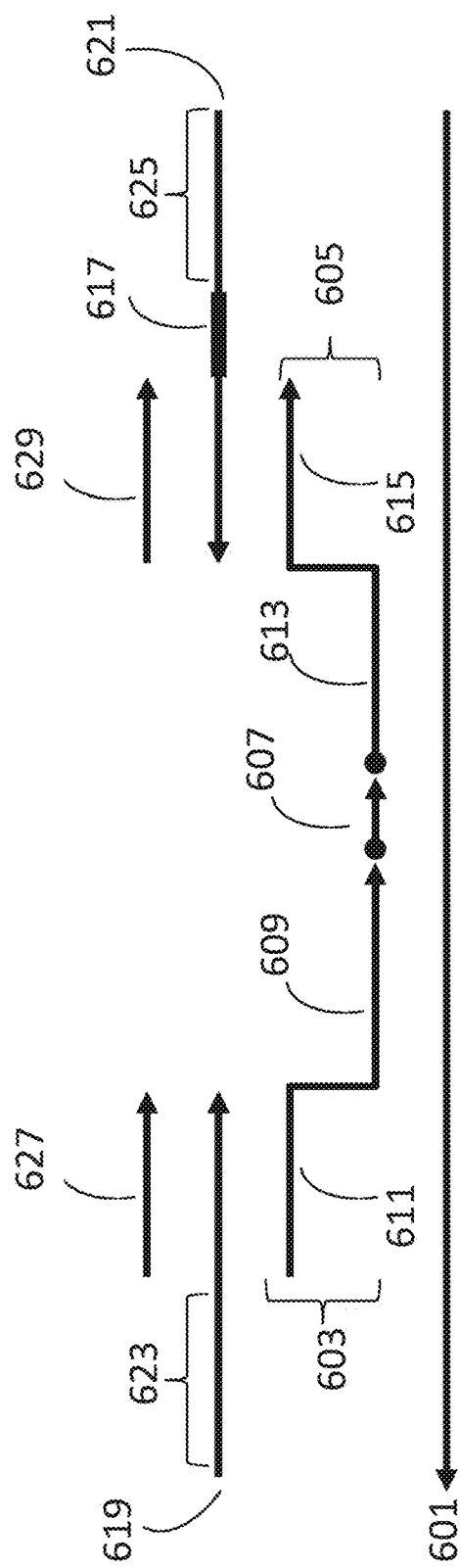
FIG. 6 illustrates the elements used for a detection of aneuploidy and polymorphism for two cohorts of maternal samples.

The elements used in the aneuploidy detection assays are illustrated in FIG. 6. The cfDNA 601 isolated from maternal samples was used as a template for hybridization, ligation, and amplification of multiple selected loci from both chromosome 21 and chromosome 18 in each maternal sample. Three oligonucleotides were hybridized to each selected locus to create ligation products for amplification and detection. The left (or first) fixed sequence oligonucleotide comprised a region complementary to a selected locus 609 and a first universal primer region 611. The right (or second) fixed sequence oligonucleotide 605 comprised a second region complementary to the selected locus 613 and a second universal primer region 615. The bridging oligonucleotides 607 used were designed so that each would hybridize to bridging regions of two or more selected loci used in the aneuploidy detection assay. When the fixed sequence oligonucleotides 603, 605 and the bridging oligonucleotide 607 hybridized to the complementary region on the cfDNA 601, their termini formed two nicks. Upon ligation of the hybridized oligonucleotides to the cfDNA, a ligation product was created for each selected locus comprising 603, 605 and 607 which was used as a template for amplification primers 619, 621.

Two amplification primers 619, 621 comprising regions complementary to the first and second universal primer regions, respectively, were then used to amplify the ligation product. This amplification product comprised the sequence of the selected locus. The right amplification primer also comprised a sample index 617 to identify the particular sample from which the locus was obtained in the multiplexed assay. Amplification with 96 distinct right amplification primers 629 enabled pooling and simultaneous sequencing of 96 different amplification products on a single lane.

The amplification primers 619, 621 also contained a left cluster sequence 623 (TAATGATACGGCGACCACCGA) (SEQ ID NO:7) and a right cluster sequence 625 (ATCTCGTATGCCGTCTTCTGCTTGA)(SEQ ID NO:8) that supported cluster amplification for sequencing using the Illumina HiSeq™ 2000 system (Illumina, San Diego, Calif.). A sequencing primer 627 comprising the first universal primer sequence was used to determine the sequence of the amplification product, and a second sequencing primer 629 was used to determine the sample index 617 of the amplification product.

Briefly, approximately 10 mL peripheral blood was collected from each patient into a BCT tube (Streck, Omaha, Nebr.), which was shipped via overnight courier to Tandem Diagnostics. Plasma was isolated from BCT tubes within 72 h of blood collection by centrifugation at 1600 g for 10 m. The plasma was transferred to a second tube and centrifuged at 16000 g for 10 m to remove any remaining cells. cfDNA was isolated from 4-5 mL plasma per patient. Approximately 15 ng cfDNA was isolated from each patient sample and arrayed into individual wells of a 96 well plate. All subsequent processing occurred on multiplexed batches of up to 96 cfDNA patient samples per array system method.

cfDNA isolated from the maternal samples in each well was biotinylated precipitated and resuspended in 30 uL TE as in Example 3 above. The biotinylated template DNA was mixed with 100 ug MyOneC1 streptavidin-coated magnetic beads (Life Technologies, Carlsbad, Calif.), 60 µl BB2 buffer (100 mM Tris pH 8.0, 10 mM EDTA, 500 mM NaCl$_2$, 58% formamide, 0.17% Tween-80), and 10 µL of pooled 40 nM left 603 and right 605 fixed sequence oligonucleotides. The mixture was heated to 70° C., and cooled 2 hours. The beads were then magnetically immobilized to the side of the well, washed twice with 50 uL 60% BB2 (v/v with H2O), washed twice more with 50 µl wash buffer (10 mM Tris pH 8.0, 1 mM EDTA, 50 mM NaCl2), and then resuspended in a 50 µL reaction containing 1U Taq ligase (Enzymatics, Beverly Mass.), 1× Taq ligase buffer (Enzymatics), and 10 uM of a 5'-phosphorylated 5mer bridging oligonucleotide 607. The mixture was incubated at 37° C. for 1 hour. The beads were again magnetically immobilized to the side of the well, washed twice with 50 uL wash buffer and then resuspended in 30 µL TE.

The ligation products were eluted from the immobilized beads by incubation at 95° C. for 3 minutes. The eluted ligation products were amplified by 26 cycles of PCR in a 50 uL reaction containing 1U Pfusion (Finnzymes), 1M Betaine, 1× Pfusion buffer, and 400 nM left and right amplification primers (619, 621 respectively). The right primer contained a 7 base sample index (617) that enabled 96 sample multiplexed sequencing on the HiSeq2000 (Illumina, San Diego, Calif.). The sequence of the left fixed sequence oligo was:

(SEQ ID NO: 5)
TAATGATACGGCGACCACCGAGATCTACACCGGCGTTATGCGTCGAGAC

And the sequence of the right fixed sequence oligo was:

(SEQ ID NO: 6)
TCAAGCAGAAGACGGCATACGAGATNNNNNNNAAACGACGCGATCATCGG

TCCCCGCAAT

Amplification products from a single 96 well plate were pooled in equal volume, and the pooled amplification products were purified with AMPureXP™ SPRI beads (Beckman-Coulter, Danvers, Mass.) according to the manufacturer's instructions. Each purified pooled library was used as template for cluster amplification on an Illumina TruSeq v2 SR cluster kit flow cell (Illumina, San Diego, Calif.) according to manufacturer's protocols. The slide was processed on an Illumina HiSeq™ 2000 (Illumina, San Diego, Calif.) to produce 56 bases of locus-specific sequence from a left sequence primer 623 and a separate read of 8 bases of sample specific sequence was obtained from the second sequence primer 625. An average of 903K raw reads per sample were collected. An average of 876K (97%) of the reads was assigned to expected assay structures.

FIG. 7 shows exemplary data for a subset of the patient samples from the second cohort, which were all analyzed in one multiplexed assay on a single lane of a sequencing run. Initially 96 different samples were run in this particular run, but—six samples were later excluded from this analytical set as not meeting sample quality control thresholds.

A trimmed mean was calculated for each chromosome 18 and chromosome 21 for the samples based on reads produced in the assay. The trimmed mean was computed by removing 10% of high and low counts for each chromosome by sample. The detected amplification products corresponding to the various selected loci were used to compute a chromosome 21 proportion metric and a chromosome 18 proportion metric for each sample. For chromosome 21 proportion, this was calculated as the trimmed mean of counts in the 384 chromosome 21 selected loci divided by the sum of trimmed means of counts for all 576 chromosome 21 loci and 576 chromosome 18 loci for each sample.

On average 834 read counts were observed per selected locus in the maternal samples of the first cohort, and 664 read counts were observed per selected locus from the second cohort. These counts were used to compute chromosome proportion z-scores for chromosome 21 and chromosome 18.

Briefly, the z-scores were calculated by scaling the median per locus count to a common value (e.g., 1000) for each sample, and the scaled counts were transformed by log base 2. An RMA log linear modeling and median polish were performed (Bolstad, B. M et al. (2003) *Bioinformatics* 19(2): 185-193; Rafael. A. (2003) *Nucleic Acids Research* 31(4):e15; Irizarry, R A et al. (2003) *Biostatistics* 4(2):249-64) to estimate chromosome effects, locus effects, sample effects, and residuals. The estimated chromosome effects were set to a common value, e.g., 0, and 2^(chromosome effect+sample effect+residual) was calculated for each locus to create normalized counts. The Z scores were scaled using iterative censoring so that they had a mean of 0 and a standard deviation of 1.

Figure 8:
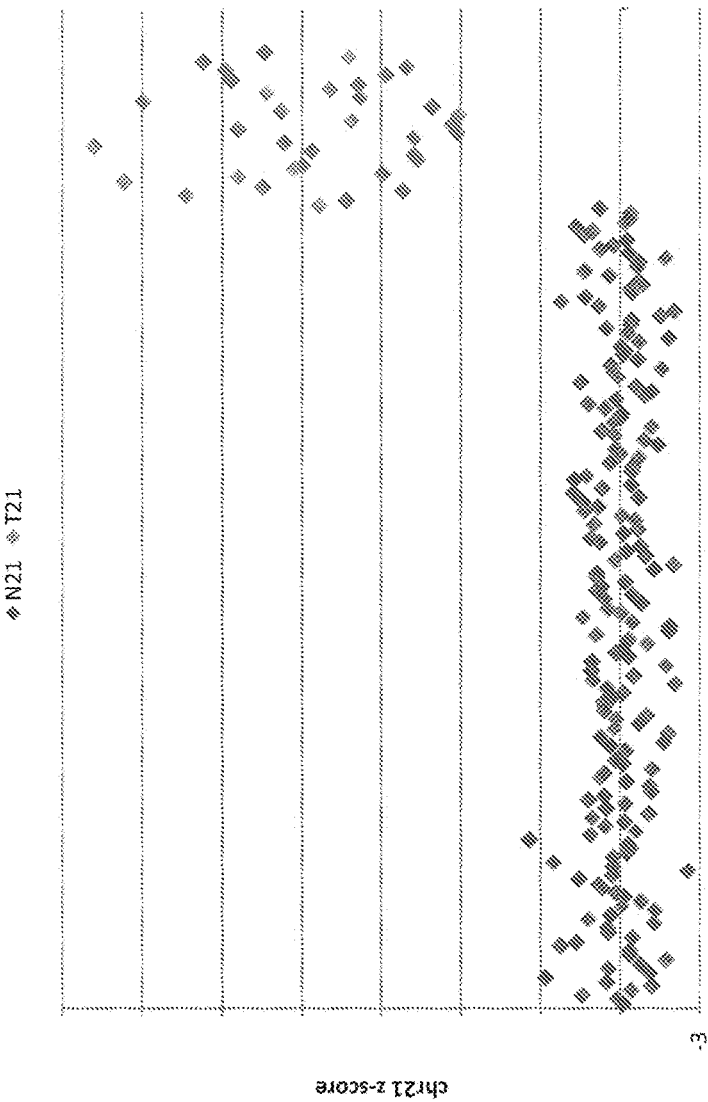
FIG. 8 illustrates the chromosome 21 aneuploidy detection achieved using one aspect of the invention for a first cohort.
Figure 9:
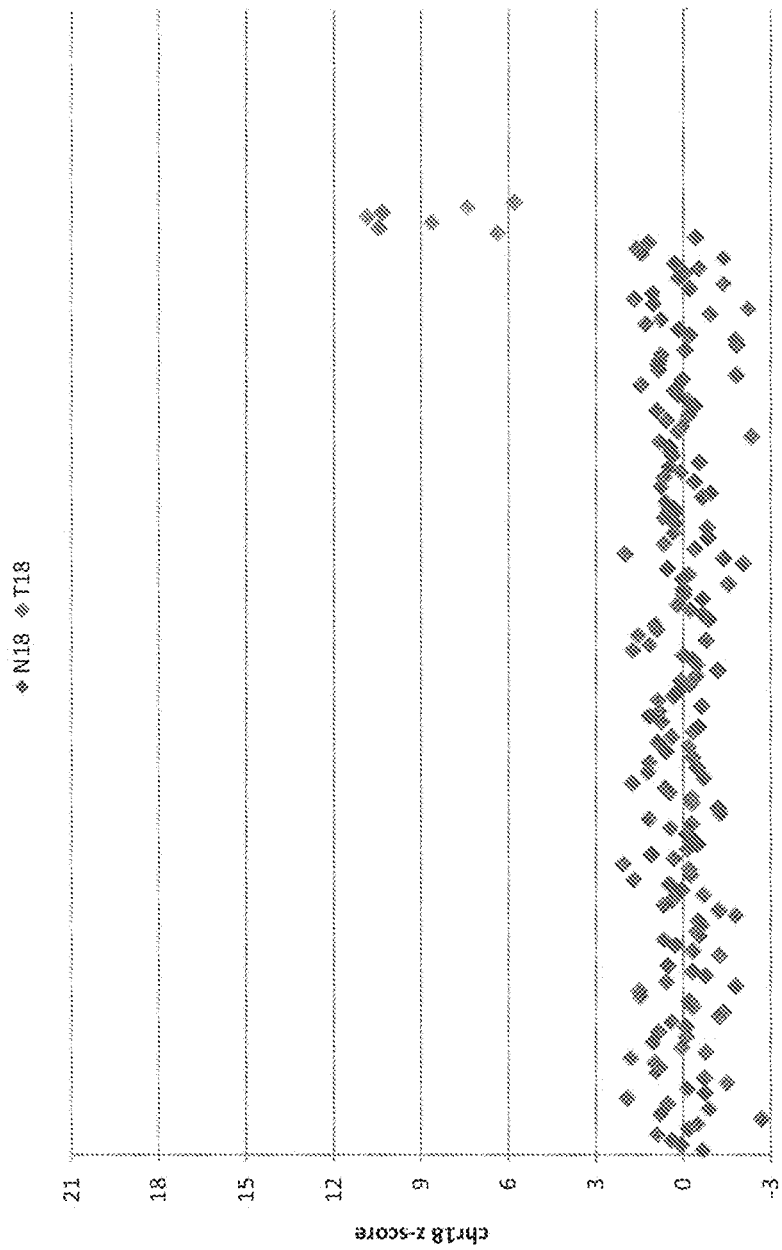
FIG. 9 illustrates the chromosome 18 aneuploidy detection achieved using one aspect of the invention for a first cohort.

Data obtained from the first cohort of samples was used to determine first cohort z-scores for chromosome 21 and chromosome 18 are illustrated in FIGS. 8 and 9, respectively. The normal samples are shown as dark grey diamonds, and the samples with a trisomy are shown as light grey diamonds. $^{179}/_{180}$ (99.4%) normal samples (dark grey diamonds) had z-scores <3; one normal sample had a chromosome 21 z-score of 3.4 and a chromosome 18 z-score of 3.0. 35/35 (100%) T21 and 7/7 (100%) T18 samples had chromosome proportion z-scores >3. The mean T18 z-score was 8.5, and the range was 5.8-10.9. The mean T21 z-score was 11.5, and the range was 6.1-19.8.

Figure 10:
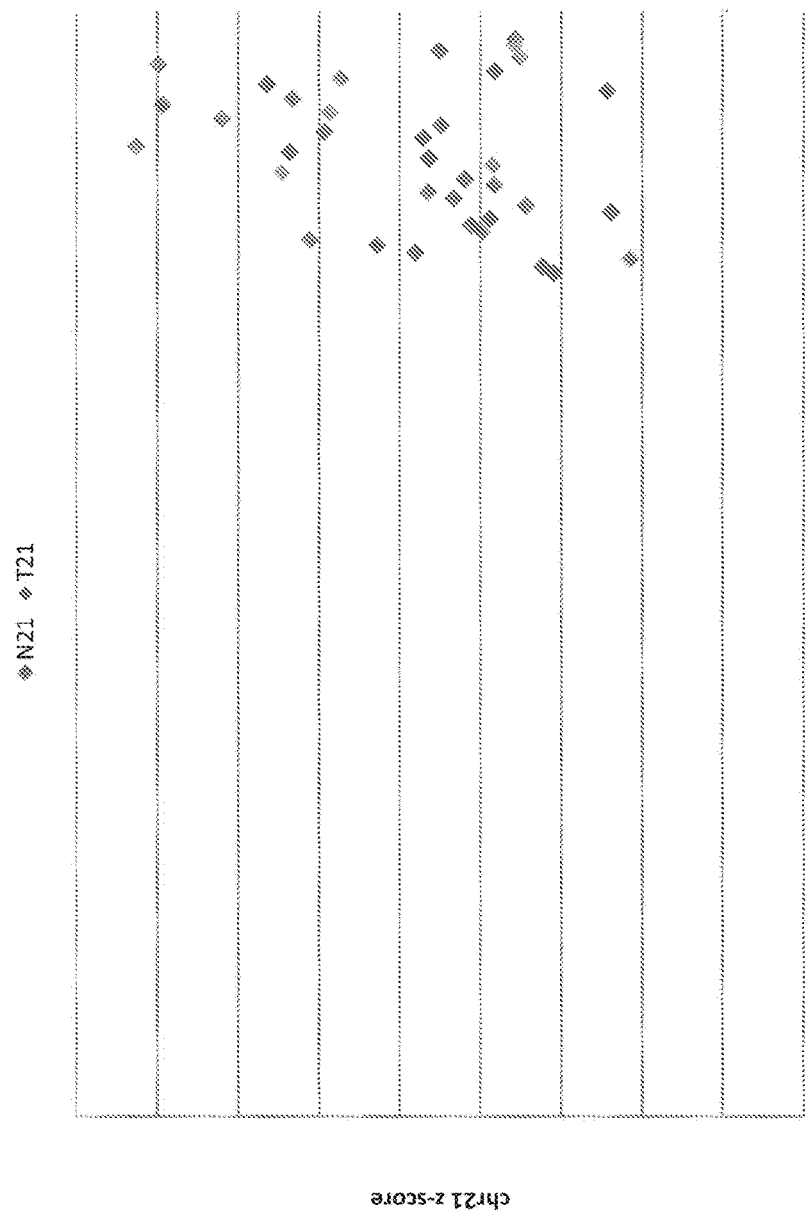
FIG. 10 illustrates the chromosome 21 aneuploidy detection achieved using one aspect of the invention for a second cohort.
Figure 11:
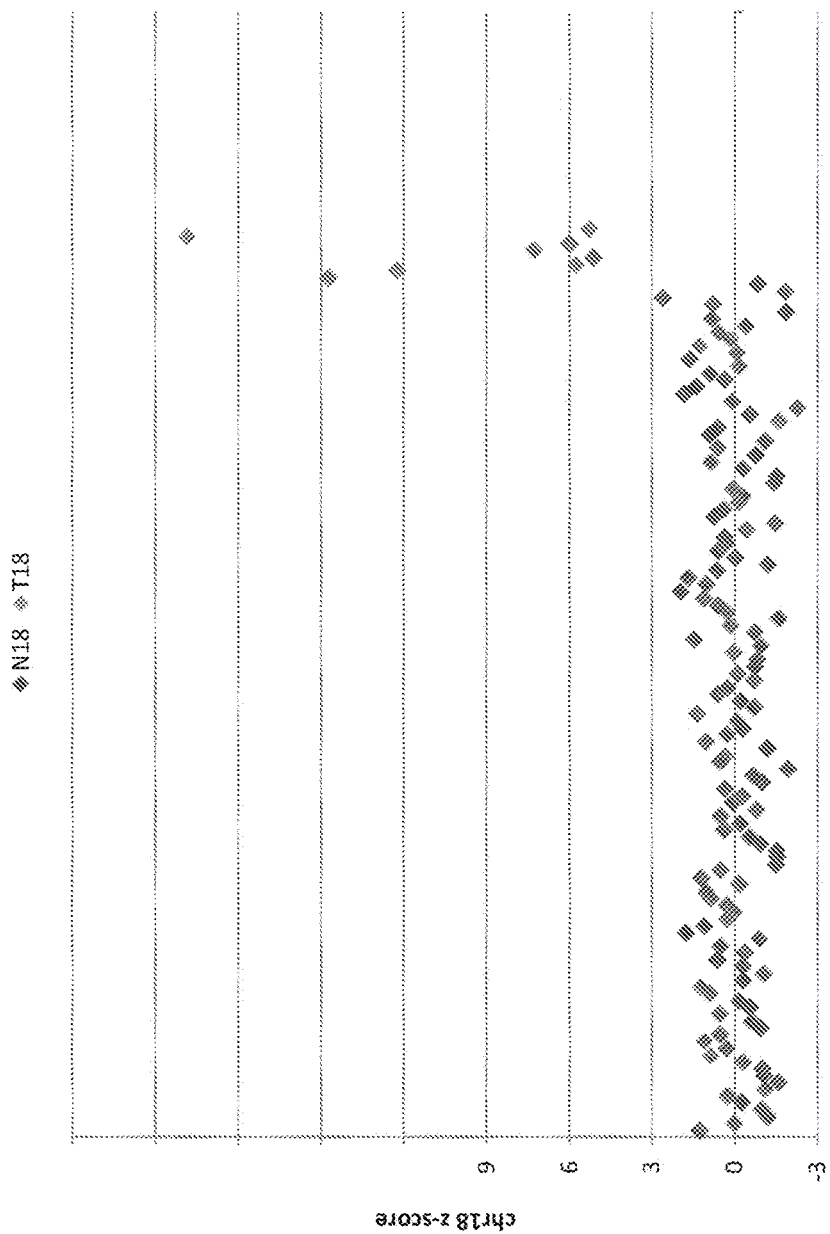
FIG. 11 illustrates the chromosome 18 aneuploidy detection achieved using one aspect of the invention for a second cohort.

The data provided in FIG. 7 was combined with data from the remaining samples of the second cohort to determine z-scores for chromosome 21 and chromosome 18 are illustrated in FIGS. 10 and 11, respectively. The normal samples are shown as dark grey diamonds, and the samples with a trisomy are shown as light grey diamonds. 125/125 normal samples had z-scores <3; 36/36 (100%) T21 and 8/8 (100%) T18 samples had z-scores >3. The mean T18 z-score was 9.5 and the range was 5.1-19.8. The mean T21 z-score was 11.4 and the range was 3.4-21.8.

In addition to the detection of aneuploidy in these cohorts, specific polymorphisms were also determined for these samples in a same assay. Specific information was obtained for individual loci as well as more general polymorphic information, such as the number of loci in which the fetal locus displayed a single nucleotide polymorphism in one allele different from the single nucleotide polymorphisms at the maternal locus (FIG. 7, #Locus DiffPoly). This determination also identified the presence of specific polymorphisms in the fetal genome. For example, the status of three exemplary polymorphism were determined using a combination of bridging oligos that were designed to bind to both the A and the T residue in the following exemplary polymorphic regions:

TABLE 2

Individual Polymorphisms Queried Using the Invention Assay

| Chromosome | Location | RSID |
|---|---|---|
| Ch01 | 01_010303942 | rs11582123 |
| TTTACATGTCTTTGGGCATTTTAGGT[A/T]GAGTGAAATCTAGGCCTTG CAAATC (SEQ ID NO: 7) | | |
| Ch03 | 03_098690592 | rs2470750 |
| TTGTGTAACGTTAACCTCAGGGACCA[A/T]GAGATGTACTTAGTATTAA TTTGCC (SEQ ID NO: 8) | | |
| Ch04 | 04_055495793 | rs6815910 |
| GGAAGAAGTGCAGTGTAGTAGACAAC[A/T]CTGGCATTGTGTTTTGTGA ACTGGG (SEQ ID NO: 9) | | |

TABLE 3

Predicted Maternal and Fetal Status for SNP rs11582123.

| Sample | SNP | A counts | T counts | Predicted Fetal Status | Predicted Maternal Status |
|---|---|---|---|---|---|
| 1 | rs11582123 | 294 | 26 | A/T | A/A |
| 2 | | 181 | 134 | A/A | A/T |
| 4 | | 34 | 330 | A/T | T/T |
| 5 | | 241 | 21 | A/T | A/A |
| 6 | | 166 | 134 | A/T | A/T |
| 7 | | 137 | 182 | T/T | A/T |
| 8 | | 199 | 135 | A/A | A/T |
| 9 | | 0 | 267 | T/T | T/T |
| 10 | | 0 | 284 | T/T | T/T |
| 11 | | 151 | 154 | A/T | A/T |
| 12 | | 294 | 1 | A/T | A/A |
| 13 | | 131 | 114 | A/A | A/T |
| 14 | | 118 | 159 | T/T | A/T |
| 15 | | 257 | 10 | A/T | A/A |
| 16 | | 309 | 31 | A/T | A/A |
| 17 | | 20 | 289 | A/T | T/A |
| 18 | | 137 | 166 | T/T | A/T |
| 19 | | 138 | 143 | A/T | A/T |
| 20 | | 24 | 242 | A/T | T/T |
| 21 | | 140 | 161 | A/T | A/T |
| 22 | | 159 | 118 | A/A | A/T |
| 23 | | 119 | 122 | A/T | A/T |
| 24 | | 0 | 250 | T/T | T/T |
| 25 | | 0 | 285 | T/T | T/T |
| 26 | | 120 | 130 | A/T | A/T |
| 28 | | 134 | 113 | A/A | A/T |
| 29 | | 109 | 118 | A/T | A/T |
| 30 | | 0 | 271 | T/T | T/T |
| 31 | | 148 | 139 | A/T | A/T |
| 32 | | 29 | 253 | A/T | T/T |
| 33 | | 0 | 304 | T/T | T/T |
| 34 | | 0 | 278 | T/T | T/T |
| 35 | | 103 | 188 | T/T | A/T |
| 36 | | 18 | 269 | A/T | T/T |
| 37 | | 279 | 34 | A/T | A/A |
| 38 | | 0 | 250 | T/T | T/T |
| 39 | | 0 | 263 | T/T | T/T |
| 40 | | 136 | 142 | A/T | A/T |
| 41 | | 147 | 145 | A/T | A/T |
| 42 | | 15 | 270 | A/T | T/T |
| 43 | | 44 | 222 | A/T | T/T |
| 44 | | 140 | 159 | T/T | A/T |
| 45 | | 0 | 259 | T/T | T/T |
| 46 | | 1 | 304 | T/T | T/T |
| 47 | | 162 | 127 | A/A | A/T |
| 48 | | 0 | 335 | T/T | T/T |
| 49 | | 1 | 247 | T/T | T/T |
| 50 | | 153 | 154 | A/T | A/T |
| 51 | | 118 | 182 | T/T | A/T |
| 52 | | 145 | 134 | A/T | A/T |
| 53 | | 146 | 132 | A/T | A/T |
| 54 | | 7 | 319 | A/T | T/T |

TABLE 3-continued

Predicted Maternal and Fetal Status for SNP rs11582123.

| Sample | SNP | A counts | T counts | Predicted Fetal Status | Predicted Maternal Status |
|---|---|---|---|---|---|
| 55 | | 152 | 174 | T/T | A/T |
| 56 | | 1 | 319 | T/T | T/T |
| 57 | | 147 | 150 | A/T | A/T |
| 58 | | 136 | 157 | T/T | A/T |
| 59 | | 83 | 162 | A/A | T/T |
| 60 | | 14 | 215 | A/T | T/T |
| 61 | | 157 | 121 | A/A | A/T |
| 62 | | 281 | 0 | A/A | A/A |
| 63 | | 0 | 260 | T/T | T/T |
| 64 | | 0 | 305 | T/T | T/T |
| 65 | | 18 | 252 | A/T | T/T |
| 66 | | 0 | 303 | T/T | T/T |
| 67 | | 99 | 161 | T/T | A/T |
| 68 | | 141 | 127 | A/T | A/T |
| 69 | | 0 | 237 | T/T | T/T |
| 70 | | 0 | 315 | T/T | T/T |
| 71 | | 132 | 139 | A/T | A/T |
| 73 | | 112 | 120 | A/T | A/T |
| 75 | | 1 | 268 | T/T | T/T |
| 76 | | 166 | 123 | A/A | T/T |
| 78 | | 0 | 245 | T/T | T/T |
| 79 | | 12 | 264 | A/T | T/T |
| 80 | | 15 | 281 | A/T | T/T |
| 81 | | 21 | 269 | A/T | T/T |
| 82 | | 108 | 160 | T/T | A/T |
| 83 | | 106 | 144 | T/T | A/T |
| 84 | | 137 | 135 | A/T | A/T |
| 85 | | 115 | 151 | T/T | A/T |
| 86 | | 0 | 262 | T/T | T/T |
| 87 | | 0 | 269 | T/T | T/T |
| 89 | | 0 | 284 | T/T | T/T |
| 90 | | 0 | 261 | T/T | T/T |
| 91 | | 143 | 137 | A/T | A/T |
| 92 | | 0 | 308 | T/T | T/T |
| 93 | | 1 | 256 | T/T | T/T |
| 94 | | 158 | 105 | A/A | A/T |
| 95 | | 149 | 103 | A/A | A/T |

TABLE 4

Predicted Maternal and Fetal Status for SNP rs2470750.

| Sample | SNP | A counts | T counts | Predicted Fetal Status | Predicted Maternal Status |
|---|---|---|---|---|---|
| 1 | rs2470750 | 243 | 15 | A/T | A/A |
| 2 | | 265 | 0 | A/A | A/A |
| 4 | | 170 | 107 | A/A | A/T |
| 5 | | 196 | 30 | A/T | A/A |
| 6 | | 141 | 144 | A/T | A/T |
| 7 | | 139 | 137 | A/T | A/T |
| 8 | | 272 | 0 | A/A | A/A |
| 9 | | 218 | 0 | A/A | A/A |
| 10 | | 216 | 0 | A/A | A/A |
| 11 | | 228 | 0 | A/A | A/A |
| 12 | | 6 | 224 | A/T | T/T |
| 13 | | 126 | 93 | A/A | A/T |
| 14 | | 125 | 123 | A/T | A/T |
| 15 | | 234 | 20 | A/T | A/A |
| 16 | | 147 | 113 | A/A | A/T |
| 17 | | 235 | 2 | A/A | A/A |
| 18 | | 129 | 142 | A/T | A/T |
| 19 | | 132 | 114 | A/A | A/T |
| 20 | | 214 | 0 | A/A | A/A |
| 21 | | 1 | 245 | T/T | T/T |
| 22 | | 141 | 111 | A/A | A/T |
| 23 | | 135 | 128 | A/A | A/T |
| 24 | | 121 | 160 | T/T | A/T |
| 25 | | 209 | 21 | A/T | A/A |
| 26 | | 0 | 239 | T/T | T/T |
| 27 | | 203 | 4 | A/T | A/A |
| 28 | | 101 | 115 | T/T | A/T |
| 29 | | 212 | 10 | A/T | A/A |
| 30 | | 86 | 101 | T/T | A/T |
| 31 | | 118 | 116 | A/T | A/T |
| 32 | | 135 | 121 | A/A | A/T |
| 33 | | 111 | 128 | T/T | A/T |
| 34 | | 120 | 118 | A/T | A/T |
| 35 | | 246 | 0 | A/A | A/A |
| 36 | | 113 | 115 | A/T | A/T |
| 37 | | 96 | 126 | T/T | A/T |
| 38 | | 107 | 88 | A/A | A/T |
| 39 | | 241 | 0 | A/A | A/A |
| 40 | | 116 | 118 | A/T | A/T |
| 41 | | 135 | 89 | A/A | A/T |
| 42 | | 129 | 85 | A/A | A/T |
| 43 | | 0 | 205 | T/T | T/T |
| 44 | | 138 | 88 | A/T | A/T |
| 45 | | 129 | 86 | A/A | A/T |
| 46 | | 108 | 123 | T/T | A/T |
| 47 | | 14 | 246 | A/T | T/T |
| 48 | | 129 | 148 | T/T | A/T |
| 49 | | 108 | 110 | A/T | A/T |
| 50 | | 120 | 124 | A/T | A/T |
| 51 | | 212 | 22 | A/T | A/T |
| 52 | | 237 | 0 | A/A | A/A |
| 53 | | 104 | 147 | T/T | A/T |
| 54 | | 134 | 126 | A/T | A/T |
| 55 | | 128 | 82 | A/A | A/T |
| 56 | | 225 | 5 | A/T | A/A |
| 57 | | 213 | 11 | A/T | A/A |
| 58 | | 125 | 116 | A/T | A/T |
| 59 | | 226 | 1 | A/A | A/A |
| 60 | | 103 | 119 | T/T | A/T |
| 61 | | 84 | 91 | T/T | A/T |
| 62 | | 130 | 104 | A/A | A/T |
| 63 | | 251 | 0 | A/A | A/A |
| 64 | | 243 | 0 | A/A | A/A |
| 65 | | 127 | 115 | A/A | A/T |
| 66 | | 113 | 104 | A/A | A/T |
| 67 | | 26 | 190 | A/T | T/T |
| 68 | | 80 | 83 | A/T | A/T |
| 69 | | 122 | 132 | T/T | A/T |
| 70 | | 0 | 235 | T/T | T/T |
| 71 | | 90 | 123 | A/T | A/T |
| 73 | | 174 | 0 | A/A | A/A |
| 75 | | 0 | 233 | T/T | T/T |
| 76 | | 220 | 0 | A/A | A/A |
| 78 | | 115 | 115 | A/T | A/T |
| 79 | | 112 | 144 | T/T | A/T |
| 80 | | 10 | 248 | A/T | T/T |
| 81 | | 241 | 0 | A/A | A/A |
| 82 | | 228 | 0 | A/A | A/A |
| 83 | | 243 | 16 | A/T | A/A |
| 84 | | 133 | 104 | A/A | A/T |
| 85 | | 101 | 99 | A/T | A/T |
| 86 | | 1 | 209 | A/A | A/A |
| 87 | | 224 | 7 | A/T | A/A |
| 89 | | 122 | 101 | A/A | A/A |
| 90 | | 130 | 89 | A/A | A/A |
| 91 | | 128 | 151 | T/T | A/T |
| 92 | | 231 | 0 | A/A | A/A |
| 93 | | 107 | 118 | T/T | A/T |
| 94 | | 93 | 100 | A/T | A/T |
| 95 | | 132 | 119 | A/A | A/T |

TABLE 5

Predicted Maternal and Fetal Status for SNP rs6S15910.

| Sample | SNP | A counts | T counts | Predicted Fetal Status | Predicted Maternal Status |
|---|---|---|---|---|---|
| 1 | rs6815910 | 295 | 32 | A/T | A/A |
| 10 | | 133 | 107 | A/A | A/T |
| 11 | | 115 | 131 | T/T | A/T |
| 12 | | 311 | 10 | A/T | A/A |
| 13 | | 18 | 252 | A/T | T/T |
| 14 | | 132 | 178 | T/T | A/T |
| 15 | | 288 | 0 | A/A | A/A |
| 16 | | 325 | 1 | A/A | A/A |
| 17 | | 11 | 276 | A/T | T/T |
| 18 | | 282 | 0 | A/A | A/A |
| 19 | | 131 | 133 | A/T | A/T |
| 2 | | 7 | 311 | A/T | T/T |
| 20 | | 135 | 116 | A/A | A/T |
| 21 | | 121 | 140 | T/T | A/T |
| 22 | | 287 | 11 | A/T | A/A |
| 23 | | 148 | 146 | A/T | A/T |
| 24 | | 185 | 138 | A/A | A/T |
| 25 | | 116 | 126 | T/T | A/T |
| 26 | | 235 | 0 | A/A | A/A |
| 27 | | 288 | 0 | A/A | A/A |
| 28 | | 242 | 0 | A/A | A/A |
| 29 | | 239 | 12 | A/T | A/A |
| 30 | | 235 | 24 | A/T | A/A |
| 31 | | 126 | 148 | T/T | A/T |
| 32 | | 25 | 256 | A/T | T/T |
| 33 | | 286 | 1 | A/A | A/A |
| 34 | | 158 | 156 | A/T | A/T |
| 35 | | 287 | 0 | A/A | A/A |
| 36 | | 118 | 133 | T/T | A/T |
| 37 | | 163 | 119 | A/A | A/T |
| 38 | | 273 | 10 | A/T | A/A |
| 39 | | 132 | 148 | T/T | A/T |
| 4 | | 0 | 343 | T/T | T/T |
| 40 | | 143 | 177 | T/T | A/T |
| 41 | | 0 | 308 | T/T | T/T |
| 42 | | 297 | 0 | A/A | A/A |
| 43 | | 117 | 130 | T/T | A/T |
| 44 | | 296 | 1 | A/A | A/A |
| 45 | | 276 | 0 | A/A | A/A |
| 46 | | 140 | 134 | A/T | A/T |
| 47 | | 158 | 139 | A/A | A/T |
| 48 | | 0 | 304 | T/T | T/T |
| 49 | | 251 | 13 | A/T | A/A |
| 5 | | 138 | 115 | A/A | A/T |
| 50 | | 142 | 162 | T/T | A/T |
| 51 | | 0 | 306 | T/T | T/T |
| 52 | | 249 | 21 | A/T | A/A |
| 53 | | 111 | 170 | T/T | A/T |
| 54 | | 140 | 151 | A/T | A/T |
| 55 | | 102 | 217 | T/T | A/T |
| 56 | | 315 | 0 | A/A | A/A |
| 57 | | 123 | 158 | T/T | A/T |
| 58 | | 146 | 168 | T/T | A/T |
| 59 | | 226 | 50 | A/T | A/A |
| 6 | | 309 | 0 | A/A | A/A |
| 60 | | 122 | 133 | T/T | A/T |
| 61 | | 240 | 28 | A/T | A/A |
| 62 | | 132 | 124 | A/T | A/T |
| 63 | | 291 | 9 | A/T | A/A |
| 64 | | 0 | 304 | T/T | T/T |
| 65 | | 273 | 0 | A/A | A/A |
| 66 | | 154 | 139 | A/T | A/T |
| 67 | | 145 | 153 | A/T | A/T |
| 68 | | 110 | 163 | T/T | A/T |
| 69 | | 131 | 134 | A/T | A/T |
| 7 | | 186 | 127 | A/A | A/T |
| 70 | | 167 | 163 | A/T | A/T |
| 71 | | 238 | 26 | A/T | A/A |
| 73 | | 18 | 244 | A/T | T/T |
| 75 | | 130 | 129 | A/T | A/T |
| 76 | | 133 | 113 | A/A | A/T |
| 78 | | 237 | 2 | A/T | A/A |
| 79 | | 0 | 278 | T/T | T/T |
| 8 | | 192 | 159 | A/A | A/T |
| 80 | | 153 | 131 | A/A | A/T |
| 81 | | 25 | 229 | A/T | T/T |
| 82 | | 0 | 256 | T/T | T/T |
| 83 | | 152 | 142 | A/T | A/T |
| 84 | | 290 | 2 | A/T | A/A |
| 85 | | 270 | 0 | A/A | A/A |
| 86 | | 0 | 242 | T/T | T/T |
| 87 | | 150 | 134 | A/A | A/T |
| 89 | | 169 | 117 | A/A | A/T |
| 9 | | 271 | 1 | A/A | A/A |
| 90 | | 109 | 144 | T/T | A/T |
| 91 | | 261 | 12 | A/T | A/A |
| 92 | | 258 | 0 | A/A | A/A |
| 93 | | 0 | 309 | T/T | T/T |
| 94 | | 116 | 146 | T/T | A/T |
| 95 | | 123 | 116 | A/T | A/T |

The location of these SNPS is denoted using dbSNP version 132 and GRCH37/UCSC hg 19. The data for these polymorphisms was obtained in the same data set as the aneuploidy data illustrated in FIGS. 10 and 11. Thus, a single assay demonstrated the ability to identify fetal aneuploidy, polymorphic differences between fetal and maternal loci, and the actual SNP information for selected fetal loci in a single assay.

Numerous variations may be made by persons skilled in the art without departure from the spirit of the invention. The scope of the invention will be measured by the appended claims and their equivalents. The abstract and the title are not to be construed as limiting the scope of the present invention, as their purpose is to enable the appropriate authorities, as well as the general public, to quickly determine the general nature of the invention. In the claims that follow, unless the term "means" is used, none of the features or elements recited therein should be construed as means-plus-function limitations pursuant to 35 U.S.C. § 112, ¶6.

What is claimed is:

1. A method of detecting a presence or absence of copy number variation (CNV) in a mixed sample from a single subject, said mixed sample comprising nucleic acids from at least two sources comprising a major source and a minor source, the method comprising:
   a) hybridizing at least 24 first sets of two fixed sequence oligonucleotides to the nucleic acids in the mixed sample, wherein each first set of two fixed sequence oligonucleotides is complementary to a locus in a first region of interest, each first set of two fixed sequence oligonucleotides comprising universal primer regions, and wherein melting temperatures ($T_m$s) of first fixed sequence oligonucleotides of each first set of two fixed sequence oligonucleotides vary in a range of two degrees centigrade;
   b) hybridizing at least 24 second sets of two fixed sequence oligonucleotides to the nucleic acids in the mixed sample, wherein each second set of two fixed sequence oligonucleotides is complementary to a locus in a second region of interest, each second set of two fixed sequence oligonucleotides comprising universal primer regions, and wherein $T_m$s of first fixed sequence oligonucleotides of each second set of two fixed sequence oligonucleotides vary in a range of two degrees centigrade;

c) extending one of said hybridized fixed sequence oligonucleotides of each first set of two fixed sequence oligonucleotides with a polymerase between the hybridized oligonucleotides of each first set of two fixed sequence oligonucleotides to produce adjacently hybridized fixed sequence oligonucleotides and extending one of said hybridized fixed sequence oligonucleotides of each second set of two fixed sequence oligonucleotides with a polymerase between the hybridized oligonucleotides of each second set of two fixed sequence oligonucleotides to produce adjacently hybridized fixed sequence oligonucleotides;

d) ligating the adjacently hybridized fixed sequence oligonucleotides of each first set of two fixed sequence oligonucleotides to create contiguous ligation products and ligating the adjacently hybridized fixed sequence oligonucleotides of each second set of two fixed sequence oligonucleotides to create contiguous ligation products;

e) amplifying the contiguous ligation products using the universal primer regions on each first and second sets of two fixed sequence oligonucleotides to produce amplification products;

f) detecting the amplification products; and g) detecting a copy number variation of the first region of interest relative to the second region of interest.

2. The method of claim 1, wherein the subject comprises a pregnant female such that the nucleic acids of the major source comprise maternal nucleic acids and the nucleic acids of the minor source comprise fetal nucleic acids.

3. The method of claim 1, wherein the subject comprises an individual having normal cells and cancerous cells such that the nucleic acids of the major source comprise nucleic acids of the normal cells and the nucleic acids of the minor source comprise nucleic acids of the cancerous cells.

4. The method of claim 1, wherein the subject comprises a transplant patient such that the nucleic acids of the major source comprise nucleic acids of the patient and the nucleic acids of the minor source comprise nucleic acids of a donor organ, and wherein said copy number variation is detected in said major source or said minor source.

5. The method of claim 1, wherein the subject comprises an individual infected with an organism such that the nucleic acids of the major source comprise nucleic acids of the individual and the nucleic acids of the minor source comprise nucleic acids of the infectious organism, and wherein said copy number variation is detected in said major source or said minor source.

6. The method of claim 1, wherein each locus in the second region of interest comprises one or more polymorphisms.

7. The method of claim 1, wherein the first region of interest and the second region of interest are on different chromosomes.

8. The method of claim 1, wherein at least one locus does not comprise a polymorphism.

9. The method of claim 1, wherein one or both sets of the fixed sequence oligonucleotides comprises at least one index.

10. The method of claim 9, wherein the amplification products are detected by sequencing the at least one index.

11. The method of claim 9, wherein the at least one index comprises a locus index.

12. The method of claim 9, wherein the at least one index comprises a sample index.

13. The method of claim 1, wherein the amplification products are detected by high throughput sequencing.

14. The method of claim 1, wherein the amplification products are detected on an array.

15. The method of claim 1, wherein one or both sets of fixed sequence oligonucleotides comprises an oligonucleotide 5' of each locus, an oligonucleotide 3' of each locus, and a bridging oligonucleotide.

16. The method of claim 1, wherein one or more bridging oligonucleotides is added prior to the step of extension.

17. The method of claim 1, wherein the amplification products are isolated as individual molecules prior to detection.

18. The method of claim 17, wherein the individual isolated amplification products are further amplified to create identical copies of all or a portion of the individual amplification products prior to detection.

19. A method of detecting a presence or absence of genetic variation in a mixed sample from a single subject, said mixed sample comprising nucleic acids from at least two sources comprising a major source and a minor source, the method comprising:

a) hybridizing at least 24 sets of two fixed sequence oligonucleotides to the nucleic acids in the mixed sample, wherein each set of two fixed sequence oligonucleotides is complementary to a polymorphic locus in a region of interest, each set of two fixed sequence oligonucleotides comprising universal primer regions, and each locus in the region of interest having different genotypes in the major source and the minor source, and wherein $T_m$s of first fixed sequence oligonucleotides of each set of two fixed sequence oligonucleotides vary in a range of two degrees centigrade;

b) extending one of said hybridized two fixed sequence oligonucleotides of each set with a polymerase between the hybridized oligonucleotides of the set to produce adjacently hybridized fixed sequence oligonucleotides;

c) ligating the adjacently hybridized oligonucleotides to create contiguous ligation products complementary to the locus;

d) amplifying the contiguous ligation products using the universal primer regions on the two fixed sequence oligonucleotides of each set of fixed sequence oligonucleotides to produce amplification products;

e) detecting the amplification products; and f) detecting a presence or absence of genetic variation in the locus of interest between the major and minor sources from the detected amplified products.

* * * * *